United States Patent
Sverdlik et al.

(10) Patent No.: US 10,357,304 B2
(45) Date of Patent: Jul. 23, 2019

(54) TISSUE TREATMENT

(71) Applicant: CardioSonic Ltd., Tel-Aviv (IL)

(72) Inventors: Ariel Sverdlik, Tel-Aviv (IL); Yehuda Zadok, Holon (IL); Or Shabtay, Kibbutz Farod (IL); Iris Szwarcfiter, Tel-Aviv (IL); Avital Schauder, Lod (IL); Krishna J. Rocha-Singh, Springfield, IL (US)

(73) Assignee: CardioSonic Ltd., Tel-Aviv (IL)

( * ) Notice: Subject to any disclaimer, the term of this patent is extended or adjusted under 35 U.S.C. 154(b) by 346 days.

(21) Appl. No.: 14/394,276

(22) PCT Filed: Apr. 18, 2013

(86) PCT No.: PCT/IL2013/050341
§ 371 (c)(1),
(2) Date: Oct. 14, 2014

(87) PCT Pub. No.: WO2013/157011
PCT Pub. Date: Oct. 24, 2013

(65) Prior Publication Data
US 2015/0073400 A1    Mar. 12, 2015

Related U.S. Application Data

(60) Provisional application No. 61/625,810, filed on Apr. 18, 2012.

(51) Int. Cl.
*A61B 18/08* (2006.01)
*A61N 7/02* (2006.01)
*A61B 18/00* (2006.01)

(52) U.S. Cl.
CPC ............ *A61B 18/082* (2013.01); *A61N 7/022* (2013.01); *A61B 2018/00375* (2013.01);
(Continued)

(58) Field of Classification Search
CPC .......... A61B 2018/00375; A61B 2018/00404; A61B 2018/00434; A61B 2018/00511; A61B 2018/00577
See application file for complete search history.

(56) References Cited

U.S. PATENT DOCUMENTS

| | | |
|---|---|---|
| 4,319,580 A | 3/1982 | Colley et al. |
| 5,038,789 A | 8/1991 | Frazin |

(Continued)

FOREIGN PATENT DOCUMENTS

| | | |
|---|---|---|
| CN | 1279595 | 1/2001 |
| CN | 101610735 | 12/2009 |

(Continued)

OTHER PUBLICATIONS

Applicant-Initiated Interview Summary dated Jan. 4, 2016 From the US Patent and Trademark Office Re. U.S. Appl. No. 13/449,539.
(Continued)

*Primary Examiner* — Jaymi E Della

(57) ABSTRACT

There is provided in accordance with an exemplary embodiment of the invention a method and/or a device of treating tissue near a first lumen comprising inserting an energy emission element into a second lumen and delivering energy in an amount sufficient to cause one or more spaced apart areas of tissue damage at preselected locations in tissue near the first lumen. There is also provided a method and/or a device for treating a carotid artery wall, for example, to reduce signal conduction. There is also provided a method and/or a device for treating a wall of a lumen in a limb, for example, to increase blood flow. There is also provided a method and/or a device for treating a wall of a heart, for example, to stop abnormal signal propagation.

11 Claims, 27 Drawing Sheets
(13 of 27 Drawing Sheet(s) Filed in Color)

(52) U.S. Cl.
CPC ............... *A61B 2018/00404* (2013.01); *A61B 2018/00434* (2013.01); *A61B 2018/00511* (2013.01); *A61B 2018/00577* (2013.01)

(56) References Cited

U.S. PATENT DOCUMENTS

| | | |
|---|---|---|
| 5,226,847 A | 7/1993 | Thomas, III et al. |
| 5,421,338 A | 6/1995 | Crowley et al. |
| 5,467,251 A | 11/1995 | Katchmar |
| 5,471,988 A | 12/1995 | Fujio et al. |
| 5,524,630 A | 6/1996 | Crowley |
| 5,590,653 A | 1/1997 | Aida et al. |
| 5,620,417 A | 4/1997 | Jang et al. |
| 5,657,760 A | 8/1997 | Ying et al. |
| 5,699,804 A | 12/1997 | Rattner |
| 5,707,367 A | 1/1998 | Nilsson |
| 5,735,280 A | 4/1998 | Sherman et al. |
| 5,762,066 A | 6/1998 | Law et al. |
| 5,772,642 A | 6/1998 | Ciamacco, Jr. et al. |
| 5,895,355 A | 4/1999 | Schaer |
| 5,895,356 A | 4/1999 | Andrus et al. |
| 5,971,949 A | 10/1999 | Levin et al. |
| 6,007,499 A | 12/1999 | Martin et al. |
| 6,042,556 A | 3/2000 | Beach et al. |
| 6,073,048 A | 6/2000 | Kieval et al. |
| 6,077,225 A | 6/2000 | Brock-Fisher |
| 6,117,101 A | 9/2000 | Diederich et al. |
| 6,119,041 A | 9/2000 | Pomeranz et al. |
| 6,165,127 A | 12/2000 | Crowley |
| 6,210,393 B1 | 4/2001 | Brisken |
| 6,216,041 B1 | 4/2001 | Tierney et al. |
| 6,235,024 B1* | 5/2001 | Tu ..................... A61B 17/2202 600/439 |
| 6,261,233 B1 | 7/2001 | Kantorovich |
| 6,296,619 B1 | 10/2001 | Brisken et al. |
| 6,379,320 B1 | 4/2002 | Lafon et al. |
| 6,428,477 B1 | 8/2002 | Mason |
| 6,451,013 B1 | 9/2002 | Bays et al. |
| 6,500,121 B1 | 12/2002 | Slayton et al. |
| 6,511,428 B1 | 1/2003 | Azuma et al. |
| 6,511,436 B1 | 1/2003 | Asmar |
| 6,514,249 B1 | 2/2003 | Maguire et al. |
| 6,527,759 B1 | 3/2003 | Tachibana et al. |
| 6,547,788 B1 | 4/2003 | Maguire et al. |
| 6,599,288 B2 | 7/2003 | Maguire et al. |
| 6,607,502 B1 | 8/2003 | Maguire et al. |
| 6,645,147 B1 | 11/2003 | Jackson et al. |
| 6,740,040 B1 | 5/2004 | Mandrusov et al. |
| 6,752,805 B2 | 6/2004 | Maguire et al. |
| 6,953,460 B2 | 10/2005 | Maguire et al. |
| 6,955,173 B2 | 10/2005 | Lesh |
| 6,978,174 B2 | 12/2005 | Gelfand et al. |
| 7,001,336 B2 | 2/2006 | Mandrusov et al. |
| 7,037,271 B2 | 5/2006 | Crowley |
| 7,084,004 B2 | 8/2006 | Vaiyapuri et al. |
| 7,156,816 B2 | 1/2007 | Schwartz et al. |
| 7,162,303 B2 | 1/2007 | Levin et al. |
| 7,166,098 B1 | 1/2007 | Steward et al. |
| 7,220,233 B2 | 5/2007 | Nita et al. |
| 7,220,258 B2 | 5/2007 | Myhr |
| 7,220,261 B2 | 5/2007 | Truckai et al. |
| 7,285,116 B2 | 10/2007 | De la Rama et al. |
| 7,326,201 B2 | 2/2008 | Fjield et al. |
| 7,341,583 B2 | 3/2008 | Shiono et al. |
| 7,344,529 B2 | 3/2008 | Torchia et al. |
| 7,347,859 B2 | 3/2008 | Garabedian et al. |
| 7,410,486 B2 | 8/2008 | Fuimaono et al. |
| 7,460,369 B1 | 12/2008 | Blish, II |
| 7,470,241 B2 | 12/2008 | Weng et al. |
| 7,479,106 B2 | 1/2009 | Banik et al. |
| 7,510,536 B2 | 3/2009 | Foley et al. |
| 7,538,425 B2 | 5/2009 | Myers et al. |
| RE40,815 E | 6/2009 | Kudaravalli et al. |
| 7,540,846 B2 | 6/2009 | Harhen et al. |
| 7,540,870 B2 | 6/2009 | Babaev |
| 7,563,260 B2 | 7/2009 | Whitmore et al. |
| 7,617,005 B2 | 11/2009 | Demarais et al. |
| 7,620,451 B2 | 11/2009 | Demarais et al. |
| 7,621,929 B2 | 11/2009 | Nita et al. |
| 7,647,115 B2 | 1/2010 | Levin et al. |
| 7,653,438 B2 | 1/2010 | Deem et al. |
| 7,655,005 B2 | 2/2010 | Bhola |
| 7,678,104 B2 | 3/2010 | Keidar |
| 7,704,212 B2 | 4/2010 | Wekell et al. |
| 7,713,210 B2 | 5/2010 | Byrd et al. |
| 7,717,948 B2 | 5/2010 | Demarais et al. |
| 7,727,228 B2 | 6/2010 | Abboud et al. |
| 7,736,317 B2 | 6/2010 | Stephens et al. |
| 7,756,583 B2 | 7/2010 | Demarais et al. |
| 7,762,954 B2 | 7/2010 | Nix et al. |
| 7,771,372 B2 | 8/2010 | Wilson |
| 7,819,868 B2 | 10/2010 | Cao et al. |
| 7,824,348 B2 | 11/2010 | Barthe et al. |
| 7,850,683 B2 | 12/2010 | Elkins et al. |
| 7,850,685 B2 | 12/2010 | Kunis et al. |
| 7,853,333 B2 | 12/2010 | Demarais |
| 7,854,733 B2 | 12/2010 | Govari |
| 7,883,506 B2 | 2/2011 | McIntyre et al. |
| 7,940,969 B2 | 5/2011 | Nair et al. |
| 8,216,216 B2 | 7/2012 | Warnking et al. |
| 8,221,402 B2 | 7/2012 | Francischelli et al. |
| 8,401,667 B2 | 3/2013 | Gustus et al. |
| 8,419,729 B2 | 4/2013 | Ibrahim et al. |
| 8,540,662 B2 | 9/2013 | Stehr et al. |
| 8,568,403 B2 | 10/2013 | Soltesz et al. |
| 8,585,695 B2 | 11/2013 | Shih |
| 8,974,446 B2 | 3/2015 | Nguyen et al. |
| 2001/0007940 A1 | 7/2001 | Tu et al. |
| 2001/0014780 A1 | 8/2001 | Martin et al. |
| 2001/0053885 A1 | 12/2001 | Gielen et al. |
| 2002/0002371 A1 | 1/2002 | Acker et al. |
| 2002/0016624 A1* | 2/2002 | Patterson ........... A61B 17/3207 623/1.12 |
| 2002/0019627 A1 | 2/2002 | Maguire et al. |
| 2002/0022833 A1 | 2/2002 | Maguire et al. |
| 2002/0026127 A1 | 2/2002 | Balbierz et al. |
| 2002/0048310 A1 | 4/2002 | Heuser |
| 2002/0055754 A1 | 5/2002 | Ranucci et al. |
| 2002/0065512 A1 | 5/2002 | Fjield et al. |
| 2002/0077643 A1 | 6/2002 | Rabiner et al. |
| 2002/0169394 A1 | 11/2002 | Eppstein et al. |
| 2002/0188218 A1 | 12/2002 | Lipman |
| 2003/0013968 A1 | 1/2003 | Fjield et al. |
| 2003/0092667 A1 | 5/2003 | Tachibana et al. |
| 2003/0125726 A1 | 7/2003 | Maguire et al. |
| 2003/0151417 A1 | 8/2003 | Koen |
| 2003/0181901 A1 | 9/2003 | Maguire et al. |
| 2003/0195496 A1 | 10/2003 | Maguire et al. |
| 2003/0199747 A1 | 10/2003 | Michlitsch et al. |
| 2003/0199768 A1 | 10/2003 | Cespededs et al. |
| 2004/0006333 A1 | 1/2004 | Arnold et al. |
| 2004/0019687 A1 | 1/2004 | Ozawa et al. |
| 2004/0073660 A1 | 4/2004 | Toomey |
| 2004/0082859 A1 | 4/2004 | Schaer |
| 2004/0102361 A1 | 5/2004 | Bodin |
| 2004/0102769 A1 | 5/2004 | Schwartz et al. |
| 2005/0015079 A1 | 1/2005 | Keider |
| 2005/0020967 A1 | 1/2005 | Ono |
| 2005/0096542 A1 | 5/2005 | Weng |
| 2005/0096647 A1 | 5/2005 | Steinke et al. |
| 2005/0215946 A1 | 9/2005 | Hansmann et al. |
| 2005/0240170 A1 | 10/2005 | Zhang et al. |
| 2005/0288730 A1 | 12/2005 | Deem et al. |
| 2006/0009753 A1 | 1/2006 | Fjield et al. |
| 2006/0052774 A1 | 3/2006 | Garrison et al. |
| 2006/0058711 A1 | 3/2006 | Harhen et al. |
| 2006/0079816 A1 | 4/2006 | Barthe et al. |
| 2006/0084966 A1 | 4/2006 | Maguire et al. |
| 2006/0173387 A1 | 8/2006 | Hansmann et al. |
| 2006/0229594 A1 | 10/2006 | Francischelli et al. |
| 2006/0241442 A1 | 10/2006 | Barthe et al. |
| 2006/0241739 A1 | 10/2006 | Besselink et al. |
| 2006/0264809 A1 | 11/2006 | Hansmann et al. |
| 2007/0043297 A1 | 2/2007 | Miyazawa |

(56) References Cited

U.S. PATENT DOCUMENTS

| | | |
|---|---|---|
| 2007/0088346 A1 | 4/2007 | Mirizzi et al. |
| 2007/0142831 A1 | 6/2007 | Shadduck |
| 2007/0142879 A1 | 6/2007 | Greenberg et al. |
| 2007/0167824 A1 | 7/2007 | Lee et al. |
| 2007/0203479 A1 | 8/2007 | Auth et al. |
| 2007/0222339 A1 | 9/2007 | Lukacs et al. |
| 2007/0225619 A1 | 9/2007 | Rabiner et al. |
| 2007/0233057 A1 | 10/2007 | Konishi |
| 2007/0249997 A1 | 10/2007 | Goodson, IV et al. |
| 2007/0282407 A1* | 12/2007 | Demarais ............... A61F 7/123 607/113 |
| 2008/0039745 A1 | 2/2008 | Babaev |
| 2008/0077202 A1 | 3/2008 | Levinson |
| 2008/0086073 A1 | 4/2008 | McDaniel |
| 2008/0114354 A1 | 5/2008 | Whayne et al. |
| 2008/0125829 A1 | 5/2008 | Velasco et al. |
| 2008/0139971 A1 | 6/2008 | Lockhart |
| 2008/0146924 A1 | 6/2008 | Smith et al. |
| 2008/0171934 A1 | 7/2008 | Greenan et al. |
| 2008/0179736 A1 | 7/2008 | Hartwell et al. |
| 2008/0183110 A1 | 7/2008 | Davenport et al. |
| 2008/0195000 A1 | 8/2008 | Spooner et al. |
| 2008/0214966 A1 | 9/2008 | Slayton et al. |
| 2008/0215039 A1 | 9/2008 | Slatkine et al. |
| 2008/0228111 A1 | 9/2008 | Nita |
| 2008/0249518 A1 | 10/2008 | Warnking et al. |
| 2008/0281297 A1 | 11/2008 | Pesach et al. |
| 2008/0300571 A1 | 12/2008 | LePivert |
| 2008/0300655 A1 | 12/2008 | Cholette |
| 2008/0312643 A1 | 12/2008 | Kania et al. |
| 2009/0018446 A1 | 1/2009 | Medan et al. |
| 2009/0036914 A1 | 2/2009 | Houser |
| 2009/0093737 A1 | 4/2009 | Chomas et al. |
| 2009/0131930 A1 | 5/2009 | Gelbart et al. |
| 2009/0149782 A1 | 6/2009 | Cohen et al. |
| 2009/0163807 A1 | 6/2009 | Sliwa |
| 2009/0216246 A1 | 8/2009 | Nita et al. |
| 2009/0221939 A1 | 9/2009 | Demarais et al. |
| 2009/0221955 A1 | 9/2009 | Babaev |
| 2009/0254078 A1 | 10/2009 | Just et al. |
| 2009/0281478 A1 | 11/2009 | Duke |
| 2009/0299360 A1 | 12/2009 | Ormsby |
| 2010/0036293 A1 | 2/2010 | Isola et al. |
| 2010/0081933 A1* | 4/2010 | Sverdlik ............... A61B 5/0048 600/439 |
| 2010/0091112 A1 | 4/2010 | Veeser et al. |
| 2010/0114082 A1 | 5/2010 | Sharma |
| 2010/0125198 A1 | 5/2010 | Thapliyal et al. |
| 2010/0130892 A1 | 5/2010 | Warnking |
| 2010/0137860 A1 | 6/2010 | Demarais et al. |
| 2010/0152625 A1 | 6/2010 | Milo |
| 2010/0168624 A1 | 7/2010 | Sliwa |
| 2010/0168649 A1 | 7/2010 | Schwartz et al. |
| 2010/0191112 A1 | 7/2010 | Demarais et al. |
| 2010/0198040 A1 | 8/2010 | Friedman et al. |
| 2010/0210946 A1 | 8/2010 | Harada et al. |
| 2010/0222851 A1 | 9/2010 | Deem et al. |
| 2010/0228162 A1 | 9/2010 | Sliwa et al. |
| 2010/0331686 A1 | 12/2010 | Hossack et al. |
| 2010/0330951 A1 | 12/2010 | Strommer |
| 2011/0009779 A1 | 1/2011 | Romano et al. |
| 2011/0028962 A1 | 2/2011 | Werneth et al. |
| 2011/0034809 A1 | 2/2011 | Eberle et al. |
| 2011/0066217 A1 | 3/2011 | Diller et al. |
| 2011/0092781 A1 | 4/2011 | Gertner |
| 2011/0092880 A1 | 4/2011 | Gertner |
| 2011/0106132 A1 | 5/2011 | Barbut et al. |
| 2011/0112400 A1 | 5/2011 | Emery et al. |
| 2011/0178441 A1 | 7/2011 | Tyler |
| 2011/0201973 A1 | 8/2011 | Stephens et al. |
| 2011/0257563 A1 | 10/2011 | Thapliyal et al. |
| 2011/0264086 A1 | 10/2011 | Ingle |
| 2011/0270247 A1 | 11/2011 | Sherman |
| 2011/0282203 A1 | 11/2011 | Tsoref et al. |
| 2011/0282249 A1 | 11/2011 | Tsoref et al. |
| 2011/0319765 A1 | 12/2011 | Gertner et al. |
| 2012/0016273 A1 | 1/2012 | Diederich |
| 2012/0053577 A1 | 3/2012 | Lee et al. |
| 2012/0065494 A1 | 3/2012 | Gertner et al. |
| 2012/0095335 A1 | 4/2012 | Sverdlik et al. |
| 2012/0095371 A1 | 4/2012 | Sverdlik et al. |
| 2012/0095372 A1 | 4/2012 | Sverdlik et al. |
| 2012/0123270 A1 | 5/2012 | Klee et al. |
| 2012/0209116 A1 | 8/2012 | Hossack et al. |
| 2012/0215106 A1 | 8/2012 | Sverdlik et al. |
| 2012/0232409 A1 | 9/2012 | Stahmann et al. |
| 2012/0232436 A1 | 9/2012 | Warnking |
| 2012/0265227 A1 | 10/2012 | Sverdlik et al. |
| 2012/0268886 A1 | 10/2012 | Leontiev et al. |
| 2012/0283605 A1 | 11/2012 | Lewis, Jr. |
| 2012/0310233 A1 | 12/2012 | Dimmer et al. |
| 2012/0316559 A1 | 12/2012 | Mayse et al. |
| 2013/0072928 A1 | 3/2013 | Schaer |
| 2013/0131668 A1 | 5/2013 | Schaer |
| 2013/0197555 A1 | 8/2013 | Schaer |
| 2013/0204068 A1 | 8/2013 | Gnanashanmugam et al. |
| 2013/0204167 A1 | 8/2013 | Sverdlik et al. |
| 2013/0204242 A1 | 8/2013 | Sverdlik et al. |
| 2013/0207519 A1 | 8/2013 | Chaggares et al. |
| 2013/0211292 A1 | 8/2013 | Sverdlik et al. |
| 2013/0211396 A1 | 8/2013 | Sverdlik et al. |
| 2013/0211437 A1 | 8/2013 | Sverdlik et al. |
| 2013/0218054 A1 | 8/2013 | Sverdlik et al. |
| 2013/0218068 A1 | 8/2013 | Sverdlik et al. |
| 2013/0225595 A1 | 8/2013 | Gillies et al. |
| 2013/0267875 A1 | 10/2013 | Thapliyal et al. |
| 2013/0296836 A1 | 11/2013 | Barbut et al. |
| 2013/0310822 A1 | 11/2013 | Mayse et al. |
| 2014/0012133 A1 | 1/2014 | Sverdlik et al. |
| 2014/0039286 A1 | 2/2014 | Hoffer |
| 2014/0039477 A1 | 2/2014 | Sverdlik et al. |
| 2014/0074076 A1 | 3/2014 | Gertner |
| 2014/0088585 A1 | 3/2014 | Hill et al. |
| 2014/0180197 A1 | 6/2014 | Sverdlik et al. |
| 2014/0180277 A1 | 6/2014 | Chen |
| 2014/0194866 A1 | 7/2014 | Wang |
| 2014/0276135 A1 | 9/2014 | Agah et al. |
| 2014/0359111 A1 | 12/2014 | Hilmo et al. |
| 2015/0057599 A1 | 2/2015 | Chen |
| 2015/0112234 A1 | 4/2015 | McCaffrey et al. |
| 2015/0272668 A1 | 10/2015 | Chen |
| 2016/0059044 A1 | 3/2016 | Gertner |
| 2016/0113699 A1 | 4/2016 | Sverdlik et al. |
| 2016/0374710 A1 | 12/2016 | Sinelnikov et al. |
| 2017/0027645 A1 | 2/2017 | Ben Oren et al. |
| 2018/0326227 A1 | 11/2018 | Sverdlik et al. |

FOREIGN PATENT DOCUMENTS

| | | |
|---|---|---|
| CN | 101820820 | 9/2010 |
| EP | 1384445 | 1/2004 |
| EP | 1424100 | 6/2004 |
| EP | 1799302 | 3/2006 |
| EP | 1769759 | 4/2007 |
| EP | 1802370 | 7/2007 |
| EP | 2092957 | 8/2009 |
| EP | 2218479 | 8/2010 |
| EP | 2455133 | 5/2012 |
| JP | 07-227394 | 8/1995 |
| JP | 09-122139 | 5/1997 |
| JP | 10-248854 | 9/1998 |
| JP | 2008-536562 | 9/2008 |
| JP | 2010-517695 | 5/2010 |
| WO | WO 91/10405 | 7/1991 |
| WO | WO 99/16366 | 4/1999 |
| WO | WO 00/67648 | 10/2000 |
| WO | WO 01/45550 | 6/2001 |
| WO | WO 02/096501 | 12/2002 |
| WO | WO 2004/054448 | 7/2004 |
| WO | WO 2006/022790 | 3/2006 |
| WO | WO 2006/041847 | 4/2006 |
| WO | WO 2006/041881 | 4/2006 |
| WO | WO 2006/042163 | 4/2006 |
| WO | WO 2007/001981 | 1/2007 |

(56) References Cited

FOREIGN PATENT DOCUMENTS

| | | |
|---|---|---|
| WO | WO 2007/078997 | 7/2007 |
| WO | WO 2007/115307 | 10/2007 |
| WO | WO 2007/127176 | 11/2007 |
| WO | WO 2008/003058 | 1/2008 |
| WO | WO 2008/098101 | 8/2008 |
| WO | WO 2008/102363 | 8/2008 |
| WO | WO 2010/009473 | 1/2010 |
| WO | WO 2010/118307 | 10/2010 |
| WO | WO 2011/053757 | 5/2011 |
| WO | WO 2011/060200 | 5/2011 |
| WO | WO 2012/052920 | 4/2012 |
| WO | WO 2012/052921 | 4/2012 |
| WO | WO 2012/052922 | 4/2012 |
| WO | WO 2012/052924 | 4/2012 |
| WO | WO 2012/052925 | 4/2012 |
| WO | WO 2012/052926 | 4/2012 |
| WO | WO 2012/052927 | 4/2012 |
| WO | WO 2012/061713 | 5/2012 |
| WO | WO 2013/030743 | 3/2013 |
| WO | WO 2013/111136 | 8/2013 |
| WO | WO 2013/134479 | 9/2013 |
| WO | WO 2013/157009 | 10/2013 |
| WO | WO 2013/157011 | 10/2013 |
| WO | WO 2013/162694 | 10/2013 |
| WO | WO 2014/141052 | 9/2014 |
| WO | WO 2014/188430 | 11/2014 |
| WO | WO 2016/084081 | 6/2016 |
| WO | WO 2016/084081 A8 | 6/2017 |
| WO | WO 2018/173052 | 9/2018 |
| WO | WO 2018/173053 | 9/2018 |

OTHER PUBLICATIONS

Applicant-Initiated Interview Summary dated Jul. 14, 2016 From the US Patent and Trademark Office Re. U.S. Appl. No. 13/449,539.
Applicant-Initiated Interview Summary dated Jan. 21, 2015 From the US Patent and Trademark Office Re. U.S. Appl. No. 13/449,539.
Applicant-Initiated Interview Summary dated Feb. 22, 2016 From the US Patent and Trademark Office Re. U.S. Appl. No. 13/880,066.
Applicant-Initiated Interview Summary dated Jan. 24, 2014 From the US Patent and Trademark Office Re. U.S. Appl. No. 13/449,539.
Applicant-Initiated Interview Summary dated Sep. 28, 2016 From the US Patent and Trademark Office Re. U.S. Appl. No. 13/905,224.
Communication Pursuant to Article 94(3) EPC dated Nov. 4, 2014 From the European Patent Office Re. Application No. 11833950.6.
Communication Pursuant to Article 94(3) EPC dated Feb. 8, 2016 From the European Patent Office Re. Application No. 11833950.6.
Communication Pursuant to Article 94(3) EPC dated Apr. 10, 2015 From the European Patent Office Re. Application No. 11782222.1.
Communication Pursuant to Article 94(3) EPC dated Jun. 10, 2014 From the European Patent Office Re. Application No. 11782247 6.3.
Communication Pursuant to Article 94(3) EPC dated Jun. 10, 2014 From the European Patent Office Re. Application No. 11784782.2.
Communication Pursuant to Article 94(3) EPC dated Apr. 14, 2014 From the European Patent Office Re. Application No. 11782221.3.
Communication Pursuant to Article 94(3) EPC dated Jul. 20, 2016 From the European Patent Office Re. Application No. 11782221.3.
Communication Pursuant to Article 94(3) EPC dated Sep. 26, 2014 From the European Patent Office Re. Application No. 11782222.1.
Communication Pursuant to Article 94(3) EPC dated Jul. 27, 2016 From the European Patent Office Re. Application No. 11782222.1.
Communication Pursuant to Article 94(3) EPC dated Oct. 30, 2014 From the European Patent Office Re. Application No. 11782221.3.
Decision of Rejection dated Apr. 28, 2016 From the Japanese Patent Office Re. Application No. 2013-534435 and Its Machine Translation in English.
International Preliminary Report on Patentability dated May 2, 2013 From the International Bureau of WIPO Re. Application No. PCT/IB2011/054634.
International Preliminary Report on Patentability dated May 2, 2013 From the International Bureau of WIPO Re. Application No. PCT/IB2011/054635.
International Preliminary Report on Patentability dated May 2, 2013 From the International Bureau of WIPO Re. Application No. PCT/IB2011/054636.
International Preliminary Report on Patentability dated May 2, 2013 From the International Bureau of WIPO Re. Application No. PCT/IB2011/054638.
International Preliminary Report on Patentability dated May 2, 2013 From the International Bureau of WIPO Re. Application No. PCT/IB2011/054639.
International Preliminary Report on Patentability dated May 2, 2013 From the International Bureau of WIPO Re. Application No. PCT/IB2011/054640.
International Preliminary Report on Patentability dated May 2, 2013 From the International Bureau of WIPO Re. Application No. PCT/IB2011/054641.
International Preliminary Report on Patentability dated Dec. 3, 2015 From the International Bureau of WIPO Re. Application No. PCT/IL2014/050457.
International Preliminary Report on Patentability dated Aug. 7, 2014 From the International Bureau of WIPO Re. Application No. PCT/IL2013/050068.
International Preliminary Report on Patentability dated Jun. 8, 2017 From the International Bureau of WIPO Re. Application No. PCT/IL2015/051145. (16 Pages).
International Preliminary Report on Patentability dated Oct. 30, 2014 From the International Bureau of WIPO Re. Application No. PCT/IL2013/050339.
International Preliminary Report on Patentability dated Oct. 30, 2014 From the International Bureau of WIPO Re. Application No. PCT/IL2013/050341.
International Search Report and the Written Opinion dated May 2, 2016 From the International Searching Authority Re. Application No. PCT/IL2015/051145.
International Search Report and the Written Opinion dated Feb. 7, 2012 From the International Searching Authority Re. Application No. PCT/IB2011/054641.
International Search Report and the Written Opinion dated Oct. 11, 2013 From the International Searching Authority Re. Application No. PCT/IL2013/050341.
International Search Report and the Written Opinion dated Sep. 19, 2013 From the International Searching Authority Re. Application No. PCT/IL2013/050068.
International Search Report and the Written Opinion dated Nov. 20, 2014 From the International Searching Authority Re. Application No. PCT/IL2014/050457.
International Search Report and the Written Opinion dated Jun. 22, 2012 From the International Searching Authority Re. Application No. PCT/IB2011/054640.
International Search Report and the Written Opinion dated Jan. 23, 2012 From the International Searching Authority Re. Application No. PCT/IB2011/054635.
International Search Report and the Written Opinion dated Jan. 25, 2012 From the International Searching Authority Re. Application No. PCT/IB2011/054636.
International Search Report and the Written Opinion dated Jan. 27, 2012 From the International Searching Authority Re. Application No. PCT/IB2011/054634.
International Search Report and the Written Opinion dated Jan. 27, 2012 From the International Searching Authority Re. Application No. PCT/IB2011/054638.
International Search Report and the Written Opinion dated Oct. 29, 2013 From the International Searching Authority Re. Application No. PCT/IL2013/050339.
International Search Report and the Written Opinion dated Jan. 31, 2012 From the International Searching Authority Re. Application No. PCT/IB2011/054639.
Invitation Pursuant to Rule 137(4) EPC dated Apr. 4, 2014 From the European Patent Office Re. Application No. 11785792.0.
Invitation Pursuant to Rule 137(4) EPC dated Apr. 8, 2014 From the European Patent Office Re. Application No. 11782222.1.
Invitation Pursuant to Rule 137(4) EPC dated Apr. 10, 2014 From the European Patent Office Re. Application No. 11782476.3.

(56) References Cited

OTHER PUBLICATIONS

Invitation Pursuant to Rule 137(4) EPC dated Mar. 21, 2016 From the European Patent Office Re. Application No. 11782222.1.
Invitation to Pay Additional Fees dated Sep. 3, 2013 From the International Searching Authority Re. Application No. PCT/IL2013/050339.
Invitation to Pay Additional Fees dated Mar. 4, 2016 From the International Searching Authority Re. Application No. PCT/IL2015/051145.
Invitation to Pay Additional Fees dated Sep. 4, 2014 From the International Searching Authority Re. Application No. PCT/IL2014/050457.
Invitation to Pay Additional Fees dated Aug. 5, 2013 From the International Searching Authority Re. Application No. PCT/IL2013/050341.
Invitation to Pay Additional Fees dated Apr. 17, 2012 From the International Searching Authority Re. Application No. PCT/IB2011/054640.
Invitation to Pay Additional Fees dated Jul. 24, 2013 From the International Searching Authority Re. Application No. PCT/IL2013/050068.
Notice of Non-Compliant Amendment dated Sep. 23, 2015 From the US Patent and Trademark Office Re. U.S. Appl. No. 13/880,124.
Notice of Reason for Rejection dated Aug. 25, 2015 From the Japanese Patent Office Re. Application No. 2013-534435.
Notification of Office Action and Search Report dated Dec. 1, 2014 From The State Intellectual Property Office of the People's Republic of China Re. Application No. 201180060862.8.
Office Action dated Jul. 30, 2014 From The State Intellectual Property Office of the People's Republic of China Re. Application No. 201180060741.3 and Its Summary in English.
Official Action dated Jul. 2, 2015 From the US Patent and Trademark Office Re. U.S. Appl. No. 13/879,400.
Official Action dated Dec. 3, 2014 From the US Patent and Trademark Office Re. U.S. Appl. No. 13/462,956.
Official Action dated Jun. 3, 2016 From the US Patent and Trademark Office Re. U.S. Appl. No. 13/880,066.
Official Action dated Nov. 4, 2014 From the US Patent and Trademark Office Re. U.S. Appl. No. 13/879,400.
Official Action dated Aug. 5, 2015 From the US Patent and Trademark Office Re. U.S. Appl. No. 13/905,224.
Official Action dated Jan. 5, 2016 From the US Patent and Trademark Office Re. U.S. Appl. No. 13/880,124.
Official Action dated Jun. 5, 2015 From the US Patent and Trademark Office Re. U.S. Appl. No. 14/049,238.
Official Action dated Nov. 5, 2014 From the US Patent and Trademark Office Re. U.S. Appl. No. 13/049,022.
Official Action dated Feb. 6, 2015 From the US Patent and Trademark Office Re. U.S. Appl. No. 14/190,113.
Official Action dated Jan. 6, 2017 From the US Patent and Trademark Office Re. U.S. Appl. No. 14/190,113. (11 pages).
Official Action dated Oct. 7, 2014 From the US Patent and Trademark Office Re. U.S. Appl. No. 13/880,109.
Official Action dated May 8, 2013 From the US Patent and Trademark Office Re. U.S. Appl. No. 13/462,956.
Official Action dated Jun. 10, 2016 From the US Patent and Trademark Office Re. U.S. Appl. No. 14/190,113.
Official Action dated Mar. 10, 2016 From the US Patent and Trademark Office Re. U.S. Appl. No. 13/449,539.
Official Action dated Sep. 10, 2014 From the US Patent and Trademark Office Re. U.S. Appl. No. 14/049,238.
Official Action dated Sep. 11, 2015 From the US Patent and Trademark Office Re. U.S. Appl. No. 13/880,066.
Official Action dated Apr. 14, 2014 From the US Patent and Trademark Office Re. U.S. Appl. No. 13/879,400.
Official Action dated Aug. 14, 2015 From the US Patent and Trademark Office Re. U.S. Appl. No. 13/449,539.
Official Action dated Jul. 17, 2013 From the US Patent and Trademark Office Re. U.S. Appl. No. 13/049,013.
Official Action dated Nov. 17, 2017 From the US Patent and Trademark Office Re. U.S. Appl. No. 13/905,224. (19 pages).
Official Action dated Dec. 19, 2013 From the US Patent and Trademark Office Re. U.S. Appl. No. 13/049,022.
Official Action dated Mar. 20, 2014 From the US Patent and Trademark Office Re. U.S. Appl. No. 13/449,539.
Official Action dated Oct. 20, 2017 From the US Patent and Trademark Office Re. U.S. Appl. No. 14/190,113. (7 pages).
Official Action dated Apr. 23, 2014 From the US Patent and Trademark Office Re. U.S. Appl. No. 13/880,061.
Official Action dated Oct. 24, 2012 From the US Patent and Trademark Office Re. U.S. Appl. No. 13/049,013.
Official Action dated Sep. 25, 2013 From the US Patent and Trademark Office Re. U.S. Appl. No. 13/462,956.
Official Action dated Sep. 25, 2015 From the US Patent and Trademark Office Re. U.S. Appl. No. 14/190,113.
Official Action dated Jul. 26, 2016 From the US Patent and Trademark Office Re. U.S. Appl. No. 13/880,124.
Official Action dated Dec. 27, 2016 From the US Patent and Trademark Office Re. U.S. Appl. No. 13/449,539. (13 pages).
Official Action dated Apr. 29, 2016 From the US Patent and Trademark Office Re. U.S. Appl. No. 13/905,224.
Official Action dated Aug. 29, 2013 From the US Patent and Trademark Office Re. U.S. Appl. No. 13/449,539.
Official Action dated Jan. 29, 2013 From the US Patent and Trademark Office Re. U.S. Appl. No. 13/049,151.
Restriction Official Action dated Oct. 5, 2012 From the US Patent and Trademark Office Re. U.S. Appl. No. 13/049,151.
Restriction Official Action dated Jul. 7, 2014 From the US Patent and Trademark Office Re. U.S. Appl. No. 14/049,238.
Restriction Official Action dated Apr. 14, 2015 From the US Patent and Trademark Office Re. U.S. Appl. No. 13/880,124.
Restriction Official Action dated Nov. 17, 2014 From the US Patent and Trademark Office Re. U.S. Appl. No. 13/880,066.
Restriction Official Action dated Feb. 27, 2015 From the US Patent and Trademark Office Re. U.S. Appl. No. 13/905,224.
Restriction Official Action dated Mar. 27, 2015 From the US Patent and Trademark Office Re. U.S. Appl. No. 13/880,095.
Restriction Official Action dated Jun. 28, 2013 From the US Patent and Trademark Office Re. U.S. Appl. No. 13/449,539.
Restriction Official Action dated Aug. 30, 2012 From the US Patent and Trademark Office Re. U.S. Appl. No. 13/049,013.
Restriction Official Action dated Oct. 30, 2014 From the US Patent and Trademark Office Re. U.S. Appl. No. 13/880,083.
Search Report dated Jul. 17, 2014 From The State Intellectual Property Office of the People's Republic of China Re. Application No. 201180060741.3 and Its Machine Translation in English.
Supplementary European Search Report and the European Search Opinion dated Dec. 22, 2016 From the European Patent Office Re. Application No. 14801877.3. (9 Pages).
Supplementary European Search Report dated Mar. 12, 2014 From the European Patent Office Re. Application No. 11833950.6.
Translation Dated Mar. 12, 2015 of Notification of Office Action and Search Report dated Dec. 1, 2014 From The State Intellectual Property Office of the People's Republic of China Re. Application No. 201180060862.8.
Translation Dated Nov. 18, 2015 of Notice of Reason for Rejection dated Aug. 25, 2015 From the Japanese Patent Office Re. Application No. 2013-534435.
Ahmed et al. "Renal Sympathetic Denervation Using an Irrigated Radiofrequency Ablation Catheter for the Management of Drug-Resistant Hypertension", Journal of the American College of Cardiology: Cardiovascular Interventions, JACC, 5(7): 758-765, 2012.
Ali et al. "Signal Processing Overview of Ultrasound Systems for Medical Imaging", Texas Instruments White Paper, SPRAB12: 1-27, Nov. 2008.
Anonymus "Indication for and Results of Sympathectomy in Patients With Peripheral Vascular Disease", Lumbar Sympathectomy, Poster, 34 P., 2009.
Aoyama et al. "Comparison of Cryothermia and Radiofrequency Current in Safety and Efficacy of Catheter Ablation Within the

(56) References Cited

OTHER PUBLICATIONS

Canine Coronary Sinus Close to the Left Circumflex Coronary Artery", Journal of Cardiovascular Electrophysiology, 16: 1218-1226, Nov. 2005.
Atherton et al. "Micro-Anatomy of the Renal Sympathetic Nervous System: A Human Postmortem Histologic Study", Clinical Anatomy, p. 1-6, Oct. 4, 2011.
Bailey et al. "Cavitation Detection During Shock-Wave Lithotripsy", Ultrasound in Medicine and Biology, XP027605630, 31(9): 1245-1256, Sep. 1, 2005. Abstract, Fig.1, p. 1246, p. 1247, r-h Col., p. 1249, r-h Col.
Baker et al. "Operative Lumbar Sympathectomy for Severe Lower Limb Ischaemia: Still a Valuable Treatment Option", Annals of the Royal College of Surgeons of England, 76(1): 50-53, Jan. 1994.
Bambi et al. "Real-Time Digital Processing of Doppler Ultrasound Signals", IEEE International Conference on Acoustics, Speech, and Signal Processing, Proceedings, (ICASSP '05), (5): v/977-v/980, Mar. 23-23, 2005.
Bandyopadhyay et al. "Outcomes of Beta-Blocker Use in Pulmonary Arterial Hypertension: A Propensity-Matched Analysis", European Respiratory Journal, 46(3): 750-760, Published Online May 28, 2015.
Bharat et al. "Monitoring Stiffness Changes in Lesions After Radiofrequency Ablation at Different Temperatures and Durations of Ablation", Ultrasound in Medicine & Biology, 31(3): 415-422, 2005.
Bhatt et al. "A Controlled Trial of Renal Denervation for Resistant Hypertension", The New England Journal of Medicine, 270(15): 1393-1401, Published Online Mar. 29, 2014.
Blankestijn et al. "Renal Denervation: Potential Impact on Hypertension in Kidney Disease?", Nephrology, Dialysis, Transplantation, 26(9): 2732-2734, Apr. 19, 2011.
Brandt et al. "Effects of Renal Sympathetic Denervation on Arterial Stiffness and Central Hemodynamics in Patients With Resistant Hypertension", Journal of the American College of Cardiology, 60(19): 1956-1965, 2012.
Brandt et al. "Renal Sympathetic Denervation Reduces Left Ventricular Hypertrophy and Improves Cardiac Function in Patients With Resistant Hypertension", Journal of the American College of Cardiology, 59(10): 901-909, 2012.
Brasselet et al. "Effect of Local Heating on Restenosis and In-Stent Neointimal Hyperplasia in the Atherosclerotic Rabbit Model: A Dose-Ranging Study", European Heart Journal, 29: 402-412, 2008.
Brinton et al. "Externally Focused Ultrasound for Sympathetic Renal Denervation", WAVE I First-In-Man Study, Kona Medical Inc., PowerPoint Presentation, TCT 2012, 15 P., 2012.
Campese et al. "Renal Afferent Denervation Prevents the Progression of Renal Disease in the Renal Ablation Model of Chronic Renal Failure in the Rat", American Journal of Kidney Diseases, 26(5): 861-865, Nov. 1995. Abstract.
Campese et al. "Sympathetic Renal Innervation and Resistant Hypertension", International Journal of Hypertension, 2011(Art.ID 814354): 1-6, 2011.
Cardiosonic "Cardiosonic New Applications", Cardiosonic, p. 1-20, Mar. 2014.
Cardiosonic "Histological Map of Swine Pulmonary Arteries", Cardiosonic, Animal #223, Mar. 26, 2014.
Cardiosonic "Histological Map of Swine Pulmonary Arteries", Cardiosonic, Animal #234, Mar. 18, 2014.
Cardiosonic "Histological Map of Swine Pulmonary Arteries", Cardiosonic, Animal #234, Mar. 26, 2014.
Cardiosonic "Histopathology Report", Cardiosonic, 2 P., Dec. 26, 2013.
Cardiosonic "PA/Trachea—Feedback Provisional", Cardiosonic, 5 P, Jun. 9, 2014.
Cardiosonic "PAH Preliminary Development Meeting Minutes", Cardiosonic, 2 P., Mar. 23, 2014.
Chen et al. "Artery Denervation to Treat Pulmonary Arterial Hypertension. The Single-Center, Prospective, First-in-Man PADN-1 Study (First-in-Man Pulmonary Artery Denervation for Treatment of Pulmonary Artery Hypertension)", Journal of the American College of Cardiology, JACC, 62(12): 1092-1100, Sep. 17, 2013.
Chen et al. "Hemodynamic, Functional, and Clinical Responses to Pulmonary Artery Denervation in Patients With Pulmonary Arterial Hypertension of Different Causes: Phase II Results From the Pulmonary Artery Denervation-1 Study", Circulation: Cardiovascular Interventions, 8(11): e002837-1-e002837-10, Nov. 9, 2015.
Chen et al. "Percutaneous Pulmonary Artery Denervation Completely Abolishes Experimental Pulmonary Arterial Hypertension In Vivo", EuroIntervention, 9(2): 269-276, Jun. 22, 2013.
Ciarka et al. "Prognostic Significance of Sympathetic Nervous System Activation in Pulmonary Arterial Hypertension", American Journal of Respiratory and Critical Care Medicine, 181(11): 1269-1275, Published Online Mar. 1, 2010.
CIBIS-II Investigators and Committees "The Cardiac Insufficiency Bisoprolol Study II (CIBIS-II): A Randomised Trial", The Lancet, 353(9146): 9-13, Jan. 2, 1999.
Cohn et al. "A Comparison of Enalapril With Hydralazine-Isosorbide Dinitrate in the Treatment of Chronic Congestive Heart Failure", The New England Journal of Medicine, 325(5): 303-310, Aug. 1, 1991.
CONSENSUS Trial Study Group "Effects of Enalapril on Mortality in severe Congestive Heart Failure. Results of the Cooperative North Scandinavian Enalapril Survival Study (CONSENSUS)", The New England Journal of Medicine, 316(23): 1429-1435, Jun. 4, 1987.
Copty et al. "Localized Heating of Biological Media Using a 1-W Microwave Near-Field Probe", IEEE Transactions on Microwave Theory and Techniques, 52(8): 1957-1963, Aug. 2004.
Copty et al. "Low-Power Near-Field Microwave Applicator for Localized Heating of Soft Matter", Applied Physics Letters, 84(25): 5109-5111, Jun. 21, 2004.
Damianou et al. "Dependence of Ultrasonic Attenuation and Absorpteion in Dog Soft Tissues on Temperature and Thermal Dose", Journal of the Acoustical Society of America, 102(1): 628-634, Jul. 1997.
Davies et al. "First-in-Man Safety Evaluation of Renal Denervation for Chronic Systolic Heart Failure: Primary Outcome From Reach-Pilot Study", International Journal of Cardiology, 162: 189-192, 2013.
De Man et al. "Bisoprolol Delays Progression Towards Right Heart Failure in Experimental Pulmonary Hypertension", Circulation Heart Failure, 5(1): 97-105, Published Online Dec. 9, 2011.
De Man et al. "Neurohormonal Axis in Patients With Pulmonary Arterial Hypertension. Friend or Foe?", American Journal of Respiratory and Critical Care Medicine, 187(1): 14-19, Published Online Nov. 9, 2012.
Deneke et al. "Histopathology of Intraoperatively Induced Linear Radiofrequency Ablation Lesions in Patients With Chronic Atrial Fibrillation", European Heart Journal, 26: 1797-1803, 2005.
Dewhirst et al. "Basic Principles of Thermal Dosimetry and Thermal Thresholds for Tissue Damage From Hyperthermia", International Journal of Hyperthermia, 19(3): 267-294, May-Jun. 2003.
DiBona "Neural Control of Renal Function: Cardiovascular Implications", Hypertension, 13: 539-548, 1989.
DiBona "Neural Control of the Kidney: Past, Present, and Future", Hypertension, 41: 621-624, Dec. 16, 2002.
DiBona "Physiology in Perspective: The Wisdom of the Body. Neural Control of the Kidney", American Journal of Physiology, Regulatory, Integrative and Comparative Physiology, 289(3): R633-R641, Sep. 2005.
DiBona et al. "Differentiated Sympathetic Neural Control of the Kidney", American Journal of Physiology, 271: R84-R90, 1996.
DiBona et al. "Translational Medicine: the Antihypertensive Effect of Renal Denervation", American Journal of Physiology, Regulatory, Integrative and Comparative Physiology, 298(2): R245-R253, Feb. 2010.
Diederich et al. "Catheter-Based Ultrasound Applicators for Selective Thermal Ablation: Progress Towards MRI-Guided Applications in Prostate", International Journal of Hyperthermia, 20(7): 739-756, Nov. 2004.
Diederich et al. "Catheter-Based Ultrasound Devices and MR Thermal Monitoring for Conformal Prostate Thermal Therapy",

(56) References Cited

OTHER PUBLICATIONS

30th Annual International IEEE EMBS Conference, Vancouver, British Columbia, Canada, Aug. 20-24, 2008, p. 3664-3668, 2008.
Diederich et al. "Induction of Hyperthermia Using an Intracavitary Multielement Ultrasonic Applicator", IEEE Transactions on Biomedical Engineering, 36(4): 432-438, Apr. 1989.
Diederich et al. "Ultrasound Technology for Hyperthermia", Ultrasound in Medicine & Biology, 25(6): 871-887, 1999.
Donoho et al. "Stable Recovery of Sparse Overcomplete Representations in the Presence of Noise", IEEE Transactions on Information Theory, 52(1): 1-42, Jan. 2006.
Drake et al. "Problematic Anatomical Sites Around the Pulmonary Artery", Gray's Anatomy for Students, 9 P., 2004.
Esler "The 2009 Carl Ludwig Lecture: Pathophysiology of the Human Sympathetic Nervous System in Cardiovascular Diseases: the Transition From Mechanisms to Medical Management", Journal of Applied Physiology, 108: 227-237, 2010.
Esler et al. "Measurement of Total and Organ-Specific Norepinephrine Kinetics in Humans", American Journal of Physiology—Endocrinology Metabolism 10, 247(1/Pt.1): E21-E28, Jul. 1984.
Esler et al. "Renal Sympathetic Denervation for Treatment of Drug-Resistant Hypertension: One-Year Results From the Symplicity HTN-2 Randomized, Controlled Trial", Circulation, 126: 2976-2982, 2012.
Failla et al. "Sympathetic Tone Restrains Arterial Distensibility of Healthy and Atherosclerotic Subjects", Journal of Hypertension, 17: 1117-1123, 1999.
Fischell PeriVascular Renal Denervation (PVRD™), Ablative Solutions Inc., TransCatheter Therapeutics Meeting, Miami, FL, USA, Oct. 24, 2012, PowerPoint Presentation, 14 P., Oct. 2012.
Fort Wayne Metals "HHS Tube", Fort Wayne Metals Research Products Corporation, 2 P., 2009.
Fujikura et al. "Effects of Ultrasonic Exposure Parameters on Myocardial Lesions Induced by High-Intensity Focused Ultrasound", Journal of Ultrasound Medicine, 25: 1375-1386, 2006.
Galie et al. "2015 ESC/ERS Guidelines for the Diagnosis and Treatment of Pulonary Hypertension. The Joint Task Force for the Diagnosis and Treatment of Pulmonary Hypertension of the European Society of Cardiology (ESC) and the European Respiratory Society (ERS). Endorsed by: Association for European Paediatric and Congenital Cardiology (AEPC), International Society for Heart and Lung Transplantation (ISHLT)", European Heart Journal, 37(1): 67-119, Published Online Aug. 29, 2015.
Galie et al. "New Treatment Stategies for Pulmonary Arterial Hypertension. Hopes or Hypes?", Journal of the American College of Cardiology, 62(12): 1101-1102, Sep. 17, 2013.
Galie et al. "Updated Treatment Algorithm of Pulmonary Arterial Hypertension", Journal of the American College of Cardiology, 62(25/Suppl.D): D60-D72, 2013.
Gander et al. "Least-Squares Fitting of Circles and Ellipses", BIT Numerical Mathematics, 34(4): 558-578, Dec. 1994.
Giering et al. "Determination of the Specific Heat Capacity of Healthy and Tumorous Human Tissue", Thermochimica Acta, 251: 199-205, Mar. 1995.
Glazier et al. "Laser Balloon Angioplasty Combined With Local Intrcoronary Heparin Therapy: Immediate and Short-Term Follow-Up Results", American Heart Journal, 134: 266-273, 1997.
Goswami "Renal Denervation: A Percutaneous Therapy for HTN", Prairie Heart Institute, Synvacor, The VEINS: Venous Endovascular Interventions Strategies, Chicago, USA, 42 P., 2012.
Granada et al. "A Translational Overview for the Evaluation of Peri-Renal Denervation Technologies", Cardiovascular Research Foundation, Columbai University Medical Center, New York, USA, Alizee Pathology, 25 P., 2011.
Grassi et al. "Sympathetic Mechanisms, Organ Damage, and Antihypertensive Treatment", Current Hypertension Report, 13: 303-308, 2011.
Griffiths et al. "Thoraco-Lumbar Splanchnicectomy and Sympathectomy. Anaesthetic Procedure", Anaesthesia, 3(4): 134-146, Oct. 1948.
Grimson et al. "Total Thoracic and Partial to Total Lumbar Sympathectomy, Splanchnicectomy and Celiac Ganglionectomy for Hypertension", Annals of Surgery, 138(4): 532-547, Oct. 1953.
Heath et al. "The Structure of the Pulmonary Trunk at Different Ages and in Cases of Pulmonary Hypertension and Pulmonary Stenosis", The Journal of Pathology and Bacteriology, 77(2): 443-456, Apr. 1959.
Hering et al. "Renal Denervation in Moderate to Severe CKD", Journal of the American Society of Nephrology, 23: 1250-1257, 2012.
Hering et al. "Substantial Reduction in Single Sympathetic Nerve Firing After Renal Denervation in Patients With rRsistant Hypertension", Hypertension, 61: 1-14, Nov. 19, 2012.
Holdaas et al. "Modulation of Reflex Renal Vasoconstriction by Increased Endogenous Renal Prostaglandin Synthesis", The Journal of Pharmacology and Experimental Therapeutics, 232(3): 725-731, 1985.
Janssen et al. "Role of Afferent Renal Nerves in Spontaneous Hypertension in Rats", Hypertension, 13: 327-333, 1989.
Joner "Histopathological Characterization of Renal Arteries After Radiofrequency Catheter Based Sympathetic Denervation in a Healthy Porcine Model", Deutsches Herzzentrum M?nchen, Technische Universit?t M?nchen, PowerPoint Presentation, TCT 2012, 15 P., 2012.
Katholi "Renal Nerves in the Pathogenesis of Hypertension in Experimental Animals and Humans", American Journal of Physiology, 245: F1-F14, 1983.
Katholi et al. "Intrarenal Adenosine Produces Hypertension by Activating the Sympathetic Nervous System via the Renal Nerves in the Dog", Journal of Hypertension, 2: 349-359, 1984.
Katholi et al. "Renal Nerves in the Maintenance of Hypertension: A Potential Therapeutic Target", Current Hypertension Reports, 12(3): 196-204, Jun. 2010.
Kleinlogel et al. "A Gene-Fusion Strategy for Stoichiometric and Co-Localized Expression of Light-Gated Membrane Proteins", Nature Methods, 8(12): 1083-1091, Dec. 2011.
Kline et al. "Functional Reinnervation and Development of Supersensitivity to NE After Renal Denervation in Rats", American Journal of Physiology, 238: R353-R358, 1980.
Kolh "Carotid Denervation by Adventitial Stripping: A Promising Treatment of Carotid Sinus Syndrome?", European Journal of Vascular and Endovascular Surgery, 39(2): 153-154, Feb. 2010.
Krum et al. "Catheter-Based Renal Sympathetic Denervation for Resistant Hypertension: A Multicentre Safety and Proof-of-Principle Cohort Study", The Lancet, 373: 1275-1281, Apr. 11, 2009.
Krum et al. "Catheter-Based Renal Sympathetic Denervation for Resistant Hypertension: A Multicentre Safety and Proof-of-Principle Cohort Study", The Lancet, 373: 1275-1281, Mar. 30, 2009.
Kummer "Pulmonary Vascular Innervation and Its Role in Responses to Hypoxia: Size Matters!", Proceedings of the American Thoracic Society, 8(6): 471-476, Nov. 1, 2011.
Lafon "Miniature Devices for Minimally Invasive Thermal Ablation by High Intensity Ultrasound", Cargese Workshop 2009, University of Lyon, France, INSERM U556, Presentation, 39 P., 2009.
Lambert et al. "Redo of Percutaneous Renal Denervation in a Patient With Recurrent Resistant Hypertension After Primary Treatment Success", Catheterization and Cardiovascular Interventions, p. 1-11, 2012.
Lele "Effects of Focused Ultrasonic Radiation on Peripheral Nerve, With Observations on Local Heating", Experimental Neurology, 8: 47-83, 1963.
Lemoine et al. "Amputations and Sympathectomy in Peripheral Vascular Disease of the Lower Extremity. Experience With 180 Patients", Journal of the National Medical Association, 61(3): 219-221, May 1969.
Li et al. "Acoustic Proximity Ranging in the Presence of Secondary Echoes", IEEE Transactions on Instrumentation and Measurement, XP011102759, 52(5): 1593-1605, Oct. 1, 2003. p. 1593.
Lin et al. "Utility of the PlasmaKinetic™ Bipolar Forceps® for Control of the Renal Artery in a Porcine Model", JTUA, 14(3): 118-121, Sep. 2003.

(56) References Cited

OTHER PUBLICATIONS

Liu et al. "A Helical Microwave Antenna for Welding Plaque During Balloon Angioplasty", IEEE Transactions on Microwave Theory and Techniques, 44(10): 1819-1831, Oct. 1996.

Liu et al. "Pulmonary Artery Denervation Improves Pulmonary Arterial Hypertension Induced Right Ventricular Dysfunction by Modulating the Local Renin-Angiotensin-Aldosterone System", BMC Cardiovascular Disorders, 16(1): 192-1-192-10, Oct. 10, 2016.

Lopez et al. "Effects of Sympathetic Nerves on Collateral Vessels in the Limb of Atherosclerosis Primates", Atherosclerosis, 90: 183-188, 1991.

Mabin et al. "First Experience With Endovascular Ultrasound Renal Denervation for the Treatment of Resistant Hypertension", EuroIntervention, 8: 57-61, 2012.

Mahfoud et al. "Effect of Renal Sympathetic Denervation on Glucose Metabolism in Patients With Resistant Hypertension: A Pilot Study", Circulation, 123: 1940-1946, 2011.

Mahfoud et al. "Is There a Role for Renal Sympathetic Denervation in the Future Treatment of Resistant Hypertension?", Future Cardiology, 7(5): 591-594, 2011.

Mahfoud et al. "Renal Hemodynamics and Renal Function After Catheter-Based Renal Sympathetic Denervation in Patients With Resistant Hypertension", Hypertension, 60: 419-424, 2012.

Makris et al. "Resistant Hypertension Workup and Approach to Treatment", International Journal of Hypertension, 2011(Art. ID598694): 1-10, 2011.

Manasse et al. "Clinical Histopathology and Ultrstructural Analysis of Myocardium Following Microwave Energy Ablation", European Journal of Cardio-Thoracic Surgery, 23: 573-577, 2003.

Mangoni et al. "Effect of Sympathectomy on Mechanical Properties of Common Carotid and Femoral Arteries", Hypertension, 30: 1085-1088, 1997.

Martin et al. "Premise, Promise, and Potential Limitations of Invasive Devices to Treat Hypertension", Current Cardiology Reports, 13(1): 86-92, Feb. 2011.

Mazor "Efficacy of Renal Denervation Is Positively Impacted by Longitudinal Treatments", Vessix Vascular Inc., PowerPoint Presentation, TCT 2012, 20 P., 2012.

MERIT-HF Study Group "Effect of Metaprolol CR/XL in Chronic Heart Failure: Metoprolol CR/XL Randomised Intervention Trial in Congestive Heart Failure (MERIT-HF)", The Lancet, 353(9169): 2001-2007, Jun. 12, 1999.

Mogil et al. "Renal Innervation and Renin Activity in Salt Metabolism and Hypertension", American Journal of Physiology, 216(4): 693-697, Apr. 1969.

Moretti et al. "Beta Blocker for Patients With Pulmonary Arterial Hypertension: A Single Center Experience", International Journal of Cardiology, 184(1): 528-532, Available Online Feb. 24, 2015.

Mortensen et al. "Catheter-Based Renal Sympathetic Denervation Improves Central Hemodynamics and Arterial Stiffness: A Pilot Study", The Journal of Clinical Hypertension, 14(12): 861-870, Dec. 2012.

Nootens et al. "Neurohormonal Activation in Patients With Right Ventricular Failure From Pulmonary Hypertension: Relation to Hemodynamic Variables and Endothelin Levels", Journal of the American College of Cardiology, JACC, 26(7): 1581-1585, Dec. 1995.

Ohkubo et al. "Histological Findings After Angioplasty Using Conventional Balloon, Radiofrequency Thermal Balloon, and Stent for Experimental Aortic Coarctation", Pediatrics International, 46: 39-47, 2004.

Olafsson et al. "Ultrasound Current Source Density Imaging", IEEE Transactions on Biomedical Engineering, 55(7): 1840-1848, Jul. 2008.

Ong et al. "Successful Treatment of Resistant Hypertension With Percutaneous Renal Denervation Therapy", Heart, 98(23): 1754-1755, Dec. 2012.

Ormiston "OneShot (Covidien)", Maya Medical, Auckland, New Zealand, PowerPoint Presentation.

Ormiston et al. "First-in-Human Use of the OneShot™ Renal Denervation System From Covidien", EuroIntervention, 8: 1090-1094, 2013.

Packer et al. "Effect of Carvedilol on Survival in Severe Chronic Heart Failure", The New England Journal of Medicine, 344(22): 1651-1658, May 31, 2001.

Page et al. "The Effect of Renal Denervation on Patients Suffering From Nephritis", The Journal of Clinical Investigation, 14(4): 443-458, Jul. 1935.

Papademetriou et al. "Renal Sympathetic Denervation for the Treatment of Difficult-to-Control or Resistant Hypertension", International Journal of Hypertension, 2011(Art.ID196518): 1-8, Jan. 2011.

Para Tech Coating "Parylene Properties", Para Tech Coating Inc., 1 P., 2010.

Perros et al. "Nebivolol for Improving Endothelial Dysfunction, Pulmonary Vascular Remodeling, and Right Heart Function in Pulmonary Hypertension", Journal of the American College of Cardiology, JACC, 65(7): 668-680, Feb. 24, 2015.

Pokushalov et al. "A Randomized Comparison of Pulmonary Vein Isolation With Versus Without Concomitant Renal Artery Denervation in Patients With Refractory Symptomatic Atrial Fibrillation and Resistant Hypertension", Journal of the American College of Cardiology, 60(13): 1163-1170, 2012.

Prapa et al. "Histopathology of the Great Vessels in Patients With Pulmonary Arterial Hypertension in Association With Congenital Heart Disease: Large Pulmonary Arteries Matter Too", international Journal of Cardiology, 168: 2248-2254, Available Online Feb. 28, 2013.

Prochnau et al. "Catheter-Based Renal Denervation for Drug-Resistant Hypertension by Using a Standard Electrophysiology Catheter", EuroIntervention, 7: 1077-1080, 2012.

Prochnau et al. "Efficacy of Renal Denervation With a Standard EP Catheter in the 24-h Ambulatory Blood Pressure Monitoring—Long-Term Follow-Up", International Journal of Cardiology, 157(3): 447-448, Jun. 14, 2012.

Quinn "Pre-Eclampsia and Partial Uterine Denervation", Medical Hypotheses, 64(3): 449-454, 2005. Abstract.

Rappaport "Treating Cardiac Disease With Catheter-Based Tissue Heating", IEEE Microwave Magazine, p. 57-64, Mar. 2002.

Reddy "Sound Intervention", Mount Sinai School of Medicine, MSSM, Presentation, 19 P., 2012.

Roehl et al. "Comparison of 3 Methods to Induce Acute Pulmonary Hypertension in Pigs", Comparative Medicine, 59(3): 280-286, Jun. 2009.

Rothman "Fim Evaluation of a New, Multi-Electrode RF System for Renal Denervation (Medtronic)", Medtronic Inc., PowerPoint Presentation, 8 P., 2012.

Rothman et al. "Pulmonary Artery Denervation Reduces Pulmonary Artery Pressure and Induces Histological Changes in an Acute Porcine Model of Pulmonary Hypertension", Circulation: Cardiovascular Interventions, 8(11): e002569-1-e002569-7, Published Online Nov. 17, 2015.

Rousselle "Experimental Pathways for the Evaluation of Extrinsic Renal Nerve Distribution, Density, and Quantification (Swine Model)", Alizee Pathology in Collaboration With Jack Skirkball Center for Cardiovascular Research, TCT, 20 P., Nov. 8, 2011.

Rousselle "Renal Artery Dervation: Experimental Pathways for the Evaluation of Extrinsic Renal Nerve Distribution, Density, and Quantification (Swine Model)", Alizee Pathology, Cardiovascular Research Foundation, Nov. 8, 2011.

Sakakura et al. "Methodological Standardization for the Pre-Clinical Evaluation of Renal Sympathetic Denervation", JACC: Cardiovascular Interventions. 7(10): 1184-1193, Published Online Sep. 14, 2014.

Sangiorgi et al. "Histo-Morphometric Evaluation of 2D Characteristics and 3D Sympatetic Renal Nerve Distribution in Hypertensive Vs. Normotensive Patients", Department of Pathology, Department of Cardiology, University of Rome Tor Vergata, Department of Cardiology University of Modena and Reggio Emilia, Medtronic Cardiovascular, PowerPoint Presentation, TCT 2012, 22 P., 2012.

Sanni et al. "Is Sympathectomy of Benefit in Critical Leg Ischaemia Not Amenable to Revascularisation?", Interactive CardioVascular and Thoracic Surgery, 4: 478-483, 2005.

(56) References Cited

OTHER PUBLICATIONS

Scheinert "Cardiosonic TIVUS™ Technology: An Intra-Vascular Ultrasonic Catheter for Targeted Renal Denervation", Center for Vascular Medicine, Park Hospital Leipzig, Germany, PowerPoint Presentation, TCT 2012, 16 P., 2012.
Schelegle et al. "Vagal Afferents Contribute to Exacerbates Airway Responses Following Ozone and Allergen Challenge", Respiratory Physiology & Neurobiology, 181(3): 277-285, May 31, 2012.
Schlaich "Long-Term Follow Up of Catheter-Based Renal Denervation for Resistant Hypertension Confirms Durable Blood Pressure Reduction", Hypertension & Kidney Disease Laboratory, Baker IDI Heart & Diabetes Institute, Melbourne VIC, Australia, PowerPoint Presentation, TCT 2012, 22 P., 2012.
Schlaich et al. "Renal Sympathetic-Nerve Ablation for Uncontrolled Hypertension", New England Journal of Medicine, 361(9): 932-934, Aug. 27, 2009.
Schnyder et al. "Common Femoral Artery Anatomy Is Influenced by Demographics and Comorbidity: Implications for Cardiac and Peripherial Invasive Studies", Catheterization and Cardiovascular Interventions, 53(3): 289-295, Jul. 2001.
Schwartz "Strategies to Model Efficacy of Hypertension Devices", EuroPCR 2013, The Leading Cardiovascular Course, 24 P., 2013.
Shelton Jr. et al. "A Nondestructive Technique to Measure Pulmonary Artery Diameter and Its Pulsatile Variations", Journal of Applied Physiology, 33(4): 542-544, Oct. 1972.
Shung "Doppler Flow Measurements", Diagnostic Ultrasound—Imaging and Blood Flow Measurements, Chap.5:103-104, 2006.
Sievert et al. "Catheter-Based Technology Alternatives for Renal Denervation", CardioVascular Center Frankfurt, Germany, TCT 2012, Miami, FL, USA, Oct. 22-26, 2012, PowerPoint Presentation, 35 P., Oct. 2012.
Simonneau et al. "Updated Clinical Classification of Pulmonary Hypertension", Journal of the American College of Cardiology, 54(1/Suppl.S): S43-S54, Jun. 30, 2009.
Sitbon et al. "Beyond a Single Pathway: Combination Therapy in Pulmonary Arterial Hypertension", European Respiratory Review, 25(142): 408-417, Dec. 2016.
SOLVD Investigators "Effect of Enalapril on Survival in Patients With Reduced Left Ventricular Ejection Fractions and Congestive Heart Failure", The New England Journal of Medicine, 325(5): 293-302, Aug. 1, 1991.
Souchon et al. "Monitoring the Formation of Thermal Lesions With Heat-Induced Echo-Strain Imaging: A Feasibility Study", Ultrasound in Medicine & Biology, 31(2): 251-259, 2005.
Stefanadis "Vincristine Local Delivery for Renal Artery Denervation", Athens, Greece, PowerPoint Presentation, TCT 2012, 21 P., 2012.
Steigerwald et al. "Morphological Assessment of Renal Arteries After Radiofrequency Catheter-Based Sympathetic Denervation in a Porcine Model", Journal of Hypertension, 30(11): 2230-2239, Nov. 2012.
Swierblewska et al. "An Independent Relationship Between Muscle Sympathetic Nerve Activity and Pulse Wave Velocity in Normal Humans", Journal of Hypertension, 28: 979-984, 2010.
Symplicity HTN-1 Investigators "Catheter-Based Renal Sympathetic Denervation for Resistant Hypertension: Durability of Blood Pressure Reduction Out to 24 Months", Hypertension, 57: 911-917, Mar. 14, 2011.
Symplicity HTN-2 Investigators "Renal Sympathetic Denervation in Patients With Treatment-Resistant Hypertension (The Symplicity HTN-2 Trial): A Randomised Controlled Trial", The Lancet, 376(9756): 1903-1909, Published Online Nov. 17, 2010.
Symplicity HTN-2 Investigators "Renal Sympathetic Denervation in Patients With Treatment-Resistant Hypertension (The Symplicity HTN-2 Trial): A Randomised Controlled Trial", The Lancet, 376: 1903-1909, Dec. 4, 2010.
Szabo "Diagnostic Ultrasound Imaging: Inside Out", Academic Press Series in Biomedical Engineering, 2004. Book: Diagnostic Ultrasound Imaging Inside Out—Bronzino ; Academic Press Series in Biomedical Engineering ,Joseph Bronzino, Series Editor ; Trinity College—Hartford, Connecticut "Diagnostic Ultrasound Imaging Inside Out", Academic Press Series in Biomedical Engineering, 2004.
Techavipoo et al. "Temperature Dependence of Ultrasonic Propagation Speed and Attenuation in Excised Canine Liver Tissue Measured Using Transmitted and Reflected Pulses", Journal of the Acoustical Society of America, 115(6): 2859-2865, Jun. 2004.
Thenappan et al. "Beta-Blocker Therapy Is Not Associated With Adverse Outcomes in Patients With Pulmonary Arterial Hypertension. A Propensity Score Analysis", Circulation Heart Failure, 7(6): 903-910, Published Online Oct. 2, 2014.
Tibshirani "Regression Shrinkage and Selction via the Lasso: A Retrospective", Journal of the Royal Statistical Society, Series B: Statistical Methodology, 73(Pt.3): 273-282, 2011.
Tibshirani "Regression Shrinkage and Selection Via the Lasso", Journal of the Royal Statistical Society, Series B: Methodological, 58(1): 267-288, 1996.
Toorop et al. "Clinical Results of Carotid Denervation by Adventitial Stripping in Caotid Sinus Syndrome", Europan Journal of Vascular and Endovascular Syndrome, 39: 146-152, 2010.
Tyreus et al. "Two-Dimensional Acoustic Attenuation Mapping of High-Temperature Interstitial Ultrasound Lesions", Physics in Medicine and Biology, 49: 533-546, 2004.
Van Albada et al. "Biological Serum Markers in the Managment of Pediatric Pulmonary Arterial Hypertension", Pediatric Research, 63(3): 321-327, Mar. 2008.
Velez-Roa et al. "Increased Sympathetic Nerve Activity in Pulmonary Artery Hypertension", Circulation, 110(10): 1308-1312, Sep. 7, 2004.
Verloop et al. "The Effects of Renal Denervation on Renal Haemodynamics", Interventions for Hypertenison & Heart Failure, Abstracts of EuroPCR & AsiaPCR/SingLIVE 2013, May 21, 2013.
Virmani "Translation Medicine and Renal Denervation: Pre-Clinical Animal Models and Histoanatomy", CVPath Institute, Gaithersburg, MD, USA, PowerPoint Presentation.
Voskuil et al. "Percutaneous Renal Denervation for the Treatment of Resistant Essential Hypertension; The First Dutch Experience", Netherlands Heart Journal, 19(7-8): 319-323, Aug. 2011.
Warwick et al. "Trackless Lesions in Nervous Tissues Produced by High Intensity Focused Ultrsound (High-Frequency Mechanical Waves)", Journal of Anatomy, 102(3): 387-405, 1968.
Wikswo Jr. et al. "Magnetic Field of a Nerve Impulse: First Measurements", Science, 208: 53-55, Apr. 4, 1980.
Wilcox "Resistant Hypertension and the Role of the Sympathetic Nervous System", Medtronic, 30 P.
Williams et al. "Laser Energy Source in Surgical Atrial Fibrillation Ablation: Preclinical Experience", The Annals of Thoracic Surgery, 82: 2260-2264, 2006.
Witkowski "Future Perspective in Renal Denervation: Congestive Heart Failure, Insulin Resistance and Sleep Apnea", Innovations in Cardiovascular Interventions, ICI Meeting 2011, Tel Aviv, Israel, Dec. 4-6, 2011, 23 P., 2011.
Witkowski et al. "Effects of Renal Sympathetic Denervation on Blood Pressure, Sleep Apnea Course, and Glycemic Control in Patients With Resistant Hypertension and Sleep Apnea", Hypertension, 58(4): 559-565, Oct. 2011.
Witkowski et al. "Effects of Renal Sympathetic Denervation on Blood Pressure, Sleep Apnea Course, and Glycemic Control in Patients With Resistant Hypertension and Sleep Apnea", Hypertension, 58: 559-565, Aug. 15, 2011.
Witte et al. "Imaging Current Flow in Lobster Nerve Cord Using the Acoustoelectric Effect", Applied Physics Letters, 90: 163902-1-163902-3, 2007.
Wolf-De Jonge et al. "25 Years of Laser Assisted Vascular Anastomosis (LAVA): What Have We Learned?", European Journal of Vascular and Endovascular Surgery, 27(5): 466-476, May 2004.
Worthington et al. "Changes in Ultrasound Properties of Porcine Kidney Tissue During Heating", Ultrasound in Medicine & Biology, 27(5): 673-682, 2001.
Worthington et al. "Ultrasound Properties of Human Prostate Tissue During Heating", Ultrsound in Medicine & Biology, 28(10): 1311-1318, 2002.

(56) References Cited

OTHER PUBLICATIONS

Wright "On a Relationship Between the Arrhenius Parameters From Thermal Damage Studies", Transactions of the ASME, Technical Brief, Journal of Biomechanical Engineering, 125(2): 300-304, Apr. 9, 2003.
Wu et al. "A Quality Control Program for MR-Guided Focused Ultrasound Ablation Therapy", Journal of Applied Clinical Medical Physics, 3(2): 162-167, Spring 2002.
Wu et al. "Noninvasive Cardiac Arrhythmia Therapy Using High-Intensity Focused Ultrasound (HIFU) Ablation", International Journal of Cardiology, 166(2): e28-e30, Available Online Feb. 26, 2013.
Xu et al. "Experimental Nerve Thermal Injury", Brain, 117: 375-384, 1994.
Zeller "Percutaneous Renal Denervation System. The New Ultrasound Solution for the Mangament of Hypertension", Paradise Ultrasound Denervation System, ReCor Medical, 27 P., 2013.
Zhou et al. "Pulmonary Artery Denervation Attenuates Pulmonary Arterial Remodeling in Dogs With Pulmonary Arterial Hypertension Induced by Dehydrogenized Monocrotaline", JACC: Cardiovascular Interventions, 8(15): 2013-2023, Dec. 28, 2015.
Advisory Action Before the Filing of an Appeal Brief dated Feb. 4, 2019 From the US Patent and Trademark Office Re. U.S. Appl. No. 14/190,113. (6 pages).
Applicant-Initiated Interview Summary dated Nov. 14, 2018 From the US Patent and Trademark Office Re. U.S. Appl. No. 13/449,539. (3 pages).
Communication Pursuant to Rule 164(1) EPC: Supplementary Partial European Search Report and the European Provisional Opinion dated May 18, 2018 From the European Patent Office Re. Application No. 15862313.2. (15 Pages).
International Search Report and the Written Opinion dated Aug. 28, 2018 From the International Searching Authority Re. Application No. PCT/IL2018/050322. (40 Pages).
International Search Report and the Written Opinion dated Aug. 29, 2018 From the International Searching Authority Re. Application No. PCT/IL2018/050321. (16 Pages).
Invitation to Pay Additional Fees dated Jun. 21, 2018 From the International Searching Authority Re. Application No. PCT/IL2018/050322. (3 Pages).
Invitation to Pay Additional Fees dated Jun. 25, 2018 From the International Searching Authority Re. Application No. PCT/IL2018/050321. (2 Pages).
Official Action dated Aug. 10, 2018 From the US Patent and Trademark Office Re. U.S. Appl. No. 14/190,113. (11 pages).
Official Action dated Jun. 21, 2018 From the US Patent and Trademark Office Re. U.S. Appl. No. 13/449,539. (8 pages).
Official Action dated Oct. 31, 2018 From the US Patent and Trademark Office Re. U.S. Appl. No. 13/905,224. (23 pages).
Restriction Official Action dated Jan. 4, 2019From the US Patent and Trademark Office Re. U.S. Appl. No. 15/529,137. (8 pages).
Restriction Official Action dated May 24, 2018 From the US Patent and Trademark Office Re. U.S. Appl. No. 14/889,890. (8 pages).
Supplementary European Search Report and the European Search Opinion dated Sep. 5, 2018 From the European Patent Office Re. Application No. 15862313.2. (13 Pages).
Van Campen et al. "Bisoprolol in Idiopathic Pulmonary Arterial Hypertension: an Explorative Study", European Respiratory Journal, 48: 787-796, 2016.

\* cited by examiner

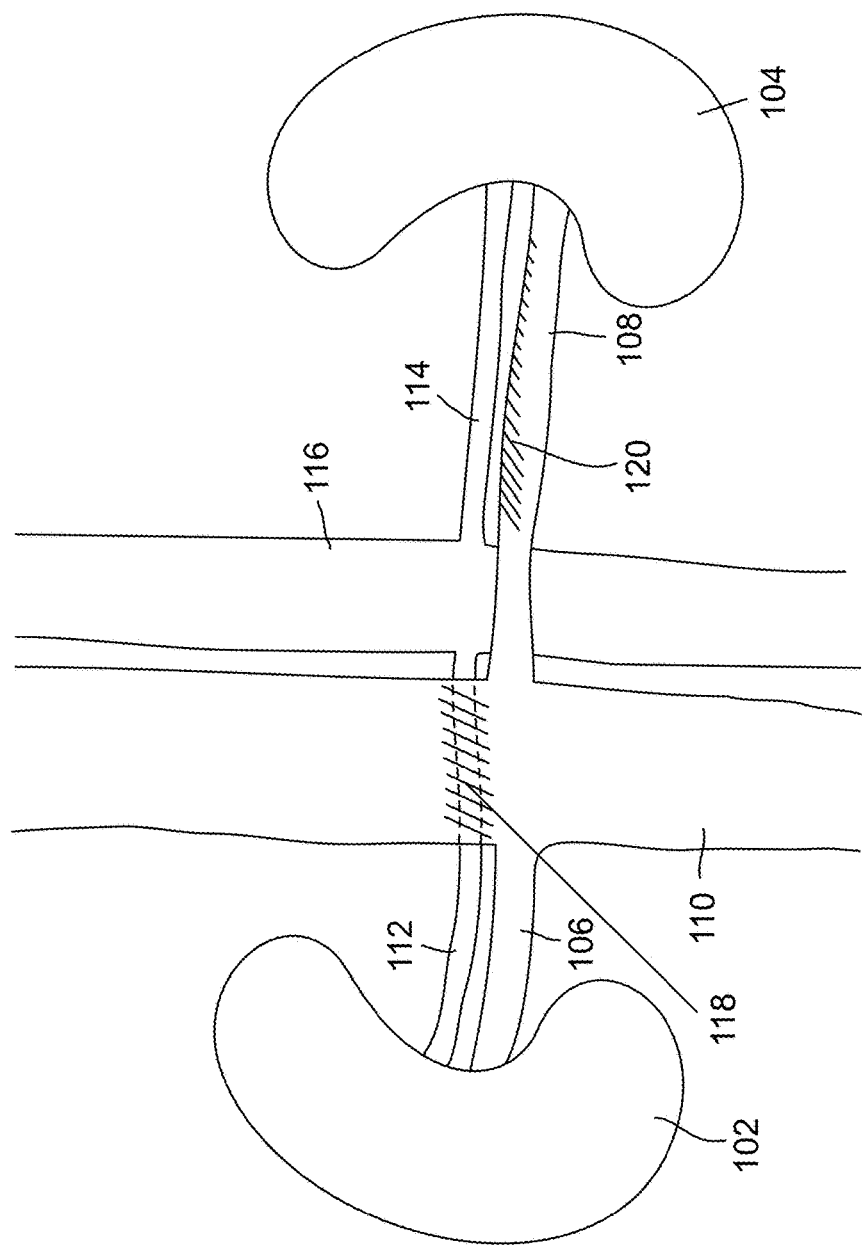

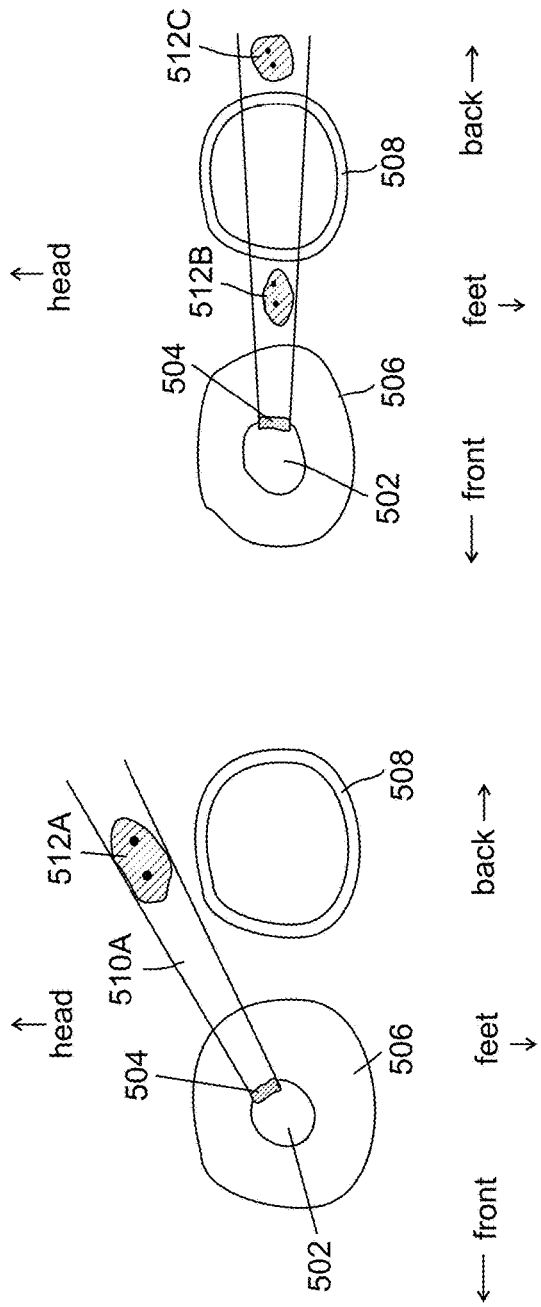
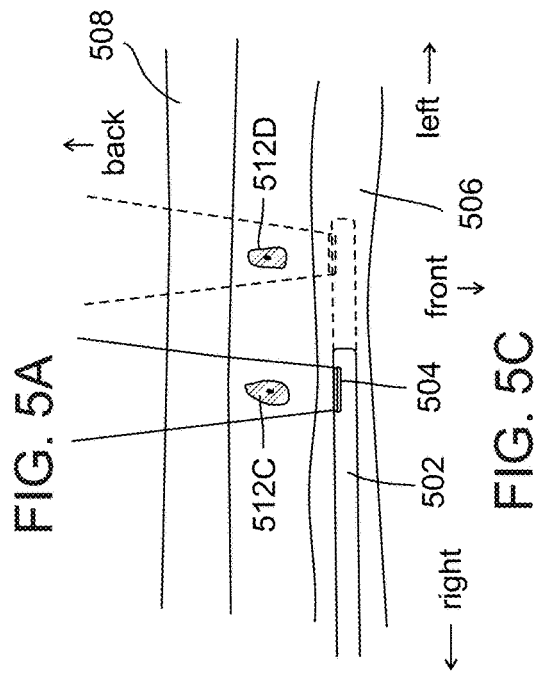

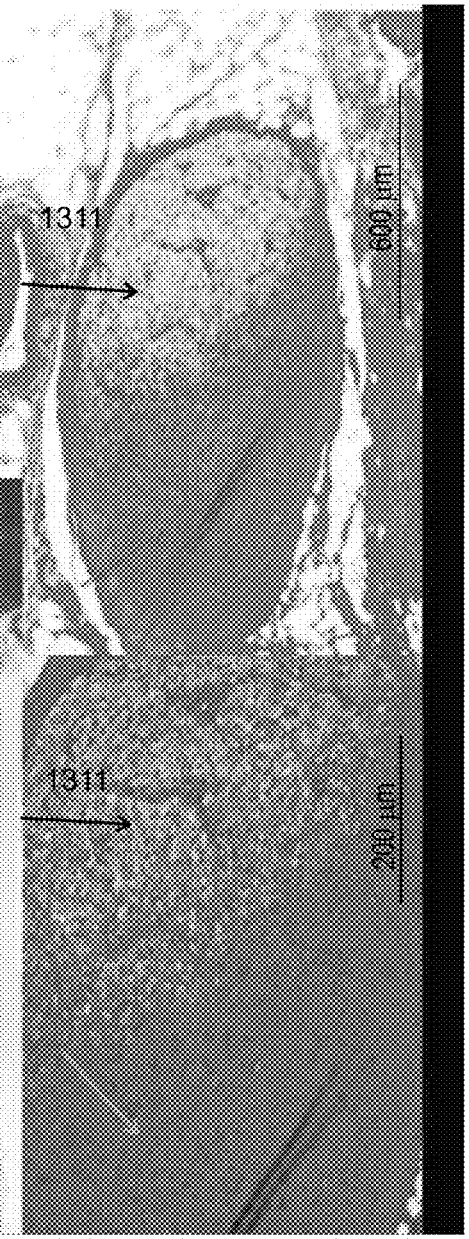

Damage to nerves adjacent to the carotid artery

Damage border marked with solid blue line. A: Localized effect. B: Remote effect (Can reach nearby nerve bundle)
Note: No damage in the intima although there is clear damage in the media

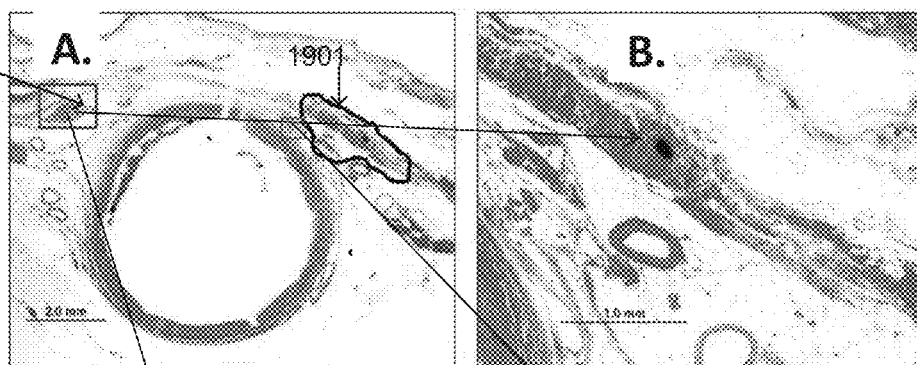
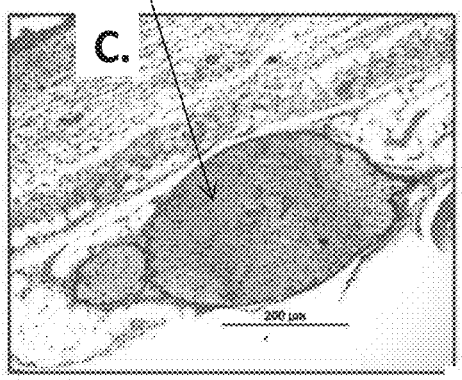
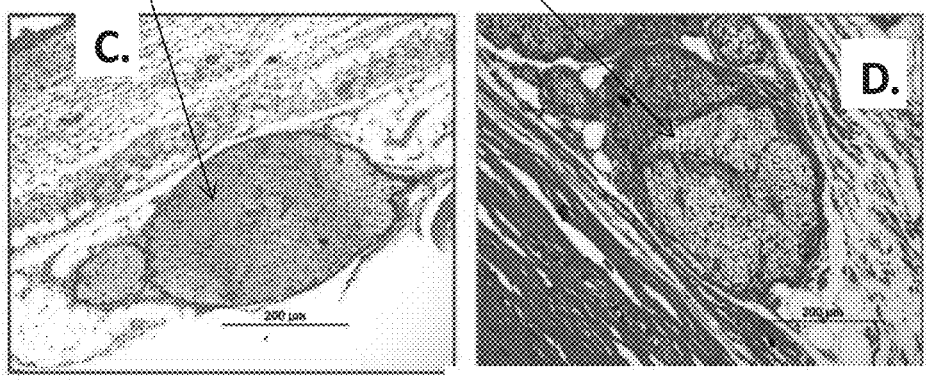
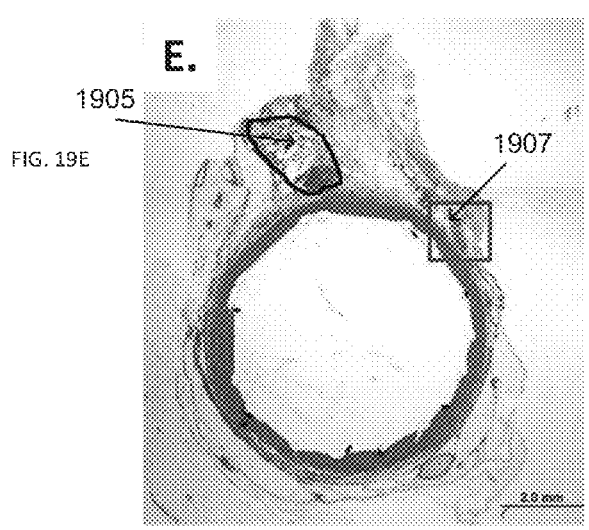
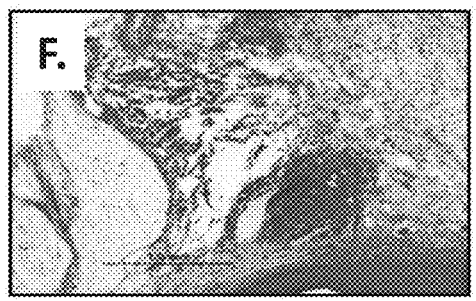
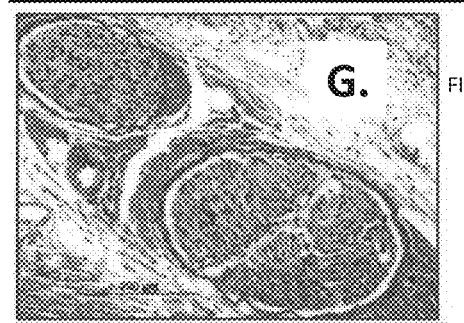
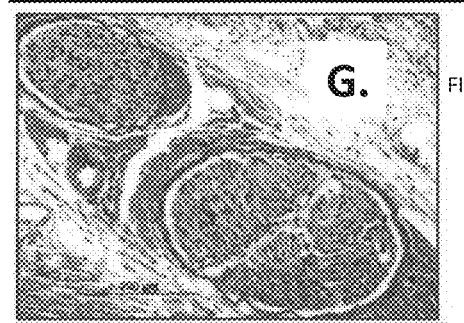

TISSUE TREATMENT

RELATED APPLICATIONS

This application is a National Phase of PCT Patent Application No. PCT/IL2013/050341 having International filing date of Apr. 18, 2013, which claims the benefit of priority under 35 USC § 119(e) of U.S. Provisional Patent Application No. 61/625,810 filed on Apr. 18, 2012. The contents of the above applications are all incorporated by reference as if fully set forth herein in their entirety.

FIELD AND BACKGROUND OF THE INVENTION

The present invention, in some embodiments thereof, relates to a method of tissue treatment and, more particularly, but not exclusively, to a method of selectively applying energy to treat tissues.

R. J. Toorop et al. "Clinical Results of Carotid Denervation by Adventitial Stripping in Carotid Sinus Syndrome", Eur J Vasc Endovasc Surg (2010) 39, 146-152 disclose "Carotid denervation by adventitial stripping of the proximal carotid internal artery is effective and safe and may offer a valid alternative for pacemaker treatment in patients with carotid sinus syndrome."

Sanni et al. "Is sympathectomy of benefit in critical leg ischaemia not amendable to revascularization?", Interactive CardioVascular and Thoracic Surgery 4 (2005) 478-483 disclose "Lumbar sympathectomy should be considered for symptomatic patients with critical leg ischaemia as an alternative to amputation."

M. P. Schlaich et al. "Renal denervation as a therapeutic approach for hypertension: novel implications for an old concept", Hypertension (2009) 54(6):1195-201.

E. Manasse et al. "Clinical histopathology and ultrastructural analysis of myocardium following microwave energy ablation", European Journal of Cardio-thoracic Surgery 23 (2003) 573-577.

SUMMARY OF THE INVENTION

An aspect of some embodiments of the invention relates to forming regions of tissue damage (e.g., thermal damage) by delivery of energy from within a vessel or lumen or cavity.

In an exemplary embodiment of the invention, the tissue damage regions are formed near a first lumen by application of energy from a second lumen.

In an exemplary embodiment of the invention, energy is applied from within a stenotic lumen (e.g., due to a plaque), to treat tissues in the wall of the stenotic lumen.

In an exemplary embodiment of the invention, the lumen contains a deployed stent, and energy is applied from within the lumen to treat tissues in the wall of the stented lumen.

In an exemplary embodiment of the invention, the energy is applied to several angles of the lumen circumference simultaneously. In an exemplary embodiment of the invention, energy is delivered from a heart chamber to treat the heart wall.

In an exemplary embodiment of the invention, energy is delivered from a heart chamber to treat a pulmonary vein.

In an exemplary embodiment of the invention, energy is delivered from a carotid artery to treat nerves in and/or near the carotid artery wall and/or near the carotid body.

There is provided in accordance with an exemplary embodiment of the invention a method of treating tissue near a first lumen comprising:

Inserting one or more energy emission elements into a second lumen;

delivering energy in an amount sufficient to cause one or more spaced apart areas, located longitudinally and/or circumferentially along the vessel, of tissue damage at preselected locations in tissue near the first lumen, the energy is delivered in less than about 180 seconds per area.

Alternatively, said energy is delivered in less than about 60 seconds per said area, for example less than about 40 seconds per area. Alternatively, said energy is delivered in less than about 30 seconds per said area.

In an exemplary embodiment of the invention, the second lumen is selected from the group comprising: inferior vena cava, left renal vein, right renal vein, left ureter, right ureter, left renal pelvis, right renal pelvis, right femoral vein, left femoral vein.

In an exemplary embodiment of the invention, the first lumen is selected from the group comprising: right renal artery, left renal artery, right femoral artery, left femoral artery.

In an exemplary embodiment of the invention, the energy comprises a pencil beam of unfocused ultrasound energy.

In an exemplary embodiment of the invention, the energy comprises several pencil beams of unfocused ultrasound energy emitted circumferentially, optionally passing from a first lumen to a second lumen.

In an exemplary embodiment of the invention, the one or more areas are formed about 0.5-10 mm, such as 7 mm, 2 mm, 1 mm from an intima of the first lumen. Optionally or additionally, the one or more areas are formed about 1-5 mm from the second lumen.

In an exemplary embodiment of the invention, the one or more areas are not formed between the first lumen and the second lumen.

In an exemplary embodiment of the invention, the one or more areas are formed on the side of the first lumen opposite the second lumen.

In an exemplary embodiment of the invention, the one or more areas cover about 20% to about 70% of a circumference of the first lumen.

In an exemplary embodiment of the invention, each of the one or more areas covers a sector of the first lumen of about 15 to 45 degrees.

In an exemplary embodiment of the invention, the method further comprises propping open the first lumen and/or the second lumen using a distancing and/or expandable device.

In an exemplary embodiment of the invention, the expandable device may be unidirectional or multidirectional.

There is provided in accordance with an exemplary embodiment of the invention an expandable device for insertion in a lumen comprising;

an expanding structure for insertion into the lumen using a vascular approach, the expanding structure does not lie between a beam source inserted therethrough and a wall of the lumen and/or lies between a beam source and a wall of the lumen.

In an exemplary embodiment of the invention, the expanding structure is sized to provide a clearance between the beam source and the wall so that blood flowing in the clearance selectively cools the wall.

In an exemplary embodiment of the invention, the lumen comprises a vein, and the expanding structure is sized to provide a clearance between the beam source and the wall so that blood flowing in the clearance selectively cools the beam source so that the blood temperature remains below a safe level.

In an exemplary embodiment of the invention, the lumen comprises a vein, and the expanding device does not exert a force sufficient to damage walls of the vein.

In an exemplary embodiment of the invention, an expanded state has a diameter that allows a distance of at least 1.0 mm between the beam source and the lumen wall.

There is provided in accordance with an exemplary embodiment of the invention a device for insertion into a second lumen for delivering energy to treat tissue near a first lumen, the device comprising:

a catheter sized to fit into the second lumen;
an energy emission element disposed on a distal end of the catheter, the energy emission element adapted to transmit energy with parameters to damage tissue near the first lumen; Optionally, the energy emission element transmits energy in multiple axial positions. Optionally, the energy emission element transmits energy in several angles, for example covering a total of 40 degrees circumferentially.
a controller to control the energy emission element, the controller programmed to supply energy for a time period ranging from about 5 to 180 seconds, at a frequency of about 5 MHz to 40 MHz, at an intensity of about 10 Watt/cm^2 to 60 Watt/cm^2, the energy setting sufficient to selectively damage tissue near the second lumen.

In an exemplary embodiment of the invention, near the second lumen comprises between 0 and 359 degrees around a circumference of the second lumen.

In an exemplary embodiment of the invention, the energy emission element is an ultrasound emission element adapted to form a pencil beam of unfocused ultrasound energy.

In an exemplary embodiment of the invention, the controller is programmed to control the energy emission element to transmit energy for a period of about 5 seconds to about 60 seconds. Optionally or additionally, the controller is programmed to control the energy emission element to transmit energy having an intensity of about 20 Watt/cm^2 to 40 Watt/cm^2.

There is provided in accordance with an exemplary embodiment of the invention a method of treating a patient suffering from abnormal carotid sinus receptors comprising:
selectively applying energy at least to a perivascular tissue of a carotid sinus in an amount sufficient to decrease signal propagation from a carotid sinus nerve and/or carotid body to a brain of the patient thereby treating the patient.

In an exemplary embodiment of the invention, the selectively applying comprises selectively applying in an alternating pattern of spaced apart damage areas in a radial direction along a carotid artery.

In an exemplary embodiment of the invention, the decreases signal propagation comprises decrease at least 50% of the signals propagating from the carotid sinus nerve towards a brain.

In an exemplary embodiment of the invention, the energy comprises a beam of unfocused ultrasound.

In an exemplary embodiment of the invention, the selectively applying comprises an energy intensity setting for treatment of renal nerves reduced by about 5%-20%.

There is provided in accordance with an exemplary embodiment of the invention a device for treating a carotid artery wall comprising:

a catheter sized to fit into the carotid artery;
an energy emission element disposed on a distal end of the catheter, the energy emission element adapted to transmit energy with an intensity sufficient to damage tissue around a circumference of the carotid artery;
a controller to control the energy emission element, the controller programmed to supply sufficient power at setting sufficient to thermally damage perivascular tissue around the carotid artery wall so that signals from carotid sinus receptors are selectively decreased, wherein one or both of an energy intensity and a treatment time are about 10%-50% higher than the highest allowable settings for a renal artery to treat locations at a similar distance from an inner wall.

In an exemplary embodiment of the invention, selectively decrease comprises selectively decrease by at least 50%. Optionally, the signals are selectively decreased when a higher energy intensity is applied.

In an exemplary embodiment of the invention, a frequency of the energy is selected according to frequencies allowable in a renal artery to treat locations at a similar distance from an inner wall.

In an exemplary embodiment of the invention, the energy emission element comprises an ultrasound emission element producing a beam of unfocused ultrasound.

There is provided in accordance with an exemplary embodiment of the invention a method of treating a patient suffering from insufficient blood flow to a limb comprising:
inserting a catheter including an energy emission element into a stenotic lumen;
selectively applying energy from within the lumen across a plaque to form one or more spaced apart regions of thermal damage in a surrounding tissue of the lumen, the tissue including nerves, thereby increasing blood flow to the limb.

In an exemplary embodiment of the invention, selectively applying comprises selectively applying energy from within the lumen across a calcified lumen wall.

In an exemplary embodiment of the invention, selectively applying comprises applying at least one of an energy intensity and a treatment time that are about 10% to about 50% higher than the highest settings that would be allowable if the lumen was not one or both of calcified or plaque containing arteries.

In an exemplary embodiment of the invention, selectively applying comprises selectively applying energy at a frequency range that would be allowable if the lumen was not one or both of calcified or plaque.

In an exemplary embodiment of the invention, the energy comprises one or several pencil beams of unfocused ultrasound energy emitted.

There is provided in accordance with an exemplary embodiment of the invention a device for treating a wall of a lumen in a limb, the lumen containing one or both of a plaque and a calcified wall, the lumen comprising:

a catheter sized to fit into the lumen;
an energy emission element disposed on a distal end of the catheter, the energy emission element adapted to transmit energy with an intensity sufficient to thermally damage tissue around a circumference of the lumen, the damaged tissue comprising nerves, the energy traversing at least some of the plaque and the calcified wall; and
a controller to control the energy emission element, the controller programmed to supply power at settings to thermally damage tissue around the lumen and beyond the plaque and the calcified wall, so that signals from nerves in the tissue are selectively treated thereby increasing blood flow to the limb.

In an exemplary embodiment of the invention, the energy emission element comprises an ultrasound emission element producing a single or several beam(s) of unfocused ultrasound.

There is provided in accordance with an exemplary embodiment of the invention a method of treating tissue in a lumen wall and/or surrounding tissue comprising:

inserting a catheter including an energy emission element into a region of the lumen containing a deployed stent;

selectively applying energy from within the lumen, so that a beam(s) from the energy emission element crosses struts of the stent, to form one or more longitudinal or circumferential spaced apart regions of tissue damage in the lumen wall or surrounding tissue without damaging an intima in direct contact with the stent and/or without stent deformation.

In an exemplary embodiment of the invention, the lumen comprises a renal artery.

In an exemplary embodiment of the invention, the energy emission element comprises an ultrasound emission element producing a beam of unfocused ultrasound.

In an exemplary embodiment of the invention, the selectively applying comprises selecting treatment parameters as if the stent was not present.

There is provided in accordance with an exemplary embodiment of the invention a method of treating a heart wall comprising:

selectively applying ultrasound energy from within a heart chamber to a wall of the heart to form one or more damage areas preventing conduction of contraction signals therethrough without damaging an endocardium, the damage areas comprising a full thickness of myocardial tissue, wherein the endocardium is cooled by blood.

In an exemplary embodiment of the invention, selectively applying comprises selectively forming a plurality of contiguous damage regions around an ostium of one or more pulmonary veins.

In an exemplary embodiment of the invention, selectively applying comprises selectively applying the ultrasound energy so that the damage region does not extend more than about 0.5 mm into a pericardium.

In an exemplary embodiment of the invention, selectively applying comprises selectively applying ultrasound to form stacked damage regions extending the full length of a hypertrophied myocardium.

There is provided in accordance with an exemplary embodiment of the invention a device for treatment of a heart wall comprising:

a catheter sized to fit into a chamber of the heart;

an energy emission element disposed on a distal end of the catheter, the energy emission element adapted to transmit energy with parameters to damage a myocardium;

a controller to control the energy emission element, the controller programmed to supply energy for a time period ranging from about 5 to 120 seconds, at a frequency of about 15 MHz to 40 MHz, at an intensity of about 20 Watt/cm^2 to 50 Watt/cm^2, the energy setting sufficient to selectively damage a full thickness of the myocardium without damaging an endocardium, thereby preventing conduction of contraction signals.

In an exemplary embodiment of the invention, the catheter further comprises an expanding device to maintain a gap between the energy emission element and the heart wall of at least 0.3 mm.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit, for example a catheter's EEPROM. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings and/or images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1A is a is a simplified schematic of the kidney vasculature, useful for practicing some embodiments of the invention;

FIGS. 1B-1G are schematics of some possible anatomical variations of the anatomy of FIG. 1A, useful for understanding some embodiments of the invention;

Figure 6:
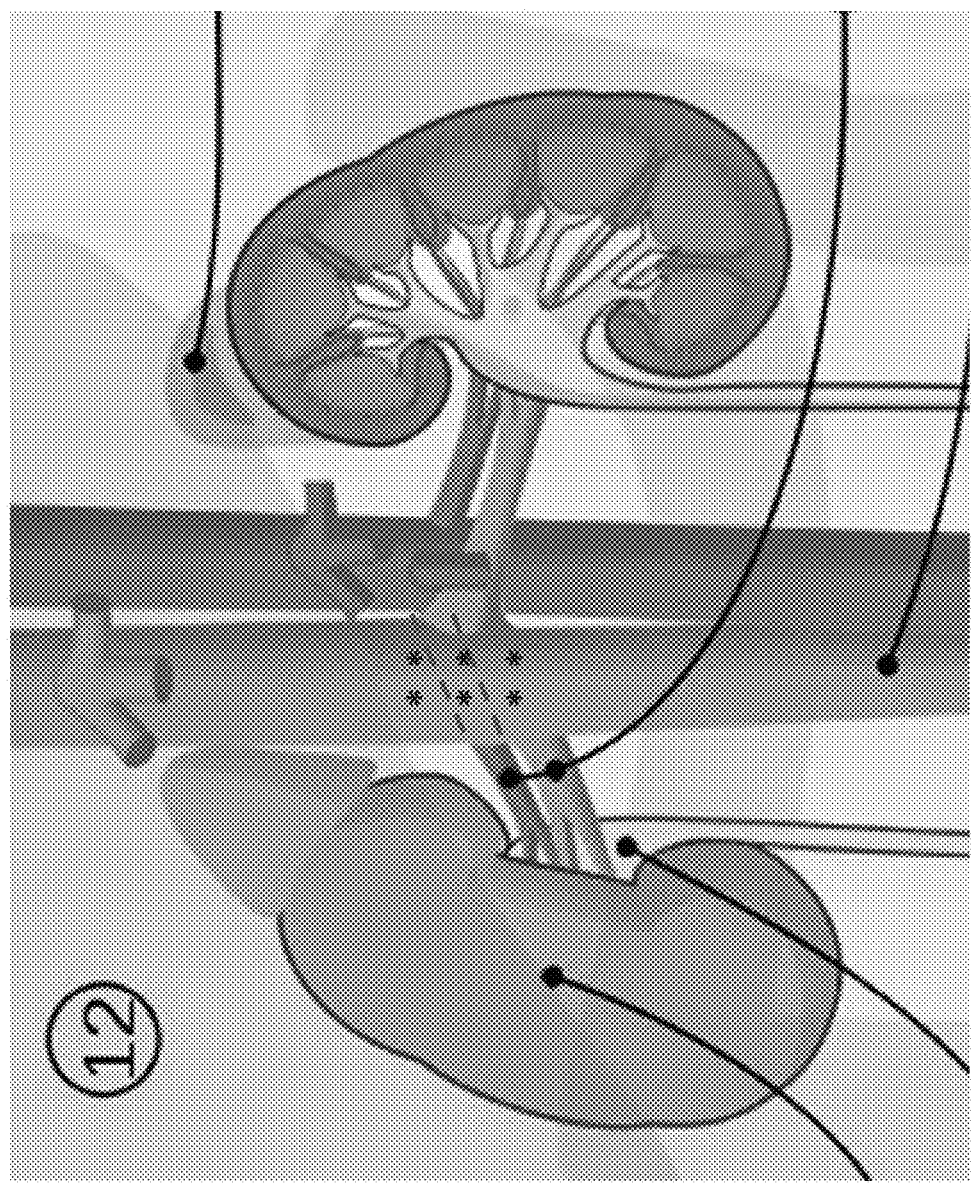
Figure 8A:
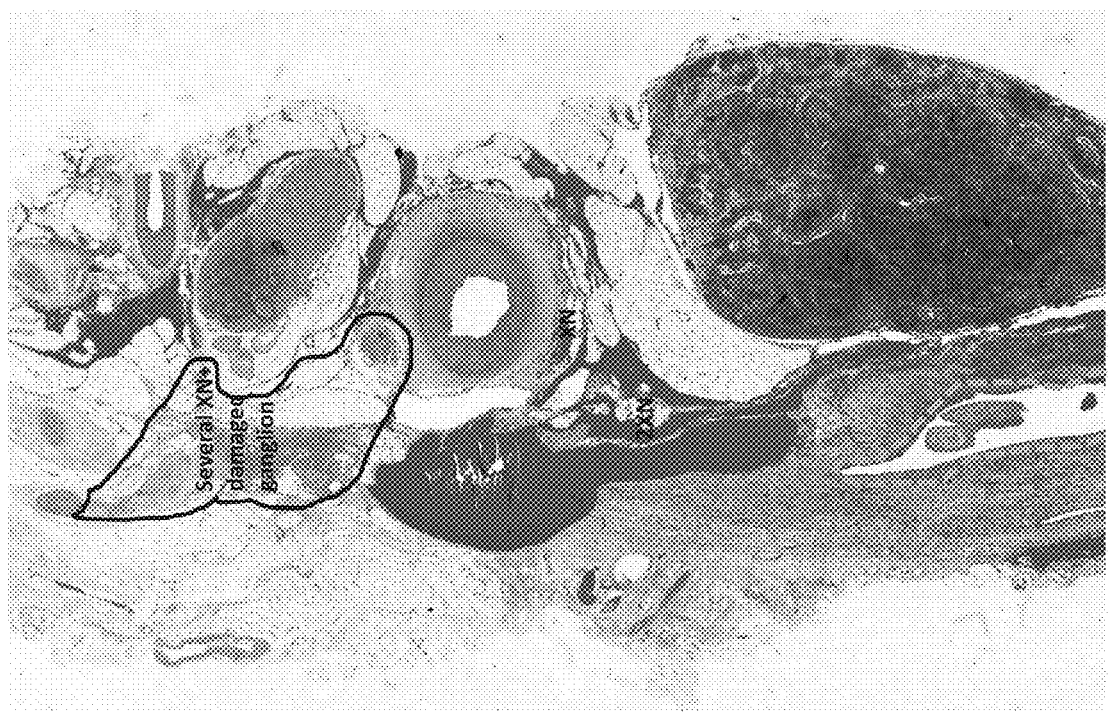
Figure 8B:
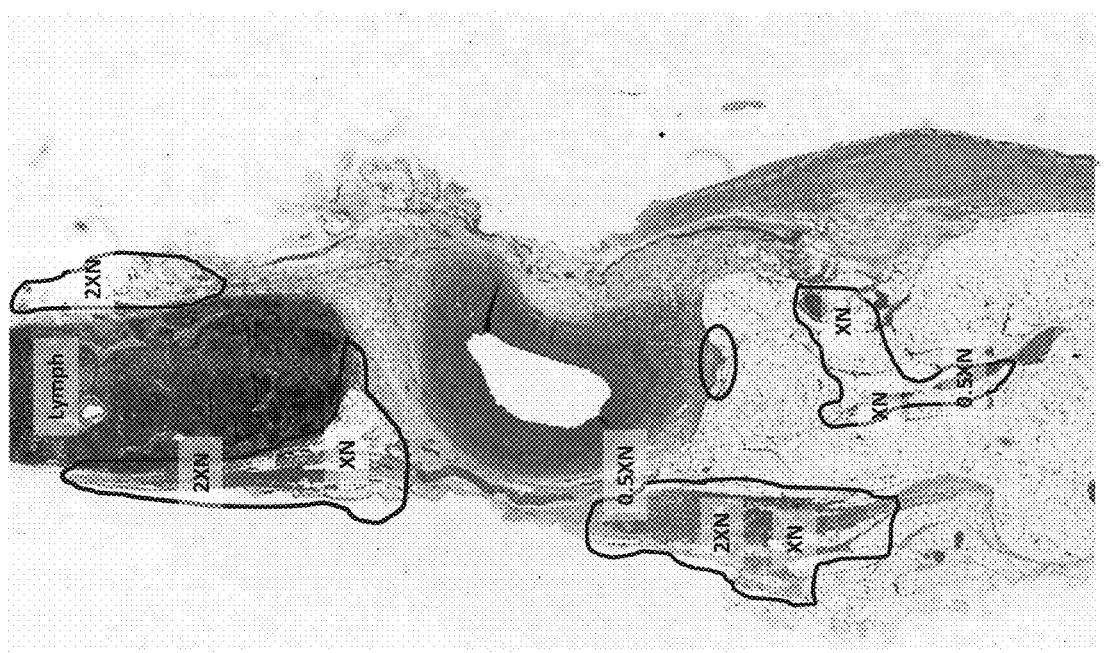
Figure 8C:
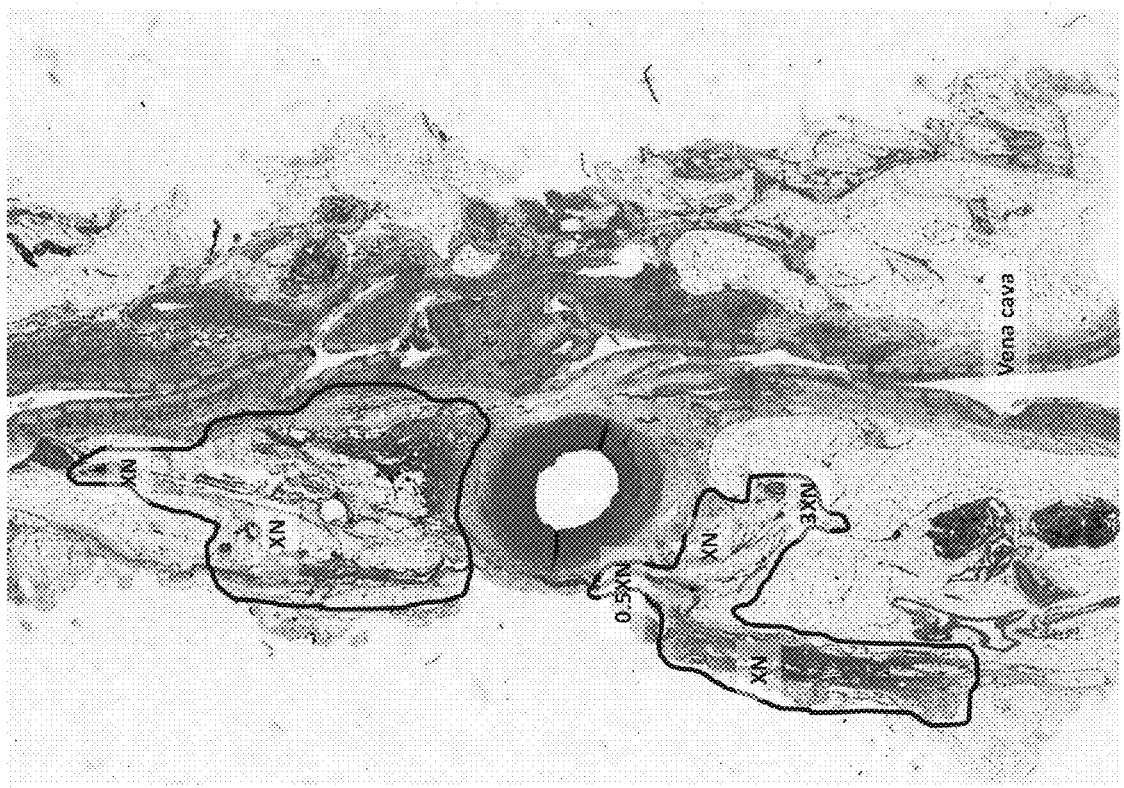
Figure 9:
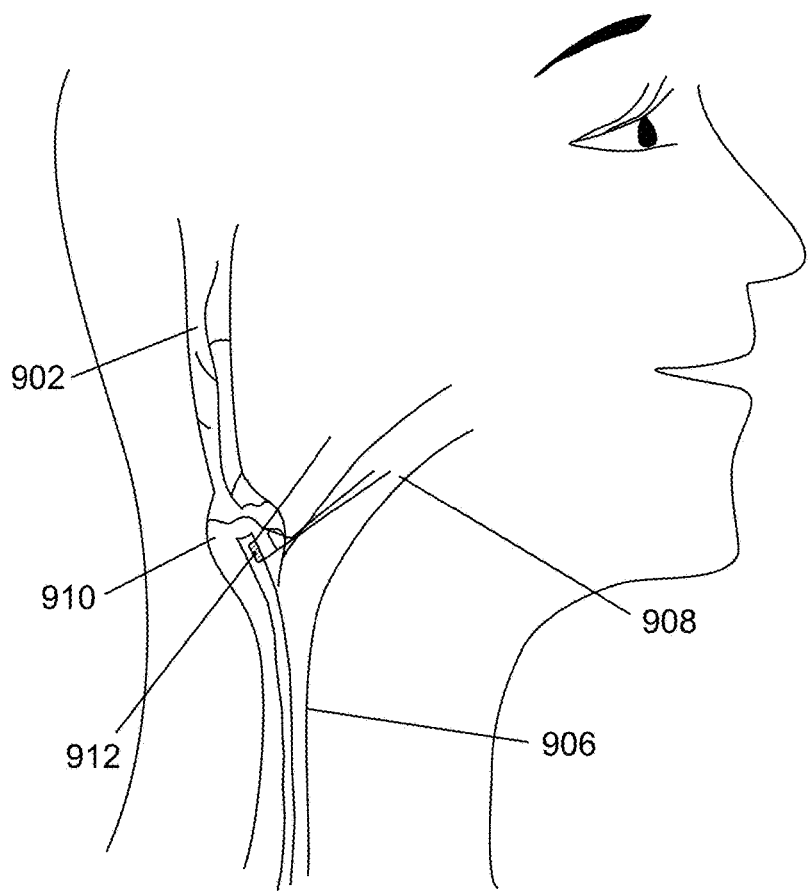
Figure 11:
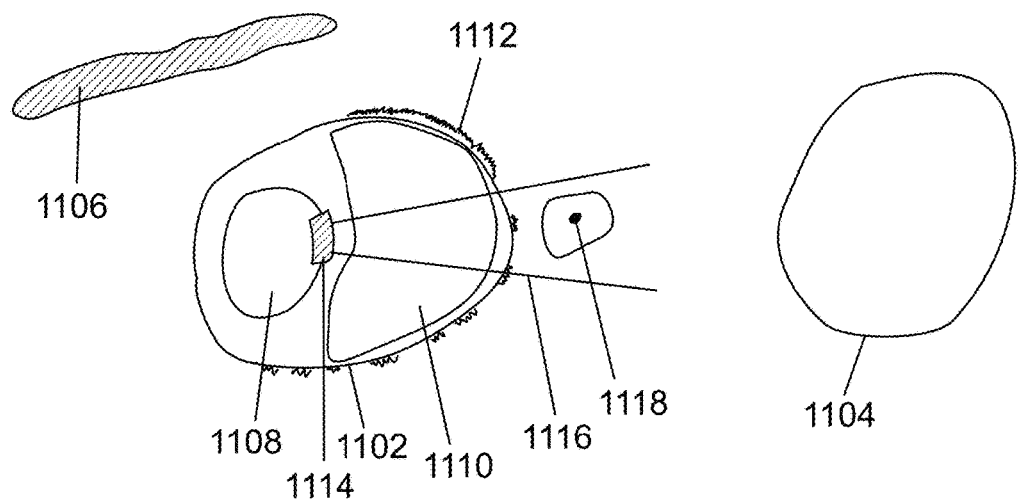
Figure 12B:
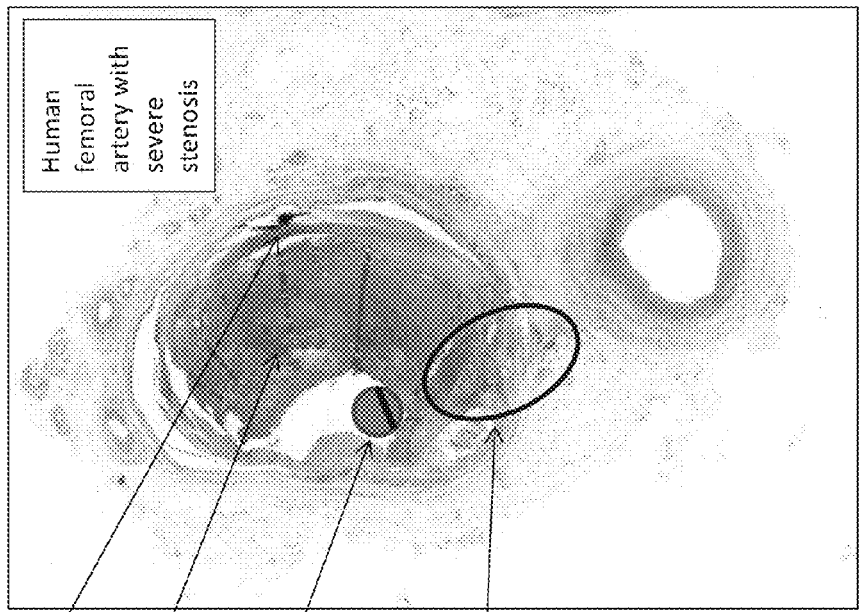
Figure 12A:
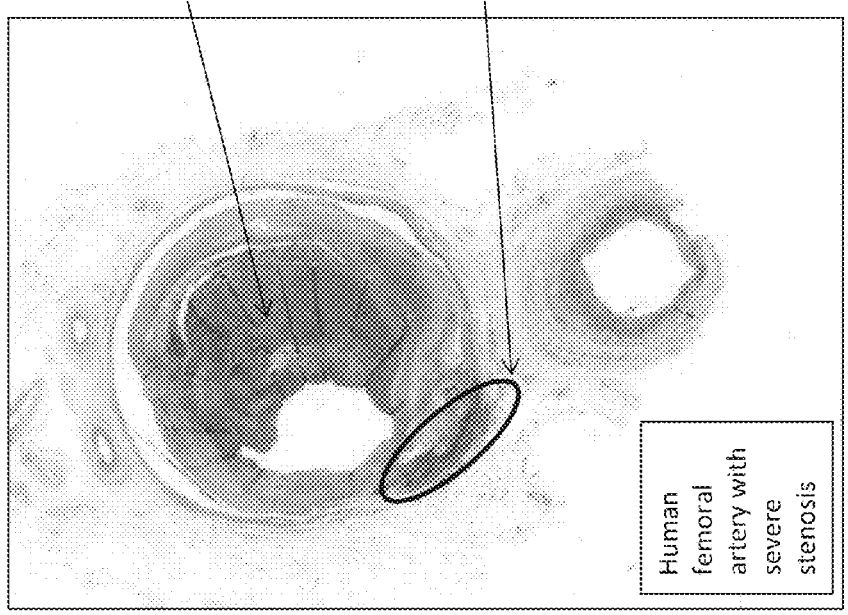
Figure 14:
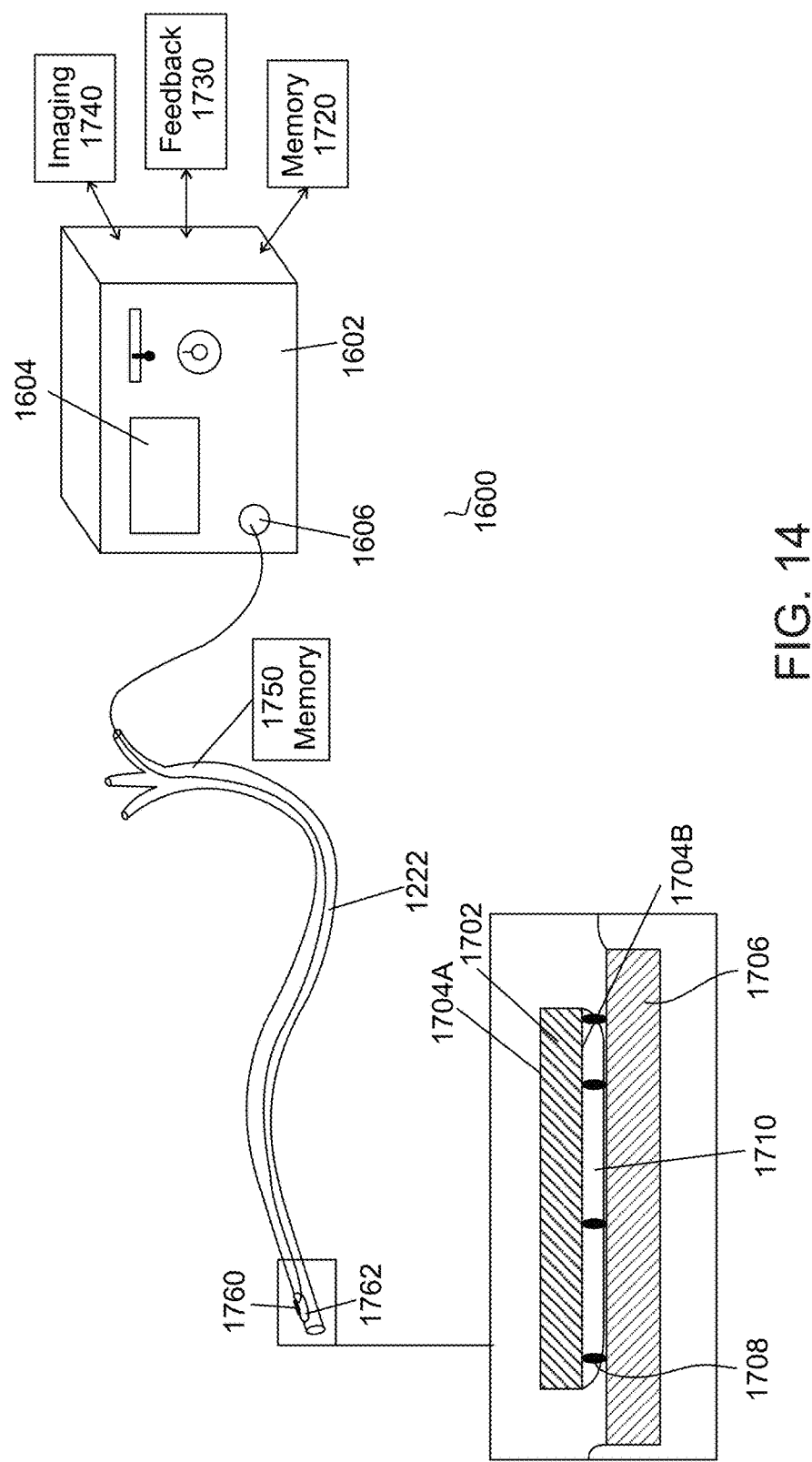
Figure 15A:
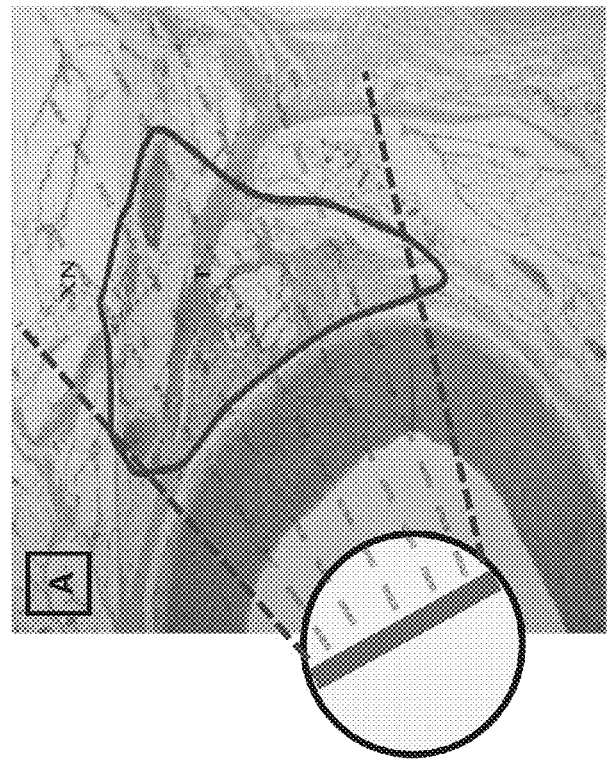
Figure 15B:
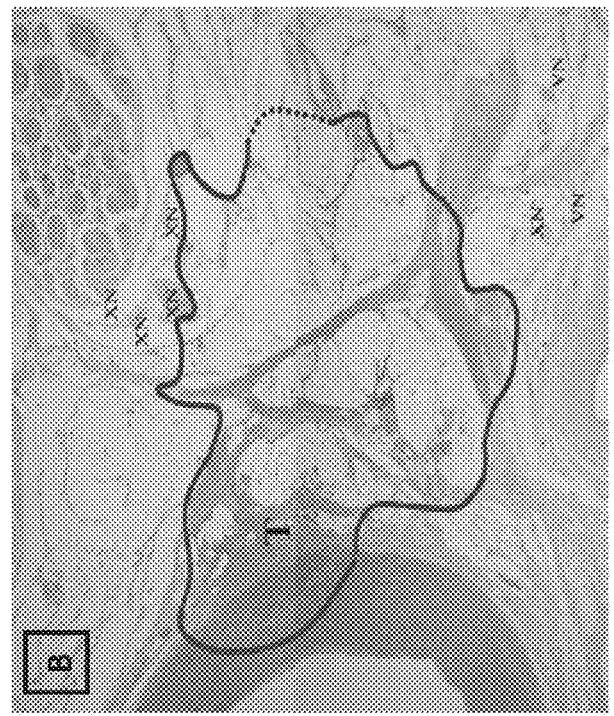
Figure 16A:
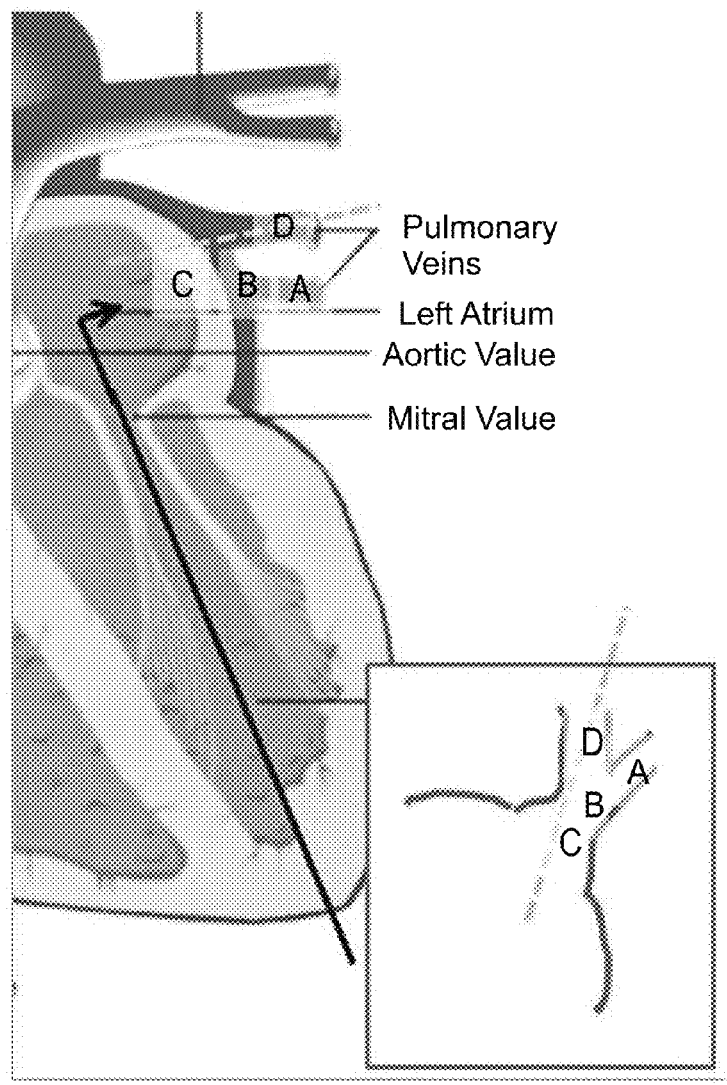
Figure 16B:
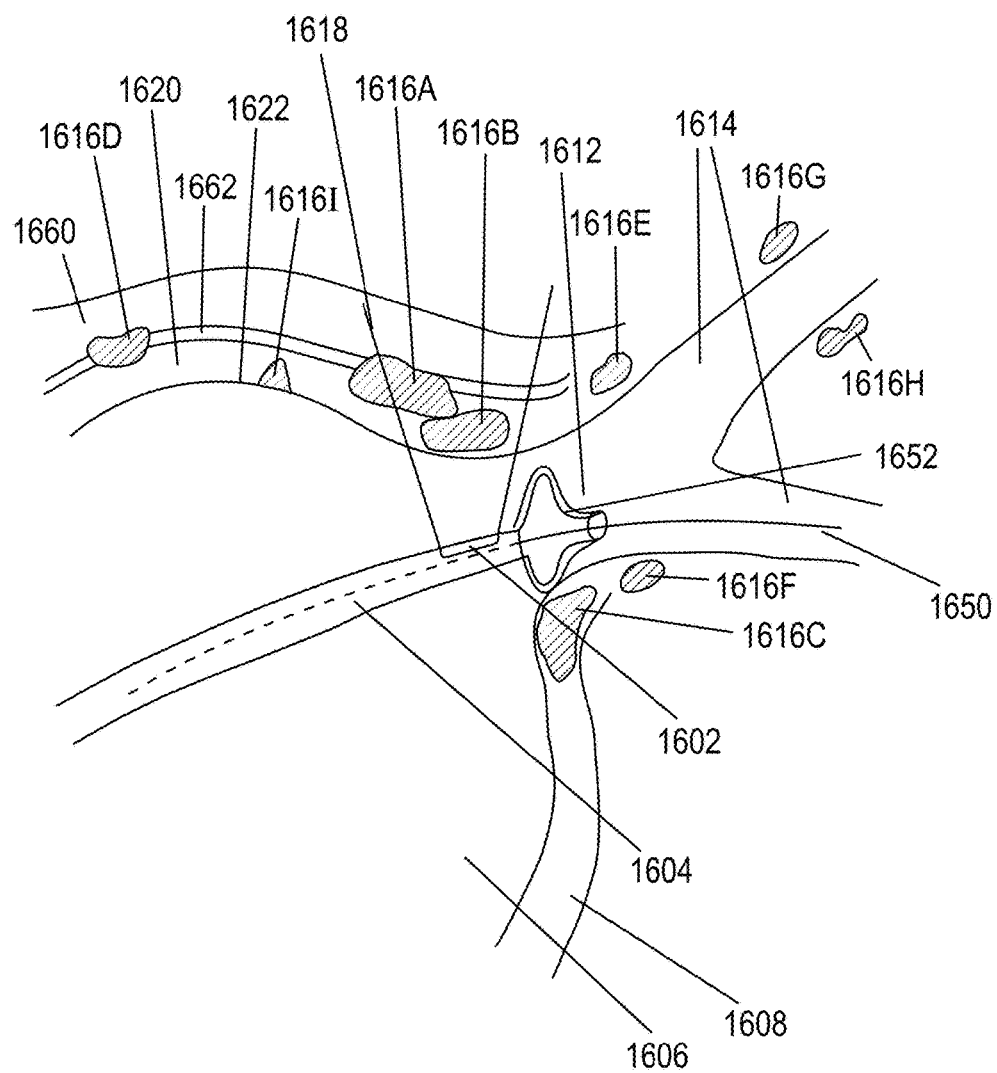
Figure 17:
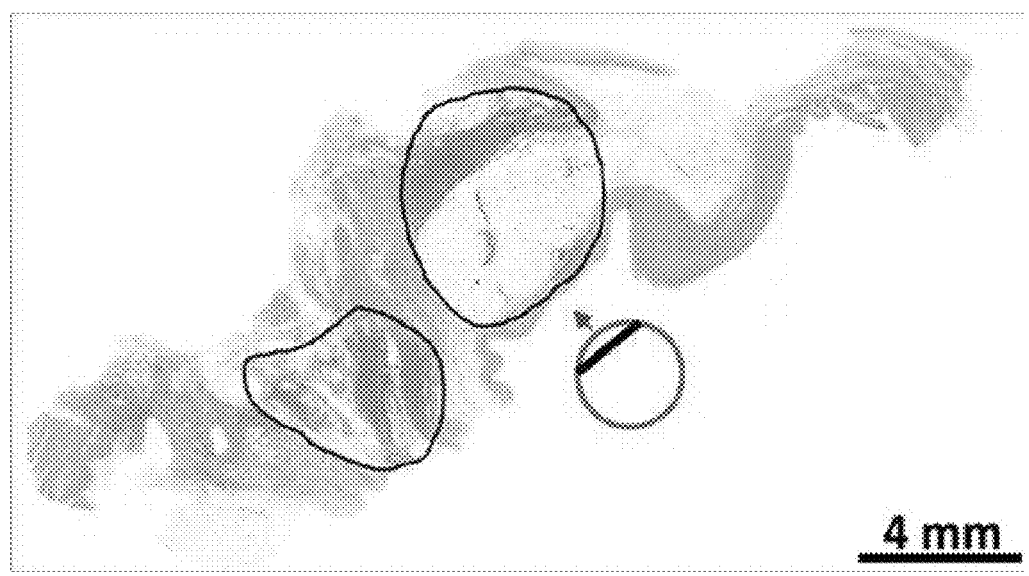

FIGS. 2A-D are flow charts of methods of tissue treatment, in accordance with an exemplary embodiment of the invention;

FIGS. 3A-E are schematics of a device for insertion into a lumen, in accordance with an exemplary embodiment of the invention;

FIGS. 4A-D illustrate positioning of an energy emission element inside a first lumen substantially perpendicular to a second lumen, in accordance with an exemplary embodiment of the invention;

FIGS. 5A-C illustrate positioning of an energy emission element inside a first lumen substantially parallel to a second lumen, in accordance with an exemplary embodiment of the invention;

FIG. 6 is a schematic showing the locations of ultrasonic ablations from the vena cava towards the right renal artery during an experiment, in accordance with an exemplary embodiment of the invention;

FIGS. 7A-F are angiography images obtained during the experiment;

FIGS. 8A-C are images of histology slides around the renal artery and vena cava obtained as part of the experiment, showing some experimental results;

FIG. 9 is a schematic of a right internal carotid artery, useful for understanding some embodiments of the invention;

FIGS. 10A-D are some not necessarily limiting examples of damage patterns, in accordance with some embodiments of the invention;

FIG. 11 is a schematic of a stenotic femoral artery, useful for understanding some embodiments of the invention;

FIGS. 12A-B are histological slides showing some experimental results around the femoral artery;

FIGS. 13A-F are angiography images and histological slides obtained during or following an experiment for treating tissue through a stent, in accordance with an exemplary embodiment of the invention;

FIG. 14 is a schematic of an exemplary treatment system, in accordance with an exemplary embodiment of the invention;

FIGS. 15A-B are images of histology slides obtained as part of an experiment in the carotid artery, showing some experimental results;

FIGS. 16A-B are schematic showing treatment of the heart, in accordance with an exemplary embodiment of the invention;

FIG. 17 is an image of a histology slide obtained as part of an experiment in the left atrium, showing some experimental results.

FIGS. 18A-F are angiography images obtained during or following an experiment for treating tissue through a stent, in accordance with an exemplary embodiment of the invention; and FIGS. 19A-G are histological results showing some experimental results around the renal artery, of treating tissue through a stent.

DESCRIPTION OF SPECIFIC EMBODIMENTS OF THE INVENTION

The present invention, in some embodiments thereof, relates to a method of tissue treatment and, more particularly, but not exclusively, to a method of selectively applying energy to treat tissues.

An aspect of some embodiments of the invention relates to a method of treating tissue near a first lumen by delivery of energy from a second lumen. Optionally, the first lumen is an artery. Optionally or additionally, the second lumen is a vein. Optionally or additionally, the energy is in the form of a non diverging beam, for example a pencil beam (e.g., ray) of ultrasound (US), for example, unfocused ultrasound. Some embodiments include different shapes of beams, for example a converging beam may be used. In some embodiments non diverging beams may be used. In some embodiments, a diverging beam may be used. Optionally, the beam has a low diverging angle, for example ranging between 0-30 degrees, for example 10-20, such as about 15 degrees, for example having 7.5 degrees on opposite sides of a plane that is perpendicular to the transducer. In some embodiments, the beam has a higher diverging angle, for example ranging between 50-120 degrees. In some embodiments, the beam may diverge and/or converge in one or more dimensions of the beam, for example have a low diverging angle on the perpendicular plane, and a higher diverging angle on a plane that crosses the perpendicular plane.

In some embodiments, by controlling an angle of a diverging beam, the location and/or geometry of the tissue ablation may be controlled. In some embodiments, the angle is fixed. In some embodiments, parameters such as energy intensity may be chosen for a given angle to optimize the treatment In an exemplary embodiment of the invention, the tissue near the right renal artery is treated by delivery of energy from the inferior vena cava. Alternatively, energy is delivered from one or more right renal veins.

In an exemplary embodiment of the invention, the tissue near the left renal artery is treated by delivery of energy from one or more left renal veins.

In an exemplary embodiment of the invention, the tissue is sufficiently treated to achieve an effect, for example, tissue damage, for example, a thermal effect. Not necessarily limiting examples of possible effects (e.g., thermal effects) include; burning, coagulation, denaturation, ablation, necrosis, disruption (e.g., of signal propagation in nerves), degeneration, destruction.

In an exemplary embodiment of the invention, the treated region contains one or more nerves, for example, renal artery nerves. Optionally, the nerves are thermally treated. Optionally, the nerves are disposed around different parts of the artery, for example, the renal artery nerves branch and cover different areas of the renal artery. Alternatively, the nerves are located in a bundle, for example, the femoral nerve.

In an exemplary embodiment of the invention, a region of damage is formed in less than about 5 seconds, or less than about 10 seconds, or less than about 15 seconds, or less than about 20 seconds or less than about 30 seconds, or less than about 60, or less than about 90 seconds, or less than about 180 seconds, or less than about 240 seconds, or other smaller, intermediate or larger times.

In an exemplary embodiment of the invention, one or more regions of damage are selectively formed around the artery. For example, 2, 4, 6, 8, or other smaller, intermediate or larger numbers of regions. Optionally, the regions are spaced apart. In some embodiments, several regions are treated simultaneously by multiple energy emission elements.

In an exemplary embodiment of the invention, the treatment areas have an axial length (e.g., as measured along the radius from the center of the artery) of about 1 mm to 20 mm, or about 2 mm to 15 mm, or about 5 mm to 10 mm, or about 10 mm to 20 mm, or about 2 mm to 8 mm, or other smaller, intermediate or larger axial lengths are selected.

In an exemplary embodiment of the invention, the treatment areas have a width (e.g., as measured substantially parallel to a tangent of the artery) of about 1 mm to 10 mm, or about 2 mm to 8 mm, or about 3 mm to 6 mm, or about 2 mm to 6 mm, or about 2 mm to 4 mm, or other smaller, intermediate or larger widths are selected.

In an exemplary embodiment of the invention, the intima of the artery is not significantly damaged by the energy.

In an exemplary embodiment of the invention, the treatment areas are selectively formed a distance of about 0.5 mm to 10 mm, or about 1 mm to 6 mm, or about 1.5 mm to 5 mm, or about 1.5 mm to 4 mm, or about 2 mm to 3 mm, or about 1 mm to 3 mm, or about 1 mm to 2 mm, or about 0.5 mm to 2 mm, from the inner wall of the artery (e.g., intima), or other smaller, intermediate or larger distances are selected.

In an exemplary embodiment of the invention, the treatment areas are selectively formed within a distance of about 0.5 mm to 20 mm, or about 1 mm to 10 mm, or about 2 mm, to 15 mm, or about 2 mm to 8 mm, or about 3 mm to 10 mm, or about 2 mm to 5 mm, or about 3 mm to 6 mm, or about 0.5 mm to about 3 mm from the vein, or other smaller, intermediate or larger distances are selected.

In an exemplary embodiment of the invention, the treatment areas are selectively formed in tissue near the artery. The percentage of the surface area around the artery that is covered is about 10%-80%, or about 20%-70%, or about 20%-50%, or about 30%-40%, or about 30%-60%, or about 5%-20%, or other smaller, intermediate or larger percentages are treated.

In an exemplary embodiment of the invention, the treatment areas selectively cover a sector (relative to the center of the artery) of about 5 degrees to about 120 degrees, or about 10 degrees to about 100 degrees, or about 15 degrees to about 90 degrees, or about 30 degrees to about 60 degrees, or about 15 degrees to about 45 degrees, or other smaller, intermediate or larger sectors are formed.

In an exemplary embodiment of the invention, the treatment area is selected to have a tangential dimension (measured substantially relative to the lumen e.g., artery) of no more than about 8 mm, or about 6 mm, or about 4 mm, or about 2 mm, or about 1 mm or other smaller, intermediate or larger sizes are selected.

In an exemplary embodiment of the invention, a treatment area is selected to have a radial dimension (measured substantially from the center of the lumen e.g., artery) of no more than about 8 mm, or about 5 mm, or about 3 mm, or about 1 mm or other smaller, intermediate or larger sizes are selected.

In an exemplary embodiment of the invention, a treatment area is selected to have an axial dimension (measured substantially parallel to the long axis of the lumen e.g., artery) of no more than about 10 mm, or about 8 mm, or about 6 mm, or about 4 mm, or about 2 mm or other smaller, intermediate or larger sizes are selected.

In an exemplary embodiment of the invention, the method comprises imaging the artery from the vein, for example, by a catheter in the vein. Optionally, imaging is performed by Doppler using ultrasound.

In an exemplary embodiment of the invention, the method comprises propping open the vein, for example, using a stent and/or a balloon and/or an expanding device of the US catheter. Optionally, the lumen is opened to allow the US catheter to be inserted into the vein. Optionally or additionally, the lumen is opened to ensure sufficient blood flow across the US emission element and/or the wall for cooling of the element. In practice, some veins have relatively thin and flimsy walls. Potentially, propping open the vein helps to maintain a substantially circular cross sectional shape.

In some embodiments, a stent is implanted in a vessel prior to the treatment. In some embodiments, a stent was previously implanted in a patient, for example due to unrelated stenosis. Optionally, the stent is covered by endothelial cells. In some embodiments, a stent is implanted intentionally before and/or during the treatment, for example to allow applying a higher intensity of the treatment, as will be further explained.

In an exemplary embodiment of the invention, an ultrasonic energy profile (e.g., intensity and/or frequency of US energy, time energy is delivered) applied from the vein to form the treatment areas near the artery, is relatively higher than would be allowed if the same catheter would be positioned instead within the artery. Potentially, the distance from the energy emitter in the vein to the target tissue is relatively larger than the distance to the target tissue if the emitter was placed in the artery, which requires relatively higher energy profiles to achieve the treatment. The comparison refers to allowed energy profiles that are safe, for example, do not cause damage to the intima of the arterial wall. Potentially, relatively larger sizes, relatively larger numbers and/or relatively more damage per area are possible from the vein approach over the arterial approach. Potentially, the tissue treatment is performed using the vein approach with a relatively higher degree of safety if the same settings are used (e.g., intensity, time duration), for example, a relatively lower risk of damage to the arterial intima. In some embodiments, the vein is stented after treatment to avoid adhesions.

In an exemplary embodiment of the invention, the highest allowable intensity of the emitted US beam from within the vein to the artery is relatively higher than the highest allowable intensity if the US was emitted from inside the artery. For example, about 110% higher than the intensity allowed or about 120%, or about 130%, or about 150%, or about 170%, or about 200% higher, or other smaller, intermediate or larger intensities are used. Alternatively or additionally, the intensity of US is, for example, about 10 Watt/cm$^2$, or about 20 Watt/cm$^2$, or about 30 Watt/cm$^2$, or about 40 Watt/cm$^2$, or about 50 Watt/cm$^2$, or about 60 Watt/cm$^2$, or other smaller, intermediate or larger intensities are be used. Note that the intensity is selected per location, as some treatment locations require higher intensities than other locations. Alternatively, the same intensity setting is used for some treatment locations or for all treatment locations.

Optionally or additionally, the highest allowable time duration of the delivery of US energy from the vein is higher than the time duration allowed if the US was emitted from inside the artery. For example, about 110%, or about 120%, or about 130%, or about 150%, or about 170%, or about 200% higher, or other smaller, intermediate or larger time durations are selected. Alternatively or additionally, the time duration of US is about 5 seconds, about 10 seconds, or about 20 seconds, or about 30 seconds, or about 40 seconds, or about 60 seconds, or about 100 seconds, or other smaller, intermediate or larger time durations are used.

In some embodiments, areas are treated for a longer time period instead of with a higher intensity.

Optionally or additionally, the frequencies used are relatively lower when used in the vein relative to the artery, for example, if the distance to the target tissue is relatively larger. For example, about 90%, or about 80%, or about 70%, or about 60%, or about 50%, or other smaller, intermediate or larger percentages. For example, about 5 Mhz, 8 Mhz, about 10 Mhz, about 15 Mhz, about 20 Mhz, about 30 Mhz, about 40 Mhz, or other smaller, intermediate or larger frequencies. In some cases, the frequencies used in the vein can overlap with those used in the artery, for example, where the distance to the target tissue is substantially the same from the artery or from the vein.

An aspect of some embodiments of the invention relates to an expandable device for opening a lumen (e.g., vein and/or artery). In an exemplary embodiment of the invention, the device expands to a predetermined diameter and/or predetermined shape. Without being necessarily bound by theory, as the vein walls are relatively weaker than arterial walls and/or are not as elastic, the device shapes the vein into the preselected shape and/or diameter. In practice, the vein has an irregular shape and/or the vein is in the collapsed state, which is unsuitable for insertion of the treatment catheter. Optionally, the device maintains the lumen in a substantially circular open state.

In some embodiments, struts of the expandable device are arranged so as not to interfere with an ultrasound energy beam or multiple beams being emitted through the device. Optionally, the struts themselves are designed to not damage walls, for example, by having rounded edges, for example having rounded peaks, or rounded bending points.

In some embodiments, the device is collapsible for removal from the vein after treatment. In some embodiments, gradually opening and/or closing the expandable device is performed mechanically and/or automatically, for example using a lever in the catheter handle. Alternatively, the device is left in place.

In some embodiments, the expanded device provides a force against the vein walls that is insufficient to damage the walls (as vein walls are relatively weaker than arterial walls, and/or are not as elastic).

In some embodiments, the device provides a clearance between the beam source and the arterial wall. For example, a clearance of at least 0.1 mm, or at least 0.3 mm, or at least 0.5 mm, or at least 1 mm, or at least 1.5 mm, or at least 2 mm, or at least 3 mm, or at least 4 mm, or other smaller, intermediate or larger sizes. Optionally, the clearance is selected to allow blood to cool the target tissue and/or surrounding tissues. Alternatively or additionally, the clearance is selected to allow blood to cool the beam source(s) so that the blood remains below a safe level, for example, below about 42 degrees Celsius, or 45, or 48 or 50, or other smaller, intermediate or larger temperatures. In some embodiments, the expandable device can be used for preventing direct contact of the energy emitting element with the wall of the artery or vein.

In some embodiments, the flow of blood is guided to go into the clearance gap, for example, by a groove on the catheter.

In some embodiments, the device is designed to be used in stenotic arteries (e.g., containing plaques), and provides a force against the arterial wall that is sufficient to maintain a patent arterial lumen against the stenosis (e.g, plaques).

An aspect of some embodiments of the invention relates to applying energy from within a lumen (e.g., artery or vein) across a lumen patency device (e.g., a stent or stent-graft) to treat regions (e.g., thermally) in the lumen wall. Optionally, the energy delivery is performed without damaging the intima of the lumen, for example, the energy delivery is performed without causing stent deformation, or without heating the stent struts in contact with the intima to damage the intima. In an exemplary embodiment of the invention, the blood flow is selected to be high enough to cool the stent. Optionally, the cooling of the stent by blood flow prevents heating of tissues by the stent to a temperature high enough to cause damage, for example, no more than about 42 degrees Celsius, or about 44, or about 46, or other smaller, intermediate or larger temperatures.

In some embodiments, damage to the vessel wall from the heated stent is limited (at least mostly) to areas covered by stent struts.

In some embodiments, the stent increases the flow rate of blood through the vessel. In some embodiments, the stent, for example the struts, conduct heat from the vessel wall to deeper nearby tissue layers, and/or into blood flow. In some embodiments, the thickness of the stent affects the heating of the tissue, for example a thicker stent may act as a barrier between the targeted tissue and the applied energy beam. In some embodiments, the thermal conductivity of the stent material affects the heating of the tissue, for example by diffusing the heat in a faster rate. In some embodiments, a higher frequency and/or intensity may be applied when a stent is used, for example to modulate nerve activity to a certain level. In some embodiments, for example if a portion of the stent is positioned between an energy beam and the tissue, the stent may create a shadow like effect on the tissue, and at least a portion of the energy may not affect the tissue. Optionally, as a result, the shadowed tissue may be cooler than other portions of the tissue which are directly exposed to the beam.

In some embodiments, at least 0.02-10% or intermediate or larger values of the vessel wall tissue which is exposed to the energy beam are covered by the stent.

In some embodiments, the stent widens the vessel. Optionally, the widening allows for a stronger blood flow, for example in comparison to non-stented vessels. Optionally, the stronger blood flow increases the cooling rate of the tissue. Optionally, the faster cooling rate of the tissue may decrease the effect of the applied energy on the tissue. In some embodiments, the stent is used as a cooling mechanism, for example if turbulence is created along the vessel wall by the stent, optionally diffusing the heat.

In some embodiments, the treatment may be affected by certain stent properties such as material, size, thickness, structure, electric conductivity, thermal conductivity, thermal capacity, or any other properties and/or combinations of them.

In some embodiments, the stent may block and/or absorb at least a portion of the emitted energy. Optionally, as a result, tissue located nearby the stent may not be heated directly. Additionally and/or alternatively, as a result of absorbing at least a portion of the energy, the stent may cool nearby tissue. In some embodiments, the stent may conduct heat from the tissue to the blood flow and/or vice versa, and/or conduct heat between two or more locations of the tissue.

In some embodiments, the stent is intentionally heated by the applied ultrasound energy, for example by setting parameters such as frequency and/or direction.

In some embodiments, a system for treating is adapted to treat tissue through a stent. In some embodiments, the system automatically detects the stent. In some embodiments, the system has pre-defined parameters for compensating for treatment through a stent, for example by increasing the applied intensity of the ultrasonic emission. In some embodiments, the above described parameters may be taken into account when automatically selecting parameters.

In some embodiments, the system detects the stent using ultrasonic echo waves returning from the stent. In some embodiments, the system may cancel the stent echo to receive clearer echo signals from deeper tissue. In some embodiments, characteristics of the echo signals are analyzed to determine the existence of the stent. Optionally, characteristics are analyzed to determine the size, material, and/or positioning of the stent.

An aspect of some embodiments of the invention relates to applying energy to disrupt signal propagation from baroreceptors in the carotid sinus to the brain. Optionally, the disruption treats over-activity of the baroreceptors, for example, carotid sinus syndrome.

An aspect of some embodiments of the invention relates to applying energy from within a lumen (e.g., artery) across a plaque and/or a calcified lumen wall to treat areas in the lumen wall and/or tissue near the lumen (e.g., adventitia, nerves, adipose tissue, vasa vasorum, arterioles, venules). Optionally, nerves are thermally treated.

In some embodiments, the intensity and/or time settings are higher than the highest intensity that would be allowable in the same artery without the plaque and/or calcification. For example, about 10% higher, or about 25%, about 40%, about 50% higher, or other smaller, intermediate or larger percentages of time and/or intensity.

In some embodiments, a catheter used to apply the energy is sized and/or is rigid enough to be inserted into the stenotic lumen. Optionally, the catheter is directed over a guidewire inserted through the stenotic lumen.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

An aspect of some embodiments of the invention relates to a method of applying energy to form treatment regions that disrupt conduction of contraction signals in the wall of the heart. Optionally, the disruption treats over-activity of the myocardium, for example, atrial fibrillation.

In some embodiments, the treatment regions extend most of the full thickness of the myocardium. Alternatively, the regions extend partially along the thickness of the myocardium (e.g., hypertrophied myocardium). Optionally, the partial thickness regions are stacked to extend along the full thickness of the thicker myocardium.

In an exemplary embodiment of the invention, the endocardium is not damaged by the treatment.

In some embodiments, the treatment does not extend far into the pericardium.

Overview

Referring now to the drawings, FIG. 1A is a simplified schematic of the kidney vasculature, useful for practicing some embodiments of the invention.

In most patients, blood from a right kidney 102 drains into a vena cava 110 by a right renal vein 106. Blood from a left kidney 104 drains into vena cava 110 by a left renal vein 108. Right kidney 102 is supplied by blood from an aorta 116 via a right renal artery 112. Left kidney 104 is supplied by blood from aorta 116 via a left renal artery 114.

A shaded region 118 represents an area and/or volume within vena cava 110 that is in close proximity to right renal artery 112. A shaded region 120 represents a volume and/or area within left renal vein 108 that is in close proximity to left renal artery 114.

In an exemplary embodiment of the invention, US energy is applied to tissues near and/or in the wall of right renal artery 112 through region 118, for example, by a catheter inserted into vena cava 110. In an exemplary embodiment of the invention, US energy is applied to tissues near and/or in the wall of left renal artery 114, for example, by a catheter inserted into the left renal vein.

Figures 1B, 1C:
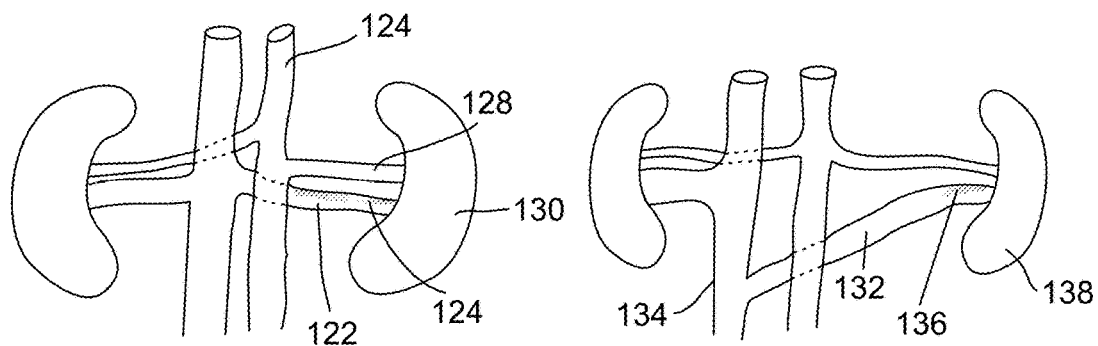

FIGS. 1B-1G represent some possible anatomical variations of the anatomy shown in FIG. 1A. In each case, the treatment zone within the venous vasculature that is close to the target tissue (e.g., renal artery wall and/or surrounding tissues) needs to be re-evaluated and re-selected.

FIG. 1B illustrates a left renal vein 122 positioned posterior to an aorta 124. A treatment zone 126 in close proximity to left renal artery 128 is located further inside vein 122, towards a left kidney 130.

FIG. 1C illustrates a left renal vein 132 connected relatively caudally to a vena cava 134, in comparison to other anatomies. A treatment zone 136 is located in close proximity to a left kidney 138.

Figures 1D, 1G:
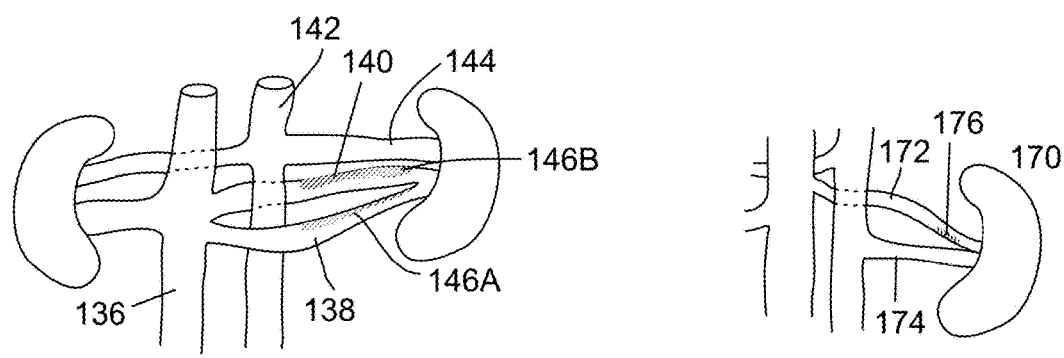

FIG. 1D illustrates two left renal veins connected to a vena cava 136; an anterior left renal vein 138 and a posterior left renal vein 140 (relative to an aorta 142). Depending on the location of a left renal artery 144, treatment zones 146A-B can be located in anterior vein 138 and/or posterior vein 140.

Figures 1E, 1F:
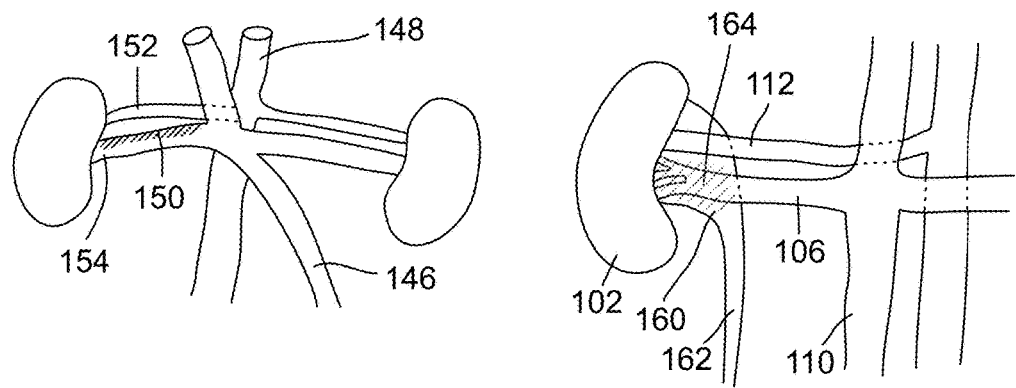

FIG. 1E illustrates a transposed inferior vena cava 146, with a portion above the kidneys located to the right of an aorta 148 and a portion below the kidneys located to the left of aorta 148. Treatment of a right renal artery 152 might be possible from a treatment zone 150 located in the right renal vein 154 (as opposed to within vena cava 146).

FIG. 1F illustrates the anatomy of FIG. 1A, showing the location of a urinary pelvis 160 and a ureter 162. Treatment of right renal artery 106 might be possible from a treatment zone 164 located within pelvis 160 and/or ureter 162. Treatment of the left renal artery can be similarly performed from the left renal pelvis.

FIG. 1G illustrates a left renal vein 172 located caudally (e.g., above) relative to a left renal artery 174. Treatment of left renal artery 174 might be possible from a treatment zone 176 within left renal vein 172 at the location when vein 172 is close enough to artery 174, for example, close to a left kidney 170.

It should be noted that patients may present with other anatomies that were not described. In each case, the anatomy can be evaluated to determine the treatment location from which to apply the energy.

Exemplary Treatment Using the Vein Approach

Figure 2A:
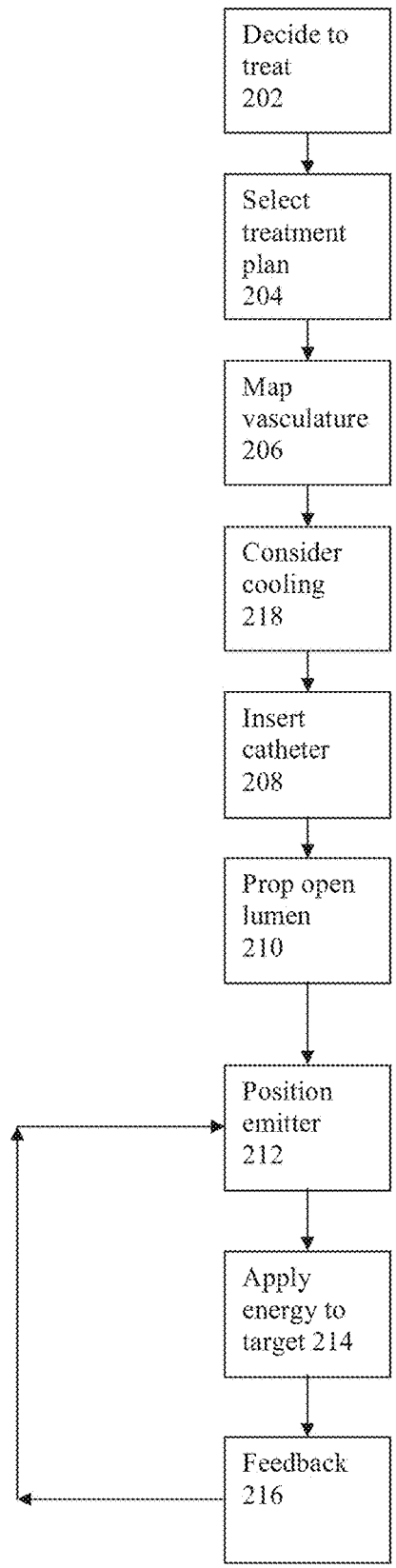

FIG. 2A shows a method of treating a wall of a first lumen (e.g., artery) in a human or mammal by applying energy, in accordance with an exemplary embodiment of the invention. Optionally, the energy is delivered from a second lumen (e.g., vein) in close proximity to the first lumen. Optionally, an energy emission region is selected to be sufficiently close to allow energy emitted from the first lumen (e.g., inferior vena cava) to be directed to form treatment regions around the circumference of the second lumen (e.g., right renal artery). It should be noted that even if treatment areas cannot be formed around the entire circumference of the artery, the US emission element can still be placed close enough to allow energy to be directed to at least some selected target areas around the artery. For example, the US emission element might be able to target up to about 70% of the circumference of the artery, or up to about 50%, or up to about 30%, or other smaller, intermediate or larger percentages.

It should be noted that the methods described in FIGS. 2A-D are not necessarily limited to the methods described below. For example, some steps are optional. The method can be used, for example, to treat a wall of an artery (e.g., femoral artery, carotid artery) by applying energy from within the artery, for example, as will be described below.

Optionally, nerves in the arterial wall are treated, for example, sufficiently damaged to prevent signal conduction. In some embodiments, nerves are treated to reduce kidney norepinephrine (NE) levels by a preselected amount and/or to a preselected level. Optionally, renal norepinephrine levels are selectively reduced (e.g., relative to a pre-treatment baseline) to a target level, for example, by about 25%, about 33%, about 50%, about 70%, about 80%, about 95%, or other smaller, intermediate or larger reductions are used. Optionally or additionally, the levels are reduced to a target range, for example, to about 10%-50%, about 30%-70%, about 20%-40%, or other smaller, intermediate or larger ranges are used. Alternatively, the levels are reduced to be below a target threshold, for example, below about 80%, below about 50%, below about 30%, below about 10%, or other smaller, intermediate or larger values are used. The selection is performed, for example, using a table correlating one or more treatment parameters with reduction in NE levels, the data being based on empirical evidence. Additional details of selective reductions in NE levels can be found, for example, with reference to provisional application 61/590,423 "Selective reduction of nerve activity", incorporated herein by reference in its entirety. Additional details of selective tissue damage can be found, for example, with reference to PCT/IB2011/054640 "Tissue Treatment", incorporated herein by reference in its entirety.

Optionally, at 202, a decision to treat the patient is made, for example, by the physician, in accordance with an exemplary embodiment of the invention. In an exemplary embodiment of the invention, the patient suffers from one or more conditions associated with abnormal renal nerve conduction, not necessarily limiting examples include; hypertension, heart failure, diabetes, sleep apnea. In an exemplary embodiment of the invention, the decision is made to treat nerves located in the renal artery wall (e.g., right, left or both arteries).

Optionally, one or more not necessarily limiting indications for the venous route over the arterial route include;

Difficult to access renal arteries, for example, arteries that are too tortuous for navigation with the catheter, arteries having diameters that are too small for introduction of the catheter (e.g., stenotic arteries), arteries having plaques and therefore being at risk for emboli upon insertion of the catheter.

Increased risk of arterial route; risk of perforating the artery and subsequent blood loss, risk of damage to the intima.

Potentially, as generally in the body arteries and veins travel in close proximity many arteries can be treated by the venous route.

Optionally at 204, a treatment plan is selected, in accordance with an exemplary embodiment of the invention. In an exemplary embodiment of the invention, the treatment plan comprises one or more treatment parameters, some not necessarily limiting examples include; frequency of US energy, intensity of US energy, time duration of US energy, number of targets, and/or location of the targets along the arterial wall.

In some embodiments of the invention, the treatment plan is correlated with a damage pattern (e.g., acute damage pattern). In some embodiments of the invention, the acute damage pattern and/or the treatment plan is correlated with a reduction in a measurable parameter correlated with nerve activity (e.g., renal norepinephrine). In practice, the physician selects the desired reduction in renal norepinephrine levels, and delivers energy according to the correlated treatment plan to produce the acute damage pattern, for example, as taught in provisional application 61/590,423.

In some embodiments, the correlation between the treatment parameters, the reduction in the measurable parameter and/or the acute damage pattern are provided by a correlation table, for example, stored on a memory in electrical communication with a controller, for example, as will be described with reference to FIG. 14.

In an exemplary embodiment of the invention, the time period for delivery of energy per treatment location is, for example, about 5 to 120 seconds, about 5-60, about 10-30, about 20-30, or other smaller, intermediate or larger time ranges.

In an exemplary embodiment of the invention, the US frequency is, for example, about 5-40 Mhz, or 10-20 Mhz, or other smaller, intermediate or larger ranges.

In an exemplary embodiment of the invention, the US intensity is, for example, about 10-60 Watt/cm^2, or 20-50 Watt/cm^2, or 30-40 Watt/cm^2, or other smaller, intermediate or larger ranges.

Optionally, at 206, the vasculature of the patient is mapped, in accordance with an exemplary embodiment of the invention. In some embodiments of the invention, the mapping provides details of the anatomy of the veins, the arteries, and the relative locations between the veins and the arteries. In practice, patients have variations in anatomical structures, requiring tailoring of the treatment to the patient. For example, as described with reference to FIGS. 1B-1E.

Some not necessarily limiting examples of mapping include; CT, angio-CT, MRI, angio-MRI, angiography, real time ultrasound. Mapping can be performed before and/or during the procedure.

Optionally, at 218, tissue cooling of the target tissue is taken into account. Optionally, cooling of the target tissue by blood flow through the lumen near the target tissue is considered. For example, target tissue near the vena cava is cooled relatively more by the blood flowing through the vena cava than target tissue further away from the vena cava. For example, in the case in which two target tissues are the same distance from the ultrasound emission element, but one is closer to the inner wall of the vena cava and the other is further away, the close target will be cooled more by the flowing blood, and the effect may be smaller.

In some embodiments, a table links parameters associated with the treatment area (e.g., location, size, shape, damage type) with control parameters (e.g., location of US emitter relative to the vein, blood flow through the vein and/or artery, energy application parameters). Some other not necessarily limiting examples of associations between treatment areas and parameters include; one or more functions, one or more rules, one or more neural networks. In a not necessarily limiting example, the correlation data is used to obtain the desired treatment region near the vein from the artery.

Optionally, the distance of the target tissue from the lumen is used to adjust the treatment parameters accordingly to form the selected target region.

Optionally, at 208, the treatment catheter is introduced into the vein using a percutaneous approach and threaded to the energy delivery site. Some not necessarily limiting examples of percutaneous access points include; femoral vein, jugular vein.

In some embodiments, the treatment catheter is inserted into the vein and a second catheter (e.g., used for reference on imaging) is inserted into the artery.

Optionally, at 210, the lumen from which energy will be delivered to the artery is propped open, in accordance with an exemplary embodiment of the invention. Optionally, the vein is propped open for example, using an expanding propping device.

Without being necessarily limited by theory, an explanation is presented of the difference in structure between veins and arteries. In the body, veins usually have relatively thinner media layers (e.g., muscular tissues) than arteries of similar size. Due to the lack of wall support, veins do not retain their shape. Veins are floppy, and therefore are usually found in the substantially collapsed state (e.g., lumen not fully patent). Furthermore, the cross sectional area of the lumen may have an irregular shape. Such veins need to be opened and kept open to allow insertion of the treatment catheter and/or to ensure sufficient blood flow to cool the catheter.

In an exemplary embodiment of the invention, a device is inserted into the vein to prop open the vein wall. Additional details are provided, for example, in the section "EXEMPLARY LUMEN SUPPORT DEVICE".

Optionally or additionally, the patient is positioned to help with propping open of the vein. Optionally, the patient is placed in the lateral decubitus position, for example, to help open up the vena cava by reducing abdominal pressure such as in pregnant and/or obese patients.

At 212, the US emission element is positioned within the artery to deliver the selected treatment plan, in accordance with an exemplary embodiment of the invention. Additional details are provided, for example, in the section "EXEMPLARY US DELIVERY".

In some embodiments of the invention, imaging is utilized to assist with positioning of the catheter inside the vein. Optionally, the artery is imaged from within the vein. Optionally, the artery and vein are imaged using different devices/approaches, for example, a contrast releasing catheter is inserted in the artery and a treatment catheter in the vein. Optionally, imaging is performed by US Doppler, to detect the relatively fast arterial blood flow. Not necessarily limiting examples of US imaging include; using the same US transducer to image the artery and to deliver the treatment (For example, as disclosed in PCT/IB2011/054636 "AN ULTRASOUND TRANSCEIVER AND USES THEREOF", incorporated herein by reference in its entirety), or a second US transceiver is introduced into the vein to perform the imaging. Alternatively, imaging is performed from outside the artery and/or external to the patient, for example, CT imaging during the procedure, fluoroscopic imaging, US imaging from outside the body.

In some embodiments, to make sure that the catheter in the vein is positioned towards the artery, the fluoroscopic equipment is rotated until one catheter is positioned overlapping and/or behind the other catheter.

At 214, US energy is applied to the tissue, to obtain the selected damage profile, in accordance with an exemplary embodiment of the invention. Optionally, the US energy is applied according to the selected treatment protocol, not necessarily limiting examples of parameters include; treatment time, ultrasound intensity, ultrasound frequency.

Optionally, at 216, feedback associated with the treatment is obtained, in accordance with an exemplary embodiment of the invention.

Optionally, the artery is monitored for a temporary contraction and/or spasm, for example, visually on fluoroscopy and/or by instrumentation (e.g., measuring changes in blood pressure in the artery). Potentially, the contraction is associated with application of a sufficient amount of US energy to the wall of the artery to form the area of treatment and not enough to damage the wall.

Optionally, power levels are selected according to the feedback. For example, after a first treatment (e.g., test point, entire treatment, partial treatment), imaging can be used to determine the extent of damage (e.g., size of area damaged, percent of area damage, type of damage). Power levels can then be adjusted according to the imaging data, to obtain the desired type of damage. For example, intensity can be increased to form larger damage areas and/or more damage.

Alternatively or additionally, other types of feedback are available, for example, applying an US signal, sensing the returning US echo, and analyzing the signal to estimate the amount of damage.

Optionally, 212, 214 and/or 216 are repeated, for example, to provide a plurality of damage areas according to the selected treatment plan. For example, the catheter is repositioned as in 212, in a different area (or same area) of target tissue which is treated as in 214 and optionally feedback is obtained to evaluate the treatment as in 216.

It should be noted that the method is not necessarily limiting, for example, some steps can be performed in different orders. For example, the treatment plan (as in 204) can be selected after the vasculature has been mapped (as in 206). For example, the vein can be propped open (as in 210) before the catheter has been inserted (as in 208). Furthermore, some steps are entirely optional. For example, some veins such as the inferior vena cava may not require being propped open (as in 210).

Furthermore, it should be noted that the method is not necessarily limited to the renal vasculature. Other not necessarily limiting examples of tissues surrounding the wall of a first lumen can be treated by applying energy from a second lumen include;

In some embodiments of the invention, energy is applied from a first artery to a second artery.

In some embodiments of the invention, energy is applied from the ureter and/or renal pelvis to treat nerves near the corresponding artery (e.g., right ureter to right renal artery, left ureter to left renal artery).

In some embodiments, energy is applied from an artery to tissues near a vein.

In some embodiments, energy is applied from a first vein to a second vein.

In some embodiments of the invention, the US emission element is introduced into the ureter and/or renal pelvis using the urethral approach.

In some embodiments of the invention, energy is applied from the lumen with blood flowing therethrough. Optionally, no external cooling devices are used, for example, cooling of the US emission element is accomplished by the blood flow.

In some embodiments, to cool the US emission element inside the ureter, flow of a suitable cooling fluid (e.g., saline) is introduced, for example, using a tube. The flow of urine from the kidney alone may be insufficient to adequately cool the US emission element.

Exemplary Lumen Support Device

FIGS. 3A-D illustrate an expandable device used to maintain a patent lumen, for example, a renal vein 302, in accordance with an exemplary embodiment of the invention. The expandable device is used to keep the lumen open to an energy emission element to be inserted into the lumen and US energy to be transmitted from the vein to the target tissue, for example, to a wall and/or tissue near a renal artery 304. Alternatively, the device is used to keep open a renal artery, for example, a stenotic artery secondary to atherosclerosis (e.g., renal artery stenosis). In such a case, energy can be applied from within the artery, through the propping device to treat the arterial wall and/or surrounding tissue. In some embodiments, the device is used to keep the energy emission element at a safe distance from the lumen wall. In some embodiments, the device is deployed to allow enough blood to flow over the ultrasonic emission element of the catheter to cool the element.

Figure 3A:
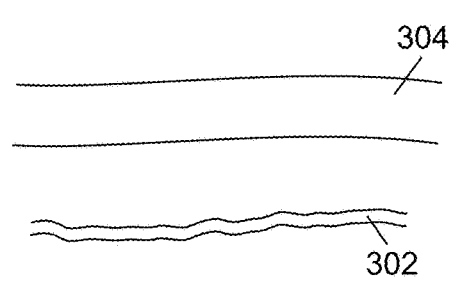

FIG. 3A illustrates renal vein 302 in the compressed state, for example, the usual state of vein 302 as would be encountered during the procedure. In practice, a catheter cannot be introduced into vein 302, or there is difficulty in introducing the catheter into compressed vein 302. Furthermore, even if the catheter can be inserted, compressed vein 302 might not allow enough blood to flow over the ultrasonic emission element of the catheter to cool the element.

Figure 3B:
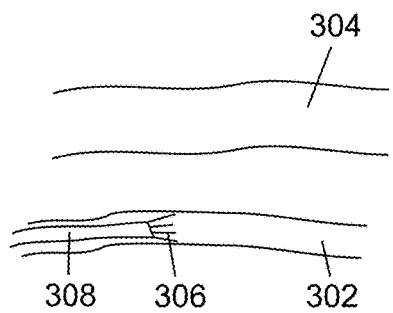

FIG. 3B illustrates the introduction of an expandable device into compressed vein 302. Optionally, the expandable device is a propping device 306. In some embodiments, propping device 306 is deployed by withdrawing a sheath 308 overlaying propping device 306. In some embodiments, propping device 306 is deployed by using a lever, for example a lever in the catheter handle. Optionally or additionally, the expandable device is self expanding, for example, made out of nitinol, or expandable balloon made out of stainless steel. Optionally or additionally, the propping device is collapsible, for removal from the patient after the treatment. Alternatively, the expandable device is a balloon, or a mechanical device which is able of changing its geometrical shape actively or passively (e.g., collapsible stent), or other suitable expandable device can be used. In some embodiments, the expandable device is unidirectional or multidirectional, for example distancing the energy emission element from one or more vessel walls, for example 40, 90, 180, 270, 360 degrees or intermediate values, circumferentially. In some embodiments, the expandable device is distal to the energy emission element. In some embodiments, at least a portion of the energy emission element is covered by the expandable device. In some embodiments, the propping device centers the catheter within the vessel.

Figure 3C:
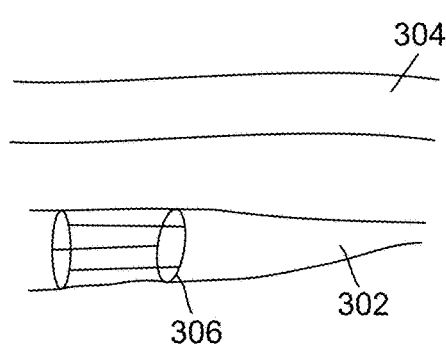

FIG. 3C illustrates the deployed propping device 306 in vein 302. In an exemplary embodiment of the invention, propping device 306 expands to a diameter sufficiently large to accommodate the catheter with the US emission element, while leaving room for blood flow sufficient to cool the US element. For example, about 4 mm to 20 mm, or about 5 mm to 15 mm, or about 5 mm to 10 mm, or about 6 mm to 8 mm, or other smaller, intermediate or larger ranges are used. Expanded propping device 306 expands at least a portion of vein 302 to the selected diameter. In some embodiments, propping device 306 is deployed within a second lumen, for example in artery 304.

In an exemplary embodiment of the invention, propping device 306 expands to a substantially circular cross sectional shape, although other shapes are possible, for example, rectangular, oval. Some propping device shapes might shapes the vein wall to be relatively closer to the target tissue over other propping device shapes.

In an exemplary embodiment of the invention, propping device 306 has a length of about 10 mm, 20 mm, 30 mm, or other smaller, intermediate, or larger lengths.

In an exemplary embodiment of the invention, propping device 306 is designed with alternating struts held together by rims at the top and/or bottom. Optionally, the distance between struts and/or the rim forms a gap sufficiently large to allow the ultrasound beam to be emitted through the gap without interfering with the propping device. For example, the gap between struts is at least about 6 mm, or at least about 8 mm, or at least about 10 mm, or at least about 12 mm, or at least about 14 mm, or other smaller, intermediate or larger sizes. Optionally, the device contains gaps to allow treatment of all the tissues around the arterial wall. Optionally, the thickness of the strut is no more than about 0.1 mm, or 0.3 mm, or 0.5 mm, or 0.7 mm, or 1.0 mm, 1.2 mm, or other smaller, intermediate or larger thicknesses.

Figure 3D:
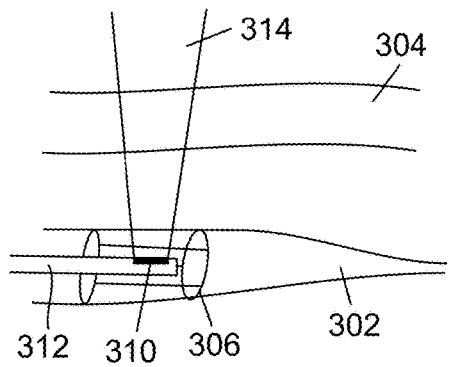

FIG. 3D illustrates a catheter 312 with an US emission element 310 positioned within propping device 306. Optionally, US energy 314 is applied through propping device 306, for example, directed towards artery 304. Optionally, energy 314 is directed through gaps in cells of propping device 306 and/or between struts of propping device 306. Alternatively, US element 310 is positioned proximal or distal to propping device 306.

In an exemplary embodiment of the invention, propping device 306 is arranged so as not to interfere with the ultrasound beam directed through the propping device 306 to the arterial wall and/or surrounding tissue. Alternatively, some interference is allowed, but the interference is insufficient to transfer heat from propping device 306 to the intima in an amount sufficient to damage the intima.

In an exemplary embodiment of the invention, propping device 306 in the expanded state has a diameter that provides for a clearance of at least about 0.5 mm between US emission element 310 and the lumen wall, or a clearance of at least about 1 mm, at least about 1.2 mm, at least about 1.4 mm, at least about 1.6 mm, at least about 1.8 mm, at least about 2.0 mm, or other smaller, intermediate or larger distances are selected. The clearance distance is selected based on selected blood flow (e.g., to cool the wall and/or emission element). For example, relatively higher distances allow for relatively higher blood flow and relatively higher cooling.

Alternatively, in the case of using an expandable device such as a balloon, the balloon is expanded proximally or distally to the US emission element.

In some embodiments, two devices are used. One helps the catheter enter the lumen, and the second device helps maintain a distance from the emission element to the wall. Examples of suitable distancing devices are described with reference to PCT/IB2011/054638, incorporate herein by reference in its entirety.

In some embodiments, propping device 306 maintains a distance from the emission element to the wall in several directions, for example to allow emission in multiple directions, simultaneously and/or without moving and/or rotating the catheter.

In some embodiments, propping device 306 is sized for use in other veins.

Figure 3E:
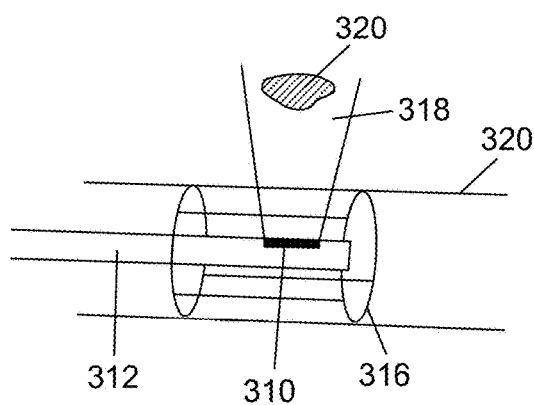

FIG. 3E illustrates treatment by the catheter placed within an artery (e.g., renal artery 320) to treat tissue near the artery. Energy is delivered across a stent 316 positioned in the artery. Optionally, stent 316 is arranged to not intersect US energy 318 applied from within artery 320 to a target 322 in the arterial wall or surrounding tissues. Alternatively, stent 316 struts intersect US energy 318, but energy 318 is applied to treat regions beyond stent 316 without damaging tissues in direct contact with stent 316 (e.g., intima). For example, standard off the shelf stents may be used with some embodiments.

In some embodiments, stent 316 has been inserted into artery 320 in an earlier and separate procedure, for example, to treat renal artery stenosis. Alternatively, stent 316 can be inserted into artery 320 during the denervation procedure, for example, to treat both renal artery stenosis and denervation. Alternatively or additionally, stent 316 is inserted into artery 320 to prop open and/or expand the diameter of artery 320 to allow treatment, for example, if artery 320 contains plaque and/or is tortuous.

In some embodiments, propping device 306 is similar to stent 316, with stent 316 being biased to exert a force against the lumen wall that is relatively stronger than the force propping device 306 would exert against the wall. For example, stent 316 is biased to open up a stenosed artery and/or open an artery with plaque. For example, the force exerted by propping device 306 is relatively weaker, required to provide shape to the wall of the vein and prevent collapse of the walls, without damaging the walls.

In some embodiments, heating the US absorbing stent by the US emission element causes the stent to heat and form a treatment region in tissue (e.g artery intima or media) in contact with and/or adjacent to the stent.

In some embodiments, restenosis is prevented and/or reduced on propping device 306 by heating smooth muscle cells on the arterial wall. Optionally, US treatment parameters are modified to induce damage to smooth muscle cells in the media of the arterial wall in order to prevent re-stenosis formation. Possible mechanisms for prevention or decrease in re-stenosis formation are by suppression of smooth muscle cells proliferation via heat shock proteins (HSPs). Additionally, heating of the adventitia may cause damage to the vasa vasorum and reduction in blood supply to the artery wall, which would result in reduced metabolism in the artery wall. Finally, collagen denaturation in the artery wall would reduce the possibility of neointima formation.

In some embodiments, the propping device is coated with chemicals (e.g., therapeutic drugs). Optionally, the US energy emitted from the catheter releases the chemicals to the tissue in contact with the stent. Alternatively, the drugs are released from the propping device without the US energy trigger.

In some embodiments, the propping device is made from an US absorbing material (e.g., polymer, or polymer-coated metal). Optionally, application of the US energy from the catheter helps and/or triggers in propping the stent open. For example, the propping device is made from a shape memory alloy (e.g., Nitinol) that is set with a temperature above the blood temperature. Applying US energy to the propping device heats up the device to above the blood temperature, thereby causing expansion of the propping device. Additionally or alternatively, heating the US absorbing device by the US emission element makes a hole in the propping device. For example, if the propping device is coated with collagen, heating the collagen by applying US energy causes denaturation of the collagen. The denatured collagen is broken down by the body, forming the hole. Potentially, the hole enables blood flow, for example, to a small lumen bifurcating from a larger lumen.

Exemplary US Delivery

Figure 4A:
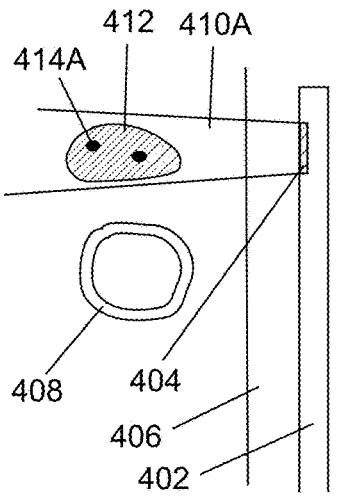
Figure 4B:
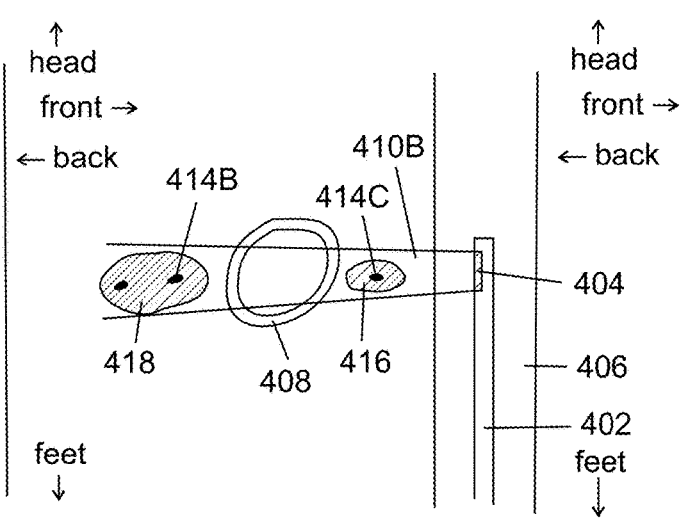
Figure 4C:
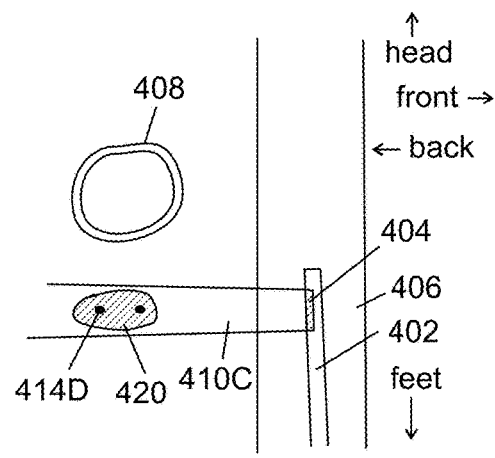
Figure 4D:
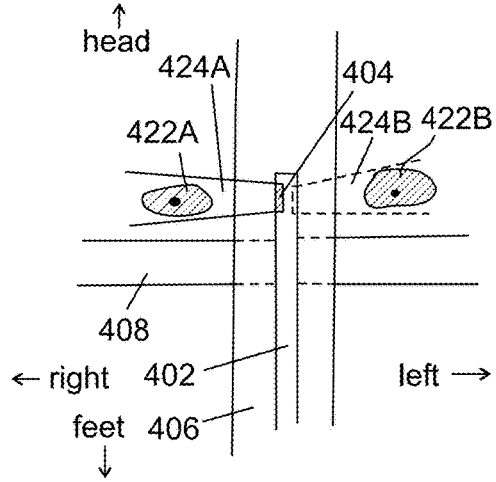

FIGS. 4A-D illustrate positioning of a catheter 402 mounted ultrasound emission element 404 inside a vein, in accordance with an exemplary embodiment of the invention. Selective positioning is used to obtain one or more selected treatment regions anywhere around an artery 408. For example, at about 0 degrees, or at about 15 degrees, or about 30 degrees, or at about 45 degrees, or at about 60 degrees, or at about 90 degrees, or about 120 degrees, or at about 180 degrees, or at about 210 degrees, or at about 270 degrees, or at about 300 degrees, or other smaller, intermediate or larger locations measured in degrees around artery 408. Potentially, the methods allowed for treatment of nerves are more than one location around the artery, for example, at opposite sides of the artery. The figures refer to an anatomical orientation in which the vein and the artery are substantially perpendicular to one another. FIGS. 4A-C show a cross section through the anatomy of the patient as seen from the side (e.g., sagittal plane). FIG. 4D is a cross section as seen from the front (e.g., coronal plane). In an exemplary embodiment of the invention, catheter 402 is positioned inside an inferior vena cava 406, with US energy directed towards a right renal artery 408 and/or to tissues surrounding artery 408. Other arteries can be treated from other veins using the principles described herein.

In an exemplary embodiment of the invention, US energy is applied without causing damage to the intima of artery 408 and/or vena cava 406.

FIG. 4A illustrates US element 404 positioned relatively above artery 408 (e.g., cranially, or towards the head). Optionally, US beam 410A is applied to obtain treatment 412 relatively above artery 408. In practice, area 412 is selected to contain one or more renal artery nerves 414A, for example, in the adventitia and/or perivascular tissue surrounding the artery.

FIG. 4B illustrates US element 404 positioned relatively directly facing artery 408. Optionally, US beam 410B is applied to obtain treatment area 416 relatively in front of artery 408 (e.g., between artery 408 and element 404). Alternatively, US beam 410B is applied to obtain a treatment area 418 that is relatively behind artery 408 (e.g., opposite the location of area 416 relative to artery 408). In practice, areas 416 and/or 418 are selected to contain one or more renal artery nerves 414B-C. The treatment areas can be near the vein, near the artery, or near both (e.g., about equal distances).

FIG. 4C illustrates US element 404 positioned relatively below artery 408 (e.g., caudally, or towards the feet). Optionally, US beam 410C is applied to obtain a treatment area 420 relatively below artery 408. In practice, area 420 is selected to contain one or more renal artery nerves 414D.

In an exemplary embodiment of the invention, the distance between US element 404 and the top or bottom of artery 408 is no more than about 1 mm, or about 2 mm, or about 3 mm, or about 4 mm, or about 5 mm, or about 7 mm, or about 10 mm, or other smaller, intermediate or larger distances are used. In an exemplary embodiment of the invention, the distance from US element 404 to the nearest point of artery 408 ranges from about 1 mm to about 20 mm, or about 2 mm to 15 mm, or about 1.5 mm to 10 mm, or about 3 mm to 6 mm, or about 10 mm to 20 mm, or other smaller, intermediate or larger distances are used.

FIG. 4D illustrates US element 404 positioned relatively above artery 408, the same position as in FIG. 4A, but using the coronal plane. Optionally, US element 404 is rotated relative to artery 408, for example, by applying a torque to catheter 402. Rotation of element 404 can apply US beam substantially parallel to the length of artery 408. For example, in a first position US beam 424A is applied to form area of damage 422A, and in a second position US beam 424B is applied to form area of damage 422B.

FIGS. 5A-C illustrate positioning of a catheter 502 mounted ultrasound emission element 504 inside a vein, in accordance with an exemplary embodiment of the invention. Selective positioning is used to obtain selected treatment regions around an artery. The figures refer to an anatomical orientation in which the vein and the artery are substantially parallel to one another. FIGS. 5A-B show a cross section through the anatomy of the patient as seen from the side (e.g., sagittal plane). FIG. 5C is a cross section as seen from the front (e.g., coronal plane). In an exemplary embodiment of the invention, catheter 502 is positioned inside a left renal vein 506, with US energy directed towards a left renal artery 508 and/or to tissues surrounding artery 508. Other arteries can be treated from other veins using the principles described herein.

In an exemplary embodiment of the invention, US energy is applied without causing damage to the intima of artery 508 and/or to the intima of vein 506.

FIG. 5A illustrates US beam 510A directed to apply energy relatively above artery 508 (e.g., cranially, or towards the head). In an exemplary embodiment of the invention, catheter 502 is rotated to position element 504, for example, by applying a torque to catheter 502. Optionally, an area of damage 512A is formed by the US energy relatively above artery 508.

FIG. 5B illustrates US beam 510B directed to apply energy towards the center of artery 508. In an exemplary embodiment of the invention, the US energy forms an area of damage 512B relatively in front of artery 508 (e.g., between artery 508 and US element 504). Alternatively, an area of damage 512C is formed relatively behind artery 508.

In some embodiments of the invention, US element 504 is rotated from about −60 degrees to about +60 degrees relative to artery 508 (0 being defined as element 504 facing the center of artery 508), or from about −45 to +45 degrees, or about −30 to about +30 degrees, or about −15 to about +15 degrees, or other smaller, intermediate or larger arc lengths. Optionally, element 504 is rotated in a stepwise manner, each time a turn of about 15 degrees, about 30 degrees, about 45 degrees, about 60 degrees, or other smaller, intermediate or larger angles.

FIG. 5C illustrates displacement of US emission element 504 proximally (shown in solid lines) and distally (shown in dotted lines). Areas of damage are selectively caused proximally (e.g., area 512C) and/or distally (e.g., 512D) relatively along artery 508.

In an exemplary embodiment of the invention, rotating catheter and/or displacing catheter (proximally or distally) causes the US beam produced by the US emission element to scan above, across and/or below the artery, potentially to form contiguous treatment regions. Alternatively, energy is applied stepwise, potentially to form spaced apart regions. For example, to form a first region at the 90 degree position around the vein, the catheter is rotated to point to the middle of the vein. Energy is applied to reach the target. For example, to form a second region at the 270 degrees position around the vein, the catheter is left in place, but the energy parameters are changed. For example, the frequency is increased. For example, to form a third region at the 0 degree position, the catheter is rotated counterclockwise by about 60 degrees, and energy is applied. For example, to from a fourth region at the 180 degrees position, the catheter is rotated clockwise by about 120 degrees and energy is applied.

Optionally, US beam 410A is applied to obtain a treatment area 412 relatively above artery 408. In practice, area 412 is selected to contain one or more renal artery nerves 414A, for example, the adventitia and/or tissue surrounding the artery.

Exemplary Embodiment-Carotid Denervation

Figure 2B:
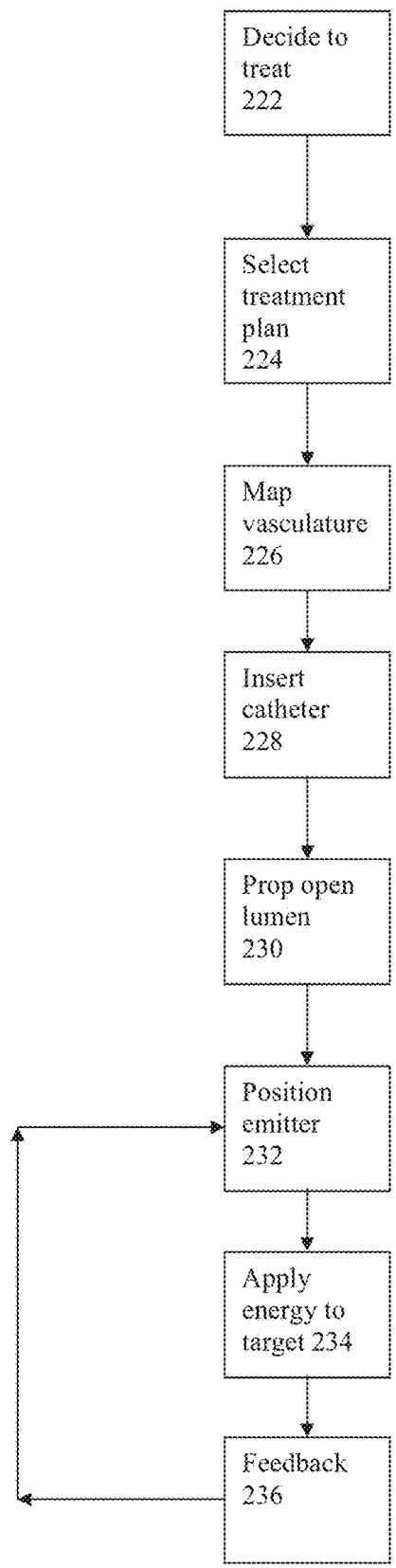

FIG. 2B shows a method of using ultrasound for treating tissues surrounding a lumen and/or in the lumen wall by application of energy from within the lumen. Optionally, the artery is an internal carotid artery. Optionally or additionally, nerves in the perivascular tissue around the internal carotid artery are selectively treated, for example to treat overactive carotid sinus baroreceptors. The baroreceptors detect changes in blood pressure, causing the brain to send compensatory signals. Improper signals from the brain lead to symptoms such as fainting (e.g., carotid sinus syndrome).

FIG. 9 is a schematic of a right internal carotid artery 902, useful for practicing some embodiments of the invention. A carotid sinus 910 (comprising baroreceptors in the wall thereof) is located at internal carotid artery 902 above a bifurcation of a common carotid artery 906 into internal carotid 902 and an external carotid artery 908.

Optionally, at 222, the decision to treat the patient by treatment of tissue surrounding the carotid artery is made, in accordance with some embodiments of the invention. Optionally, the decision is to treat the patient by treating tissues surrounding the internal carotid artery to disconnect (e.g., disruption of signals) baroreceptors in the carotid sinus from the brain, for example, the carotid sinus nerve (or the carotid branch of the glossopharyngeal nerve).

Some not necessarily limiting examples of clinical indications include; one or more related signs and/or symptoms related to carotid sinus syndrome; patients contra-indicated for, or that failed a pacemaker; patients unsuitable for carotid adventitial stripping surgery.

Optionally, at 224, the treatment plan is selected. In some embodiments, the treatment plan comprises selectively targeting nerves in the adventitia and/or perivascular tissue at one or more regions surrounding the internal carotid artery. Optionally, the regions are spaced apart. Alternatively or additionally, the carotid sinus is selected for treatment.

In an exemplary embodiment of the invention, the adventitia is selectively targeted for damage.

Optionally, one side is treated, the left or the right carotid artery. Alternatively, both sides are treated.

In some embodiments, sufficient treatment regions are planned to prevent propagation of 100% of the signals passing through the carotid artery and/or carotid sinus adventitia (e.g., carotid sinus nerve). Alternatively, at least some signaling is selectively preserved, for example, signaling is reduced by about 90% from the original signal, or about 80%, or about 70%, or about 50%, or about 30%, or other smaller, intermediate or larger percentages are selected. Alternatively or additionally, the transmitted signals are weakened; for example, the amplitude of the signal is reduced.

Optionally, at 226, the vasculature of the carotid bifurcation and/or internal carotid artery is evaluated. Optionally, the presence of a plaque is determined, for example, by Doppler ultrasound. Patients with plaques may require deployment of a stent to increase the size of the lumen. Optionally, the presence of a patent Circle of Willis is evaluated (to ensure collateral blood flow from both internal carotid arteries to the brain), for example, by CT and/or Doppler. Patients may require collateral blood flow for safety reasons.

Optionally at 228, the catheter is inserted into the vascular and threaded into the internal carotid artery. Not necessarily limiting examples of percutaneous access sites include; femoral artery, radial artery.

Optionally at 230, the lumen of the internal carotid artery is expanded to allow the catheter to be inserted. For example, the internal carotid artery is stenotic and/or contains a plaque. In some embodiments, a specially designed stent is used, for example, as described in the section "EXEMPLARY LUMEN SUPPORT DEVICE". Alternatively, an off the shelf stent can be used, for example, a stent used to treat stenotic carotid arteries.

At 232, an energy emission element (e.g., ultrasound transducer 912) is positioned within carotid sinus 910. Optionally, the US element is positioned to form the selected treatment regions in accordance with the selected treatment plan.

At 234, energy is applied to the wall of carotid sinus 910 and/or the lower segment of internal carotid artery 902, for example, from the bifurcation to about 1 cm above the bifurcation, or about 2 cm, or about 3 cm, or about 4 cm, or about 5 cm above the bifurcation, or other smaller, intermediate or larger distances.

In some embodiments of the invention, energy is selectively applied to treat the artery wall, surrounding tissue and/or nerves. Optionally, the nerves in the adventitia are sufficiently treated to decrease signal transmission.

In some embodiments, the intima is not damaged by the treatment. Optionally or additionally, the media is not damaged by the treatment.

FIGS. 10A-D are some not necessarily limiting examples of damage patterns, in accordance with some embodiments of the invention. For clarity, the carotid sinus and/or portions of the internal carotid artery are shown as unrolled.

Figure 10A:
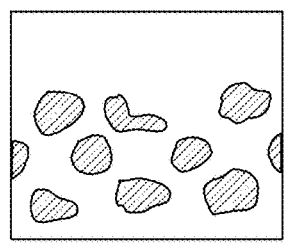

FIG. 10A is an example of a checkerboard pattern of spaced apart treatment areas.

Figure 10B:
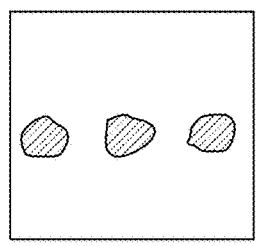

FIG. 10B is an example of alternating spaced apart treatment areas.

Figure 10C:
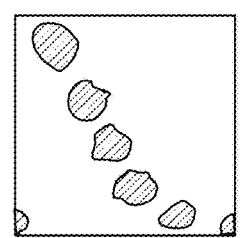

FIG. 10C is an example of treatment areas spaced apart along the length of the artery to cover the circumference.

Figure 10D:
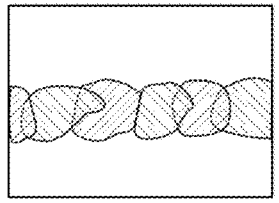

FIG. 10D is an example of overlapping and/or contiguous damage areas, for example, using the patterns of FIGS. 10A-C.

In some embodiments, the tissue damage pattern includes a circumferential damage.

In an exemplary embodiment of the invention, the carotid artery wall can be treated with relatively higher intensities, for example, relative to treatment of the renal artery wall.

In an exemplary embodiment of the invention, the intensity is, for example, about 10 Watt/cm^2 to about 50 Watt/cm^2, or about 20 Watt/cm^2 to about 40 Watt/cm^2, or about 10 Watt/cm^2 to about 30 Watt/cm^2, or other smaller, intermediate or larger intensities.

In an exemplary embodiment of the invention, the times are, for example, about 1 second to about 60 second, or about 5 sec to about 30 sec, or other smaller, intermediate or larger times are selected.

Optionally or additionally, the intensity and/or times are, for example, about 5% to about 50% higher and/or longer relative to the renal artery wall, or for example, about 10% to about 40%, or about 10% to about 30%, or about 15% to about 20%, or other smaller, intermediate or larger percentages.

Alternatively or additionally, the highest intensity of the transmitted energy used to treat nerves in the carotid artery is lower relative to the energy applied in the renal artery to treat renal nerves. For example, the intensity is reduced by about 5%-20%, or by about 5%-10%, or by about 10%-15%, or by about 10%-20%, or other smaller, intermediate or larger reductions are used.

In some embodiments, energy is applied to selectively block the vasa vasorum of the adventitia. Potentially, blocking the vasa vasorum reduces the blood supply to the adventitia and/or nerves located therein, disrupting signal propagation through the nerves.

Optionally, at 236, feedback is obtained, for example, to evaluate the effectiveness of the treatment. Optionally, the feedback evaluates the ability of the nerves to conduct signals, for example, by performing a manual carotid massage and checking changes in blood pressure and/or pulse rate. Alternatively or additionally, the feedback evaluates the tissue damage, for example, by analysis of US echoes.

Optionally, one or more steps are repeated, for example, the transducer is repositioned as in 222 and/or energy is applied again as in 224. For example, to re-treat the same region and/or treat another region.

A potential advantage of the method to treat the carotid sinus nerve, is that the method can be performed even in patients contra-indicated for surgery, for example, patients with plaques and/or at risk of a stroke, as the method does not require touching the wall and/or does not block blood flow to the brain. In some cases, patients with lack of blood collateral blood flow (e.g., incomplete Circle of Willis) can be safely treated.

Exemplary Embodiment-Limb Vessel Denervation

Figure 2C:
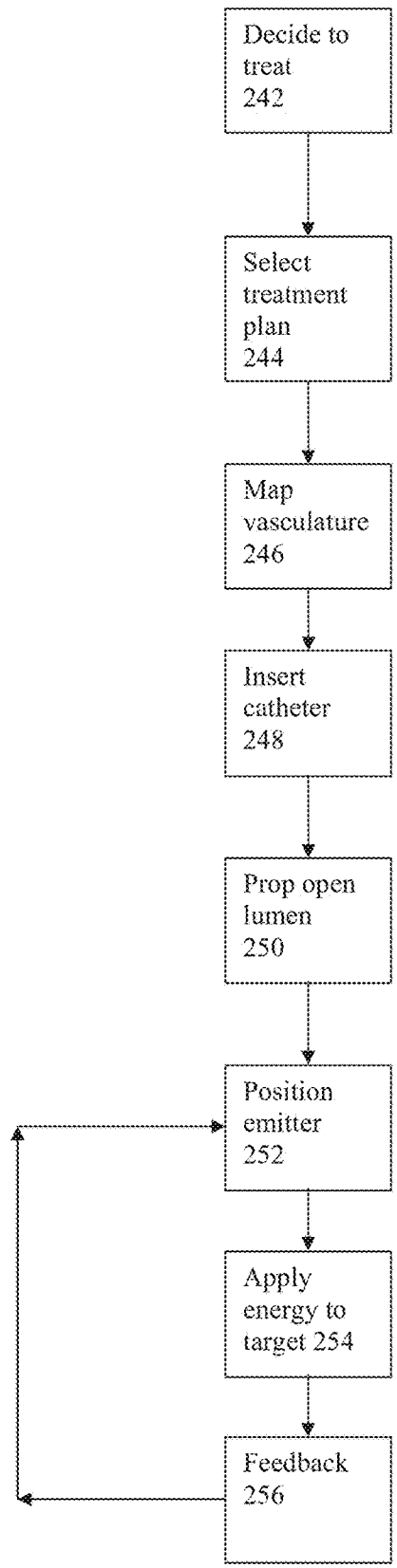

FIG. 2C shows a method of using ultrasound for treating of tissues surrounding a lumen in a limb, for example, the femoral artery and/or vein in the leg, brachial artery in the arm. Optionally or additionally, nerves in the wall of the limb artery are selectively treated, for example to treat an overactive sympathetic nervous system. Inventors hypothesize, that reducing the activity of the sympathetic nerves in the vessel wall will dilate the end vessels (e.g., where arterial blood meets venous blood) to allow more blood to flow to the limb.

To help understand the method, FIG. 11 is a schematic, showing a cross section through a right thigh of a patient, illustrating the relative positions of a femoral artery 1102, a femoral vein 1104 and a femoral nerve 1106. In some cases, femoral artery 1102 contains a plaque 1110 and/or calcified walls 1112. A catheter 1108 having an energy emission element 1114 (e.g., ultrasound) is positioned inside the stenotic lumen. In some embodiments, a pencil beam of unfocused ultrasound 1116 is directed to treat a region 1118 containing one or more nerves in the arterial wall (e.g., adventitia) and/or surrounding tissue. Optionally, beam 1116 traverses plaque 1110 and/or calcification 1112 to treat region 1118. In some embodiments, beam 1116 is adjusted to be safely used around the circumference of artery 1102, for example, beam 1116 will not damage nerve 1106. Alternatively, beam 1116 is pointed away from nerve 1106, for example the presence of nerve 1106 is first mapped and/or detected (e.g., using fluoroscopy and/or ultrasound).

Alternatively, in some cases, beam 1116 is pointed to treat nerves that are bunched together, for example, to treat nerve 1106.

In some embodiments of the invention, the described method is used to perform renal denervation through a plaque in the renal artery.

A potential advantage of the described method is to deactivate nerves (e.g., sympathetic nerves) in an arterial wall, for example, to increase blood flow to the lumen (e.g., to treat a diabetic foot) and/or to reduce kidney norepinephrine levels (e.g., to treat hypertension). Potentially, the described method provides for treatment of the wall through the plaque, without causing the vessel and/or plaque to rupture, for example, a possible risk with an expansion balloon.

Optionally, at 242, the decision to treat is made for example, by the physician.

Some not necessarily limiting examples of clinical indications for the treatment include; critical limb ischemia, repeated infections, gangrene, wounds that do not heal, and/or risk of amputation, due to, for example, peripheral arterial disease, occlusive pathologies, diabetes. In some cases, end organ damage due to hypertension is an indication (e.g., kidney damage). In some cases, a possible indication is prevention of exaggerated vasoconstriction to cold, for example Raynaud's phenomenon.

Some not necessarily limiting treatment outcomes include; vasodilation of the treated blood vessel and/or vessels innervated by the treated nerves, relatively increased collateral blood flow (more blood can help in healing the limb), relatively decreased blood pressure in the treated lumen and/or downstream vessels, decrease in symptoms related to sympathetic neural activity (e.g., sweating), reduction in pain. In practice, the following scenarios might be observed; all of the treatment outcomes occurring together; decrease in blood pressure and vasodilation occurring together.

In some embodiments, the magnitude and/or percent change in parameter (e.g., vasodilation, blood flow, blood pressure, sweating, pain reduction) are selected according to the amount of tissue treated surrounding the lumen. For example, according to a table of correlation values correlating the percent change in parameter with the amount of tissue treated and/or with treatment parameters (e.g., frequency, intensity, time).

Optionally, at 244, the treatment plan is selected, for example, by a physician performing the treatment.

In a non-limiting example the treatment plan comprises:

Selecting the affected leg for treatment (left or right). If two legs need treatment, one can be performed at one time.

Selecting the level of the major blood artery for treatment. For example, treating at the level of the external iliac, the level of the femoral artery and/or the level of the popliteal artery.

Selecting the number of treatments per level, for example, 4.

Selecting the pattern of treatments per level, for example, spaced apart by 90 degrees substantially at the same level (e.g., by rotating the catheter without axial displacement).

Selecting the treatment parameters per location, for example, about 30 seconds, about 20 Watt/cm^2, about 20 Mhz.

In some embodiments, the treatment is selected to selectively reduce activity of sympathetic nerves, for example, nerves in the wall and/or surrounding tissue of the blood vessel. For example, about 100% of the nerves are treated to prevent signals from passing therethrough, or about 90%, about 80%, about 70%, about 50%, about 30%, about 20%, or other smaller, intermediate or larger percentages.

In some embodiments, the treatment plan is selected to not damage nearby non-sympathetic nerves (e.g., motor and/or sensory), for example, the femoral nerve which runs in close proximity to the femoral artery. Optionally, the treatment is selected to be confined to the arterial wall, for example, no more than about 1.5 mm from the intima, or about 2 mm, or about 2.5 mm, or about 3 mm, or about 4 mm, or about 5 mm, or about 7 mm, or other smaller, intermediate or larger distances are selected.

Optionally, at 246, the limb vessels are mapped to provide a baseline of the state of the patient before treatment and/or to adjust the treatment parameters accordingly. In some embodiments, the blood flow through the limb is evaluated, for example, using the Ankle Brachial Pressure Index. Optionally, the arterial wall is evaluated for stenosis (e.g., due to plaques), for example, by Doppler. Optionally or additionally, the arterial wall is evaluated for the presence of calcification, for example, by ultrasound.

In some embodiments, the presence of plaque and/or calcification is used to adjust the treatment plan.

In an exemplary embodiment of the invention, relatively higher intensities and/or relatively higher treatment time durations are used to treat nerves beyond the plaque and/or calcified wall (e.g., in the wall of the vessel). The values are higher than the highest settings that would allowable if the lumen did not contain calcified walls and/or plaque.

In an exemplary embodiment of the invention, contact between the US emission element and the plaque and/or vessel walls is prevented. Optionally, the distancing device (e.g., as described herein and/or in the related applications) is used to prevent contact.

In an exemplary embodiment of the invention, treatment is selected to not damage the intima contacting the plaque.

In an exemplary embodiment of the invention, the intensity and/or times are, for example, about 10% to about 50% higher and/or longer relative to the same vessel without plaque, or for example, about 10% to about 40%, or about 10% to about 30%, or about 15% to about 20%, or other smaller, intermediate or larger percentages.

Optionally, at 248, the catheter is inserted. In some embodiments, the catheter is sufficiently small to pass through a stenotic lumen. For example, the catheter is sized to fit inside a lumen having a diameter of about 3 mm, or about 4 mm, or about 5 mm, or other smaller, intermediate or larger sizes. Optionally or additionally, the catheter is sufficiently rigid and/or a force sufficiently strong is transmittable so as to force the catheter through the stenotic lumen.

Optionally, at 250, the lumen is propped open. In some embodiments, a stent is first inserted inside the artery, for example, inside a stenotic artery.

Without being bound by theory, the sympathetic denervation potentially increases blood flow through the arterial-venous junction (e.g., at the capillary level), helping to provide blood flow to the areas of the foot that need it more, for example, ulcers. The stent potentially increases blood flow through the blood vessel, which helps increase the blood flow to the capillaries. Both treatments potentially work synergistically to increase blood flow to the limb, but each treatment on its own is also useful.

At 252, the energy emission element (e.g., pencil beam of unfocused ultrasound) is positioned inside the lumen (e.g., artery). Optionally, the US element is positioned within the stenotic region of the artery (e.g., plaque). Alternatively, the US element is positioned proximal to the stenotic region (e.g., relative to blood flow). Alternatively, the US element is positioned distal to the stenotic region.

At 254, energy is applied to the lumen wall by the energy emission element. Optionally, energy is applied anywhere along the circumference of the artery. Alternatively, energy is prevented from being applied towards large nerves passing in close proximity to the artery, for example, the femoral nerve.

In an exemplary embodiment of the invention, the ultrasound energy passes through the plaque on the way to the target tissue at the arterial wall. Alternatively or additionally, the ultrasound energy passes through calcification on the way to the target tissue.

In an exemplary embodiment of the invention, US echoes are used for imaging and/or detection of the calcification, according to the returning energy. Such imaging can be used, for example, for changing the treatment location and/or for modification of US treatment parameters (e.g. intensity, time duration).

Optionally, at 256, feedback is used to evaluate the treatment. Optionally, a parameter associated with the treatment is measured before the procedure. Optionally or additionally, the parameter is measured after the procedure and compared with the pre-treatment parameter value, for example, the comparison is against the selected reduction or increase in the parameter value.

Some not necessarily limiting examples of parameters include; norepinephrine (NE) levels in the limb, blood flow in the limb, healing of wounds in the limb.

In some embodiments, the treatment is repeated, optionally based on feedback. For example, the patient is brought back for treatment of the same limb if the blood flow is still inadequate.

Exemplary Embodiment-Heart Denervation

Figure 2D:
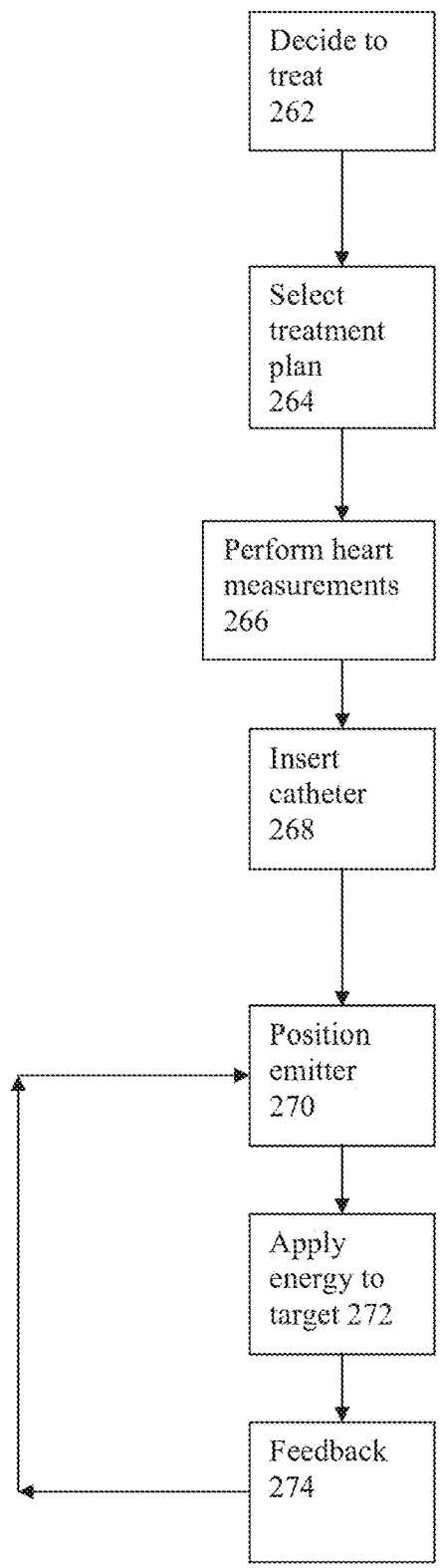

FIG. 2D shows a method of using ultrasound for treating of tissues inside the heart, for example, the wall of the left atrium at the ostium of one or more pulmonary veins. In an exemplary embodiment of the invention, energy is applied to reduce and/or stop conduction of contraction signals along the wall of the heart, for example, by myocardial cells. Optionally, treatment of the myocardium treats atrial fibrillation. Inventors hypothesize that selectively damaging tissue prevents conduction of abnormal contraction signals, thereby reducing or preventing abnormal heart contractions.

To help understand the method, FIGS. 16A-B are schematics, showing the anatomy of the heart and possible treatments, in accordance with an exemplary embodiment of the invention. FIG. 16A is a cross sectional view of the heart, showing pulmonary veins draining into a left atrium. To treat atrial fibrillation (e.g., abnormal contraction signals originating from the pulmonary veins), the ostium of the pulmonary vein is treated to prevent abnormal signal conduction from the vein to the atrium by treating tissues at location 'C'.

FIG. 16B illustrates a catheter 1604 having an US element 1602 optionally positioned in a left atrium 1606. Optionally, US element 1602 is positioned at or near ostium 1612 of one or more pulmonary veins 1614.

In some embodiments, a guidewire 1652 (e.g., threaded into pulmonary vein 1614 is used to help guide and position catheter 1604. Optionally or additionally, a distancing device 1652 (e.g., as described with reference to PCT/IB2011/054638) is used to reduce and/or prevent contact between US element 1602 and heart wall 1608.

Optionally, US beam 1618 forms one or more treatment regions 1616A-F in heart wall 1608. The layers of wall 1608 (from inside to outside) are endocardium 1622, myocardium 1620, epicardium 1662 and pericardium 1660. Optionally, regions within the atrium are treated, for example, as illustrated by treatment region 1616D. Alternatively or additionally, regions within the atrium around one or more pulmonary veins are treated, for example, as illustrated by treatment regions 1616A-C. Alternatively or additionally, regions within a branch of pulmonary veins are treated, for example, as illustrated by treatment regions 1616E-F. Alternatively or additionally, regions inside the pulmonary veins are treated, for example, as represented by treatment regions 1616G-H. Alternatively or additionally, treatment regions include endocardium 1622, for example, as represented by treatment region 1616I.

Optionally, at 262, a decision to treat a patient is made, for example, by the physician. In a non-limiting example, an indication for treatment is arrhythmia originating from a defined location, for example, atrial fibrillation triggered or caused by signals from the pulmonary veins.

Optionally, at 264, a treatment plan is selected, for example, by the physician. In a non-limiting example, the treatment plan comprises:

Gross anatomical location of the treatment regions: Optionally, forming a substantially contiguous ring around the ostium so that signals from the pulmonary veins are unable to enter into the left atrium (cross section of the ring shown in FIG. 16B). For example, one large ring can be formed around the ostiums of the 4 pulmonary veins, or rings can be formed around individual ostiums of each pulmonary vein. Alternatively, the ring is not entirely continuous, but the gaps don't allow enough signal to travel through to trigger the arrhythmia. Alternatively or additionally, treatment is around the inside of one or more pulmonary veins. For example, 100% of heart tissue around the ostium is treated, or 100% of tissue forming an enclosed ring on the heart wall is treated, or at least 90% of the areas, or at least 80%, or at least 70%, or other smaller, intermediate or larger percentages. Alternatively, non-ring patterns can be formed, for example, straight or zig-zagging lines, for example to block mapped irregular electrical activity.

Fine anatomical location and/or size of the treatment regions: Optionally, the treatment regions are selected to not damage the endocardium. Optionally or additionally, the treatment regions are selected to damage most of the entire thickness of the myocardium. Optionally, a gap is left between the damage area and the endocardium, for example, the gap is no more than about 0.01 mm, or 0.1 mm, or 0.3 mm, or 0.5 mm, or 0.7 mm, or 1 mm, or other smaller, intermediate or larger sizes. Optionally or additionally, some damage into the pericardium is allowed (e.g., in order to achieve the damage to the myocardium), for example, no more than about 0.5 mm, or about 1 mm, or about 2 mm, or about 3 mm, or about 5 mm, or other smaller, intermediate or larger distances.

Type of damage: Optionally, the treatment regions are selected to damage the entire thickness of the myocardium so that the myocardial cells are unable to transmit contraction signals through the damage region. For example, the myocardial cells are killed by the US energy. In an exemplary embodiment of the invention, about 100% of cells within the treatment region are killed, or at least 90%, at least 80%, at least 70%, at least 60%, or other smaller, intermediate or larger percentage of cells.

Frequency: The frequency is, for example, about 15 Mhz-40 Mhz, or about 15 Mhz-20 Mhz, or about 20 Mhz-30 Mhz, or about 15 Mhz-30 Mhz, or other smaller, intermediate or larger ranges.

Intensity: The intensity is, for example, about 20-50 Watt/cm^2, or about 20-40 Watt/cm^2, or about 25-35 Watt/cm^2, or other smaller, intermediate or larger ranges.

The treatment time per location: for example, about 20 seconds-120 seconds, or about 20-30 seconds or about 30-60 seconds, or about 10-20 seconds, or about 10-30 seconds, or other smaller, intermediate or larger values.

Optionally, at 266, one or more heart measurements are performed.

Optionally, the thickness of the myocardium is measured. Optionally, the parameters are adjusted according to the thickness. For example, the normal myocardium can measure, for example, about 0.6 cm to 1.1 cm. For example, a hypertrophied myocardium can measure, for example, about 1.2 cm, about 1.5 cm, about 2.0 cm or other smaller, intermediate or larger thicknesses. In some cases, if the myocardium is thick, treatment regions may need to be stacked and/or overlapped to cover the entire thickness.

Optionally, the blood flow around the treatment area is measured, for example, to determine if there is adequate blood flow to cool the endothelium and/or the US emission element, or if blood flow is inadequate (e.g., stagnates).

Optionally, the electrical activity in the heart is mapped to determine the path of the abnormal signals, for example, by ECG, invasive electrophysiological mapping or other methods.

Optionally, at 268, the catheter is inserted and threaded to the target location. In one example, the catheter is inserted through the right femoral vein, into the right atrium, and inserted into the left atrium using a transeptal approach. Optionally, the catheter is steerable to allow control over navigation and placement.

In some embodiments, the treatment catheter has a position sensor, and the position and/or orientation are sensed relative to another catheter in the heart to make sure that the treatment catheter is correctly aimed.

In some embodiments, the catheter is positioned inside a coronary artery. Alternatively, the catheter is positioned inside the lungs. Alternatively, the catheter is positioned inside the chest. Alternatively, the catheter is inserted through the chest wall. Alternatively, the catheter is positioned in the adjacent atrium (e.g., right atrium to treat the left atrium). Alternatively, the catheter is positioned inside the pulmonary artery, for example to treat the pulmonary vein.

At 270, the US emitter is positioned to produce the desired treatment region. Optionally, the US emitter is posited with a gap between the emitter and the heart wall, for example, about 1 mm, about 1.5 mm, about 2 mm, about 2.5 mm, about 3 mm, about 4 mm, about 5 mm, or other smaller, intermediate or larger distances. Optionally, the catheter comprises a distancing device to maintain the gap.

At 274, the US emitter applies energy to the heart wall.

In an exemplary embodiment of the invention, the heart wall is treated by treating selective regions. Optionally, the selective regions are treated in small steps (e.g., treat one area, then slightly rotate or axially reposition the catheter and treat another area). For example, the heart wall is treated in 1 step, or 2, or 4, or 5, or 8 or 10, or 15, or 20, or 25, or 30 steps, or other intermediate or larger number of steps.

In some embodiments, the US energy is emitted throughout the cardiac cycle. In such a case, the catheter can be positioned inside the atrium aimed at the wall. Slight movement of the catheter relative to the wall due to the heartbeats is allowed and potentially useful in forming slightly larger areas of thermal damage than if the catheter did not move. Alternatively, the US energy is emitted only during certain phases of the heart beat cycle, for example, during diastole (when the heart is at rest). Optionally, ECG data is synchronized with the US controller to emit the US energy during diastole.

Optionally, at 274, feedback about the treatment is obtained. Optionally, the heart wall is stimulated to determine if the signal conduction path has been blocked by the treatment.

Optionally, the treatment is repeated. For example, the catheter is left in place and the same settings are used to treat the same area again. Alternatively, for example, the catheter is repositioned (e.g., rotated) to treat other regions of the wall, for example, to form the continuous ring. Optionally, the treatment is adjusted, for example, to adjust the location and/or size and/or damage of the treatment regions.

In some embodiments, treatment regions are stacked one on top of another and/or overlap (some lateral displacement is allowed) to cover the entire thickness of the myocardium, for example, as may be required in patients having very thick hypertrophied myocardium that cannot be traversed by a single treatment region.

Exemplary Treatment System

In an exemplary embodiment of the invention, the patient is treated according to the selected treatment parameters. FIG. 14 is a schematic illustration of an exemplary treatment system 1600, according to an exemplary embodiment of the invention. System 1600 provides for the control of the ultrasound treatment and/or monitoring of the treatment using a catheter 1222. It should be noted that system 1600 is not necessarily limiting, and other suitable devices can be used.

In an exemplary embodiment of the invention, an operator (e.g., physician performing the procedure) programs a controller 1602 (e.g., computer) for treatment using a user interface 1604 (e.g., keyboard, mouse, monitor). Optionally, treatment is monitored, for example, by viewing feedback parameters on interface 1604.

In an exemplary embodiment of the invention 1604, comprises a display for displaying, for example, parameters related to treatment, for example, settings and/or real time parameters. Not necessarily limiting examples of displayed items include; time of current treatment, blood temperature, set ultrasound frequency, set ultrasound intensity.

In an exemplary embodiment of the invention, a control port 1606 provides electrical power to electrodes across element 1760 (e.g., piezoelectric), causing element 1760 to vibrate at the set frequency, outputting a selected ultrasound intensity profile.

In some embodiments of the invention, control port 1606 serves as input to controller 1602 from catheter 1222 and/or transducer 1762. Not necessarily limiting examples of input include; imaging data, efficiency information, impedance of transducer, temperature of blood.

In an exemplary embodiment of the invention, catheter 1222 comprises an acoustic element 1760 (e.g., part of transducer 1762) to deliver ultrasonic energy to selectively treat nerves. Optionally, controller 1602 controls the activation of US emission element 1760. In an exemplary embodiment of the invention, transducer 1762 is capable of relatively high intensity ultrasound output. An example of a suitable acoustic emission element is described, for example in PCT application IB2011/054635 by the same inventor (Sverdlik et al.), incorporated herein by reference in its entirety.

In some embodiments, contact between an acoustic element 1760 of transducer 1762 and a wall of a blood vessel (e.g., renal artery), is reduced and/or prevented, for example, by a separation device, for example as described in more detail in PCT application IB2011/054638 by the same inventor (Sverdlik et al.), incorporated herein by reference in its entirety. Optionally, the separation device maintains a distance between element 1760 the blood vessel wall of at least 1 mm.

A zoom-in schematic of transducer 1762 is illustrated. In an exemplary embodiment of the invention, transducer 1762 comprises of a substantially rectangular and planar ultrasound element 1702, for example, a piezoelectric element. A length of element 1702 is, for example, about 1 mm, about 2 mm, about 4 mm, about 6 mm, about 8 mm, about 10 mm, or other smaller, intermediate or larger lengths are used. A width of element 1702 is for example, about 0.2 mm, about 0.6 mm, about 1.0 mm, about 1.4 mm, about 2.0 mm, or other smaller, intermediate or larger widths are used.

In an exemplary embodiment of the invention, electrodes 1704A-B are located on opposite sides of element 1702. Electrodes 1704A-B provide an alternating voltage gradient which causes element 1702 to emit ultrasound energy.

In an exemplary embodiment of the invention, element 1702 is suspended above a support board 1706, for example, by a plurality of attachment areas 1708. In a non-limiting example, areas 1708 are drops of a non-conductive material such as glue.

In an exemplary embodiment of the invention, a gas (e.g., air) bubble 1710 is suspended between element 1702 and board 1706. Without being bound to theory, bubble 1710 provides for element 1702 to vibrate efficiently and emit relatively high intensity ultrasound energy. In an exemplary embodiment of the invention bubble 1710 is not sealed within transducer 1762; upon submersion of transducer 1762 in liquid (e.g., blood, saline) bubble 1710 is formed.

In an exemplary embodiment of the invention, element 1702 is flat.

In an exemplary embodiment of the invention, the ultrasound beam is a pencil beam, for example, emanating from element 1702 without substantial deviation to the sides. Optionally, the beam is softly focused, for example, the US emitter is slightly curved, but not curved enough for the US beam to converge at a focal point. For example, not to a focal point, but to a volume relatively larger than if the beam was focused. Optionally or additionally, the beam is somewhat defocused. Optionally or additionally, the beam is broad, for example, slightly diverging. Optionally or additionally, the beam is unfocused; for example, US energy is not directed towards a focal point. Optionally or additionally, the beam has an aperture angle which is small relative to the initial beam width, for example, less than about 10 degrees, less than about 15 degrees, less than about 20 degrees, less than about 30 degrees, or other smaller, intermediate or larger angles. A potential advantage is that the beam energy density is substantially distance independent, except for absorption in tissue. Potentially, the distance between the beam source and the target area does not need to be controlled.

In an exemplary embodiment of the invention, the energy density of the beam is relatively high (exemplary values described through the specification). Potentially, the high energy density allows for effective tissue interactions, for example, nerve treatment without significant heat damage to surrounding tissues.

In an exemplary embodiment of the invention, the radiation of US from the flat plane provides for an ultrasound beam that has areas in which the energy density increases as a function of distance from the source, for example, in hot spot regions caused by additive interference of the US waves.

In an exemplary embodiment of the invention, the US beam is a non-uniform field, for example, due to interference between the US emanating from the edge of the emitter and from the central portions of the emitter forming patterns of hot spots. Alternatively or additionally, the non-uniform field is caused by variations in damping of the US emitter, for example, for the flat plate emitter supported at a plurality of areas, one or more areas can be damped to different degrees so that the emitter vibrates differently at the different areas producing local variations in the US beam.

In an exemplary embodiment of the invention, a memory 1720 is coupled to controller 1602. Optionally, memory 1720 stores one or more parameters related to the treatment plan (e.g., correlation values), non-limiting examples include; treatment time, ultrasound intensity, ultrasound frequency, and/or other values as described herein. Optionally, memory 1720 contains one or more of the treatment parameters correlated with reduction in function of nerves carrying signals from the carotid baroreceptors to the brain. Alternatively or additionally, memory 1720 contains one or more treatment parameters correlated with reduction in function of sympathetic nerves surrounding stenotic arteries. Alternatively or additionally, memory 1720 contains one or more treatment parameters correlated with the formation of treatment regions (e.g., reduction in nerve function) in a wall of a lumen containing a deployed stent. Alternatively or additionally, memory 1720 contains one or more treatment parameters correlated with the formation of treatment regions (and/or reduction in nerve function) around a first lumen when energy is applied from a second lumen.

In an exemplary embodiment of the invention, a feedback module 1730 is coupled to controller 1602. Optionally, module 1730 is programmed to analyze returning signals from catheter 1222, non-limiting examples include; efficiency of transducer, impedance, blood temperature. Optionally, module 1730 adjusts one or more settings to obtain the desired results, and/or stops the transmission of energy if there is a safety issue.

In an exemplary embodiment of the invention, controller 1602 uses memory 1720 and/or memory 1730 to set and apply parameters. Optionally, controller 1602 compares feedback (e.g., from feedback module 1730) to the data on memory 1720 and/or 1730. Optionally, the treatment parameters are changed according to the comparison.

In an exemplary embodiment of the invention, an imaging module 1740 is coupled to controller 1602. Optionally, module 1740 is programmed to analyze returning signals from transducer 1762 and/or other energy emission elements, for example, to image the arterial wall using ultrasound energy, for example, Doppler.

In some embodiments of the invention, catheter 1222 is sold pre-marked and/or pre-packaged with settings to obtain the desired effect. Optionally, memory 1750 is coupled to catheter 1222 and contains the settings, for example, the settings of memory 1720. In some embodiments, catheter 1222 is plugged into controller 1602, for example through port 1606, programming controller 1602 with the settings of catheter 1222 (e.g., on memory 1750). Some non-limiting examples of possible catheters 1222 include; a catheter with pre-settings for reducing renal nerve function by at least 50% when energy is applied to the right renal artery from the inferior vena cava and/or to the left renal artery from the left renal vein), a catheter with pre-settings for reducing sympathetic limb nerve function by at least 30% or by at least 50% when applied through a stenotic lumen, a catheter with pre-settings for reducing nerve function by at least 30% or by at least 50% when energy is applied across a stent in the lumen, a catheter with pre-settings for reducing function of nerves carrying signals from carotid baroreceptors by at least 30% or by at least 50%, or other settings as described herein are possible.

In an exemplary embodiment of the invention, one or more functions and/or parameters and/or settings are programmed and/or set into controller 1602 and/or stored on memory 1720 (e.g., automatically determined by software such as according to a treatment plan). Optionally or additionally, one or more functions and/or parameters are selectable (e.g., manually set by a user, automatically selected by software).

In an exemplary embodiment of the invention, feedback module 1730 and/or imaging module 1740 are configured for detecting a stent in the vicinity of transducer 1762. In some embodiments, at least a part of the stent is positioned between the energy emitting element and the vessel wall. Optionally, at least a portion of the vessel wall surface area such as 20%, 40%, 80% and/or intermediate or higher values is covered by the stent. In some embodiments, each setting of the stent, for example as described above, has a predefined parameter setting.

In some embodiments, the stent is detected using ultrasonic echo signals, for example by detecting varying intensity of the returning signals. Optionally, the energy emission element sends and/or receives signals to and back from the stent.

In some embodiments, the system can operate in a stent mode. Optionally, the stent is detected, and the stent mode is activated automatically. In some embodiments, the stent mode is selected by the user. In some embodiments, the system includes a safety feature for detecting a stent and/or lack thereof. In some embodiments, the system detects if the stent is positioned between, for example, an energy beam and a vessel wall. Optionally, the distance between them is detected.

In some embodiments, user interface 1604 is configured for selecting a mode for treating through a stent. Optionally, stent parameters such as material, size, thickness, thermal conductivity etc. are manually selected by user. Additionally and/or alternatively, stent parameters are automatically selected by the system, for example based on an image acquired of the stent by imaging module 1740. In some embodiments, a mode for treating through a stent includes using parameters such as intensity and frequency that are different than the ones used for non-stented vessels. Optionally, these parameters are automatically selected by the system. Optionally, these parameters are based on previously collected data, for example as shown in the table below.

In an exemplary embodiment, a user may select a mode for treating through a stent, and the system (for example using controller 1602 and/or data saved on memory 1720) automatically applies parameters suitable for treating through a stent. Optionally, the selected parameters allow compensating for the existence of the stent, for example by increasing the emission intensity by 10%, 20%, 40%, 90%, and/or intermediate or higher or lower values.

The table below is an example of data collected during experimental treatment. Stainless steel, cobalt alloy and cobalt chromium stents were used in the experiment. Exemplary parameter sets including frequency, intensity, duration, and catheter type were tested for treatments performed through a stent, and in the last example for treatment performed in a non stented vessel.

| Frequency (MHz) | Intensity (W/cm^2) | Time (sec) | Catheter type | Tissue effect |
|---|---|---|---|---|
| 20 | 30 | 30 | Unidirectional | Medium |
| 11 | 30 | 40 | Multidirectional | Very Mild |
| 11 | 35 | 40 | Multidirectional | Mild |
| 11 | 30 | 40 | Unidirectional | Very Mild |
| 11 | 35 | 40 | Unidirectional | Mild |
| 11 (no stent) | 35 | 40 | Unidirectional | Strong |

In the experiment described by the above table, no significant mechanical and thermal effects were observed in the stents. No irritation was observed on the tissue surrounding the stent. A thermal effect was observed mainly in the perivascular soft tissue (such as adipose tissue, connective tissue, and nerves). The collected data shows a correlation between the thermal effect on the tissue and the selected treatment frequency—a higher frequency may create a stronger thermal effect on the treated tissue. The above described parameters may also be applied to U.S. application Ser. No. 13/449,539. The settings such as frequency, intensity, or time may be modified for example by 5%, 10%, 15%, 20% or intermediate, lower or higher numbers, for example to receive the desired effects and/or the designated damage pattern.

One or more non-limiting examples of selectable parameters (e.g., can be set for example by the user using the controller) include:

Frequency of the produced ultrasound energy.

Waveform applied to the acoustic element, for example, a sinusoidal wave.

Intensity is the produced ultrasound power divided by the surface area of the acoustic element.

Pulse duration is the length of a pulse of acoustic energy measured in time.

Duty cycle is the percentage of time in a single pulse that ultrasound energy is transmitted.

Target temperature is the estimated and/or measured temperature of the blood near the transducer. Potentially, limiting the elevation in blood temperature to a pre-set value also sets a safety constraint.

Energy delivery pattern is the spatial and/or temporal combination of one or more of the above variables, for example, a single pulse, a sequence of pulses, a train of pulses.

Correlation parameters between selected reductions in nerve activity (e.g., NE levels) and treatment parameters (e.g., frequency, time, intensity) and/or geometrical parameters (e.g., number of treatment locations, size of treatment area). In some embodiments, a table of correlation parameters is used.

Alternatively or additionally, one or more equations provide the correlation.

The table below sets out some examples of the selectable parameters, and provides their theoretical limits, an exemplary treatment range, and an exemplary treatment sub range (e.g., most commonly used settings). It is important to note that some selectable parameters can only be selected from a pre-determined set, for example, in some embodiments; catheters are designed to operate at a specific frequency, in which case the user selects the frequency according to the catheter availability.

| Parameter | Exemplary Treatment sub range | Exemplary Treatment range | Broadest range |
|---|---|---|---|
| Frequency (MHz): | | | |
| Treatment | 10-22 | 8-30 | 1-60 |
| Imaging | 10-25 | 10-60 | 1-60 |
| Intensity (Watts/sq cm) | 10-60 | 10-100 | 1-200 |
| Duty cycle (%) | 50-100 | 10-100 | 0.1-100 |
| Pulse duration (seconds) | 0.1-2 | 0.1-4 | 0.01-1000 |
| Duration of treatment (Seconds) per location | 3-60 | 2-120 | 0.1-1000 |
| Efficiency (%) | 35-70% | 20-70% | 1-70% |
| Blood Temp (Celsius) | 37-51 | 37-60 | 37-100 |

General

It is expected that during the life of a patent maturing from this application many relevant treatment methods will be developed and the scope of the term treatment method is intended to include all such new technologies a priori.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof. Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Experiment of Treating the Right Renal Artery from the Inferior Vena Cava

Goal: Inventors performed a study to evaluate the clinical feasibility and/or safety of forming areas of treated tissues surrounding the right renal artery, by applying energy from the inferior vena cava.

Experimental Materials

Equipment: An ultrasound emission element, catheter and control system as described herein and/or in the references were used to perform the treatments. The catheter is currently being developed under the name TIVUS™, generally as described in U.S. patent application Ser. No. 13/049,151 and/or PCT/IB2011/054635. The US emitter is flat and rectangular, measuring 6 mm (along the long axis of the catheter) X 1 mm (along the radial dimension of the catheter).
Animals: Two pigs were treated.
Study End Points: Inducing damage to nerves underlying and/or along the right renal artery, while preserving the intima of both renal artery and inferior vena cava.

Experimental Protocol

Ultrasonic Treatment: In the treated swine, the TIVUS™ catheter was introduced via a femoral approach, from the femoral vein to the inferior vena cava. The location of the right renal artery was visually confirmed using contrast injection through a commercial guiding catheter introduced through the femoral artery. Ultrasound treatment, in accordance with some embodiments of the invention, was administered through the inferior vena cava towards the proximal (relative to the aorta) main trunk of the right renal artery in several locations (cranially, caudally and parallel to the renal artery plane, as presented in FIG. 6. The locations of ultrasonic ablation from the vena cava towards the right renal artery are shown as "*"). In each location, the ultrasound energy was directed in up to 3 angles by rotating the ultrasonic transducer along the long axis of the catheter, each rotation about 90 degrees relative to the previous position. Ultrasound was applied for 30 or 40 seconds at each treatment location. Ultrasound was applied at 10 MHz Frequency and an intensity of about 30-40 W/cm$^2$. About 14-17 ultrasonic treatments were performed in the right renal artery at 2-3 locations along the artery.

The catheter distance from the vein wall was measured using ultrasonic imaging of the system, prior to ultrasonic excitation, for example, as described in PCT/IB2011/054639 and/or PCT/IB2011/054638, incorporated herein by reference in their entirety.

Figures 7A, 7B, 7C, 7D:
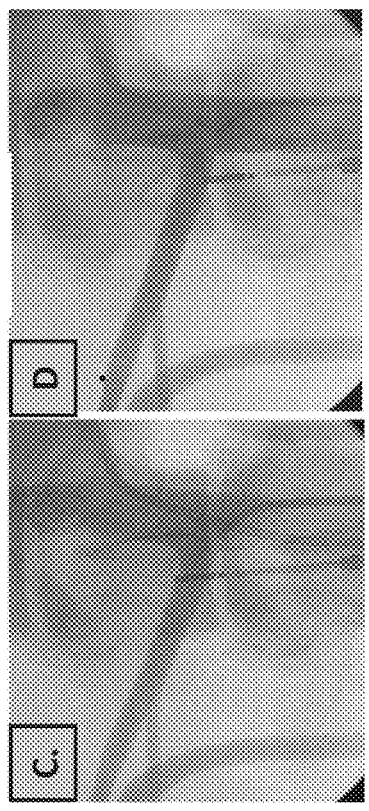

FIG. 7A is an angiography image of the relationship between the inferior vena cava and the right renal artery (noted by the guiding catheter). FIGS. 7B, C and D are angiography images of the locations of the TIVUS™ catheter cranially, caudally and parallel relative to the right renal artery plane.

Angiography: Angiography was performed during three time periods; prior to the procedure, during procedure and immediately at the end of procedure. Under angiography, each renal artery was examined by a trained veterinarian for vasospasm and/or any abnormalities in blood flow.

Figure 7E:
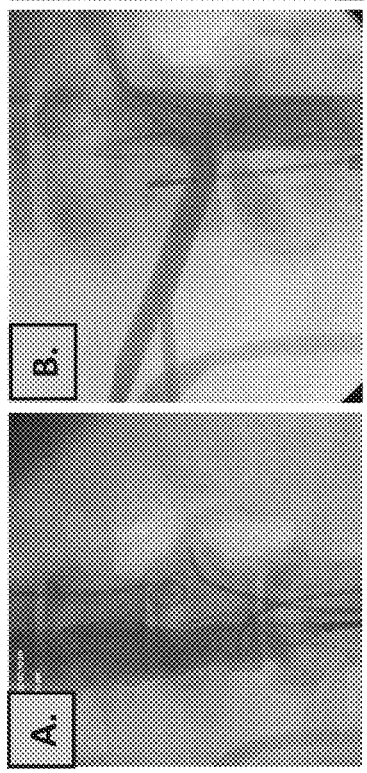
Figure 7F:
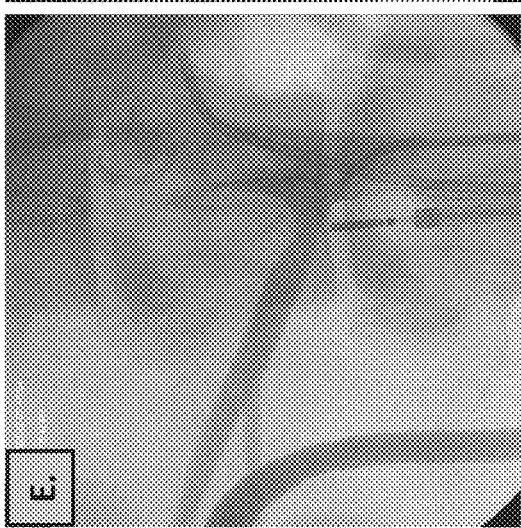

Immediately following treatment a temporary vasospasm was depicted in the renal artery as a result of the ultrasonic ablation (FIG. 7E). No vasospasm was depicted at the end of procedure (FIG. 7F).

Histology: Following treatment, the renal arteries and kidneys were perfused, dissected and immersed in 4% formalin prior to histological processing. Pathological examination included looking for any thermal or mechanical damage to the renal artery or vein, or to adjacent soft tissue, including nerves.

Results: FIGS. 8A-C illustrate histological slides, showing circumferential damages to peri-vascular tissue and/or nerves, showing results of some embodiments.

FIG. 8A: Histopathological analysis of the damage to the right renal artery following ultrasonic treatment from the inferior vena cava in Pig#1. The figure shows damage to perivascular tissue (including connective and adipose tissue) and to nerves.

FIG. 8B: Histopathological analysis of the damage to the right renal artery following ultrasonic treatment from the inferior vena cava in Pig #2. The figure shows damage to perivascular tissue (including connective and adipose tissue) and to nerves.

FIG. 8C: Histopathological analysis of the damage to the right renal artery following ultrasonic treatment from the inferior vena cava in Pig#2 . The figure shows damage to perivascular tissue (including connective and adipose tissue) and to nerves.

In the figures, the damage regions are located within about 1 mm to about 5 mm from the intima of the artery. The damaged regions have dimensions of about 4 mm (measured substantially tangentially to the artery) and about 7 mm (measured radially from the inner wall of the artery), or about 1 mm and 3 mm, or about 1 mm and 1 mm. The damage regions are located a distance of about 1 mm to 10 m from the intima of the vena cava. All of the damaged regions (from the different treatments) were spread around a total area of 20% to 70% of the perivascular tissue circumference of the renal artery as measured in cross section.

Conclusion: The results provide support that one or more areas of damage can be selectively formed around the renal artery with ultrasonic energy delivered from the inferior vena cava.

Limb Denervation Experiment

Goal: Inventors performed a study to evaluate the ability to treat tissues in the wall of a femoral artery, by application of ultrasound energy from within a stenosed femoral artery.

Experimental Materials:

Equipment: An ultrasound emission element, catheter and control system as described herein and/or in reference applications by the same inventors were used to perform the treatments. The catheter is currently being developed under the name TIVUS™. The ultrasonic catheter is sufficiently small and/or rigid to be successfully inserted into the stenotic lumen.

Experimental Model: Recently amputated human legs donated from a patient having undergone an amputation. To simulate blood flow cooling, saline was perfused through the femoral artery.

Study End Points: inducing effect in a stenotic femoral artery wall.

Experimental Protocol:

Ultrasound was applied to the arteries for 30 seconds at each treatment location. Ultrasound was applied at a frequency of 20 MHz, and power level of about 20-40 W/cm^2. About 8-14 ultrasonic treatments were performed at several locations along arteries in the amputated legs.

Results: FIGS. 12A-B are histological slides of cross sections through the treated femoral artery. Note the treatment region in the arterial wall. The lumen is stenotic due to an atherosclerotic plaque. Furthermore, the arterial wall is calcified. For clarity, a schematic of the ultrasonic catheter cross section is provided in the artery lumen (FIG. 12B).

Conclusion: The results provide support that tissue in the arterial wall can be targeted and treated, even in the presence of atherosclerotic plaques and a calcified wall. The ultrasound successfully traverses the plaque and the calcification to form the treatment region.

Experiment: Ultrasound Treatment Through a Stent

Goal: Inventors performed a study to evaluate the ability to treat tissues by applying ultrasound energy through a stent deployed in the artery.

Experimental Materials

Equipment: ultrasound emission elements, catheter and control system as described herein and/or in the references were used to perform the treatments. The catheter is currently being developed under the name TIVUS™.

Stents: Several conventional stainless steel, cobalt alloy or cobalt chromium stents, which are capable of expanding to a diameter in a range of 5-8 mm, and have a length of about 15-30 mm.

Animals: Three swine were treated.

Study End Points: inducing damage to perivascular tissue and nerves underlying along the renal arteries by TIVUS™ positioning and energy applying within the stents. The treatment should not cause stent deformation or further intimal damage than induced by the stent.

Figure 13A:
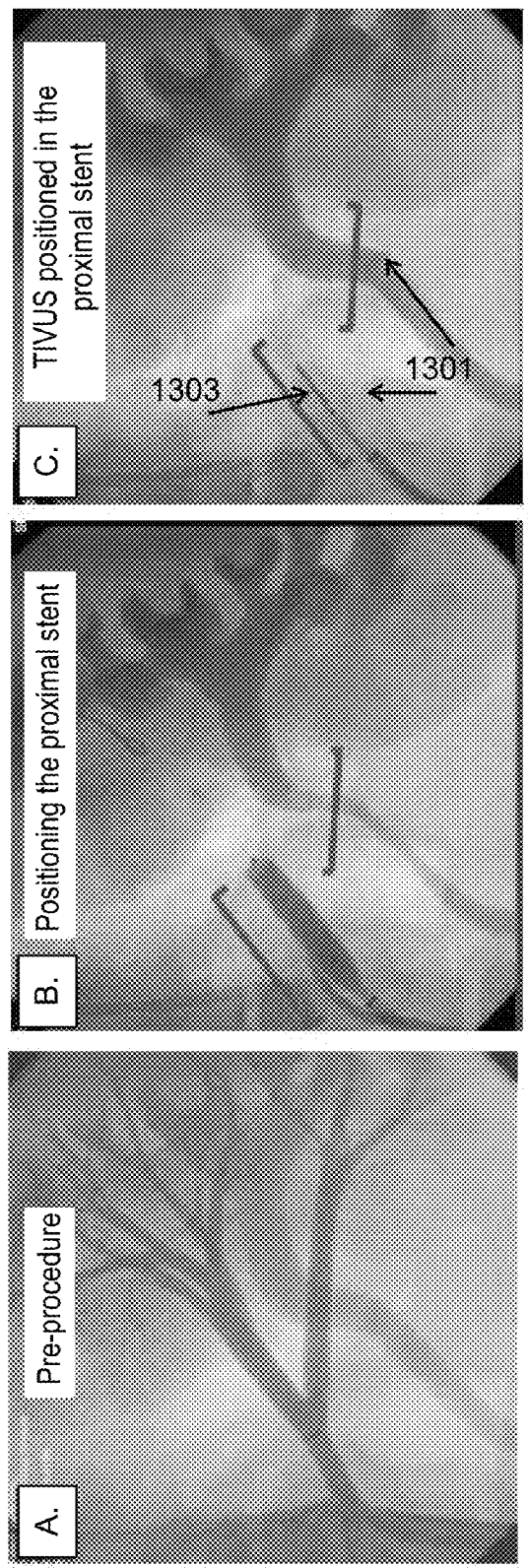

Experimental Protocol:

Animal A: Two stents 1301 were deployed in the left renal artery, as shown in FIGS. 13A (B and C), which are angiographic images. A first stent was deployed in the caudal bifurcating left renal artery and afterwards a second stent was deployed in the main stem of the left renal artery. The TIVUS™ 1303 was positioned within the stent lumen and US energy was applied through the stent. Ultrasound treatment, in accordance with some embodiments of the invention, was administered at each stent site in one or more locations. In each location, the ultrasound energy was directed in up to 4 angles of the arterial circumference (e.g., 0°, 90°, 180°, 270°—equivalent to 12, 3, 6, 9 o'clock in a clock model). Ablation of neural tissue was performed by ultrasonic excitation of 20 MHz at an intensity of about 30 Wcm^2 for 30 seconds in each treatment location. About 7 ultrasonic treatments were performed at 2 locations along the stents positioned in the left renal artery. In actual practice, a smaller or larger number of angles and/or locations may be used.

Figures 18A, 18B, 18C, 18D, 18E, 18F:
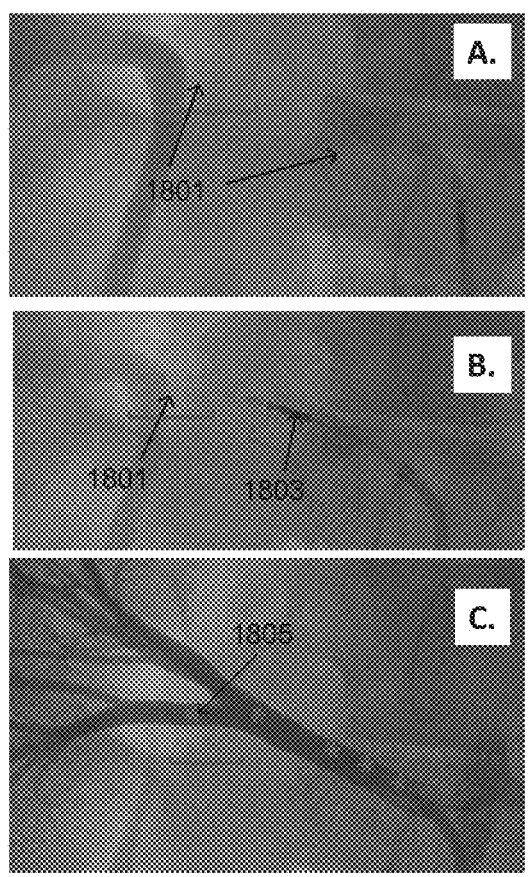

A similar treatment protocol was performed in Animal C. FIGS. 18D-F are angiographic image showing deployed stents 1801 in the left renal artery, and a unidirectional TIVUS catheter 1807. Ablation of neural tissue was performed by ultrasonic excitation of 10 MHz at an intensity of about 35 Wcm^2 for 40 seconds in each treatment location 1805 using the unidirectional TIVUS catheter 1807 together with a steerable introducer, or alternatively using a TIVUS catheter which includes an inherent deflection mechanism. About 7-8 ultrasonic treatments were performed at 2-3 1805 locations along the stents positioned in the main stem of the renal artery, as seen on FIG. 18 F. In actual practice, a smaller or larger number of angles and/or locations may be used.

Animal B: Three stents 1801 were deployed in the right renal artery, as shown in FIGS. 18A-B. A first stent was deployed in the main stem of the right renal artery, a second stent was deployed in the caudal bifurcating right renal artery, and a third stent was deployed in the main stem of the left renal artery. A triangle multidirectional TIVUS™ 1803 was positioned within the stent lumen, as seen in FIG. 18B. The multidirectional TIVUS™ may create 3 beams with 120 degrees between them. The ultrasonic treatment head of the multidirectional catheter 1803 is composed of 3 1*6 mm flat piezoelectric transducers attached to a triangle-shaped metal base, which are connected to a printed circuit base (PCB). A guide wire lumen extends from the catheter handle along the catheter shaft, through the metal base and up to the radiopaque non-traumatic tip. A lever in the catheter handle operates a 3-petal-shaped expanding structure. The expanding structure comprises a pebax-coated polyimide tube, cut into three bands (each having a width of about 1 mm), that can be bent and moved away from the ultrasonic transducers in order to keep the ultrasonic transducers away from artery wall. During catheter insertion, the expanding structure partially covers the ultrasonic transducers.

Ultrasound treatment, in accordance with some embodiments of the invention, was administered through each stent in one or more sites. In each site, the ultrasound energy was applied simultaneously to 3 angles of the arterial circumference (e.g., 0°, 120°, 240°—equivalent to 12, 4, 8 o'clock in a clock model Ablation of neural tissue was performed by ultrasonic excitation for a period of 40 seconds at each treatment location. The applied frequency was 10 MHz and the intensity range of 30-35 W/cm^2. Three to five (3-5) circumferential ultrasonic treatments were performed at 3-5 sites 1805 along and between the stents positioned in the renal arteries, as seen on FIG. 18C. In actual practice, the treatment may be applied to various numbers of sites, such as 1 site, 6 sites, 10 sites.

Results: In general, an endothelial loss, which often occurs during implantation of stents, was depicted.

As shown by the following table, when relatively high ultrasound frequencies were applied, they induced a more pronounced thermal effect on the tissue, creating mild smooth muscle cell loss and having a strong thermal effect on the perivascular tissue and nerves. When lower ultrasound frequencies were applied, usually no media damage was observed, and a mild to moderate thermal effect was induced on the nerves. There was no evidence in the tissue for stent heating during the ultrasonic treatment. One possibility is that the stent struts did not maintain direct contact with the intima layer, due to the processing of the tissue during the preparation of the slides for imaging.

Figure 13F:
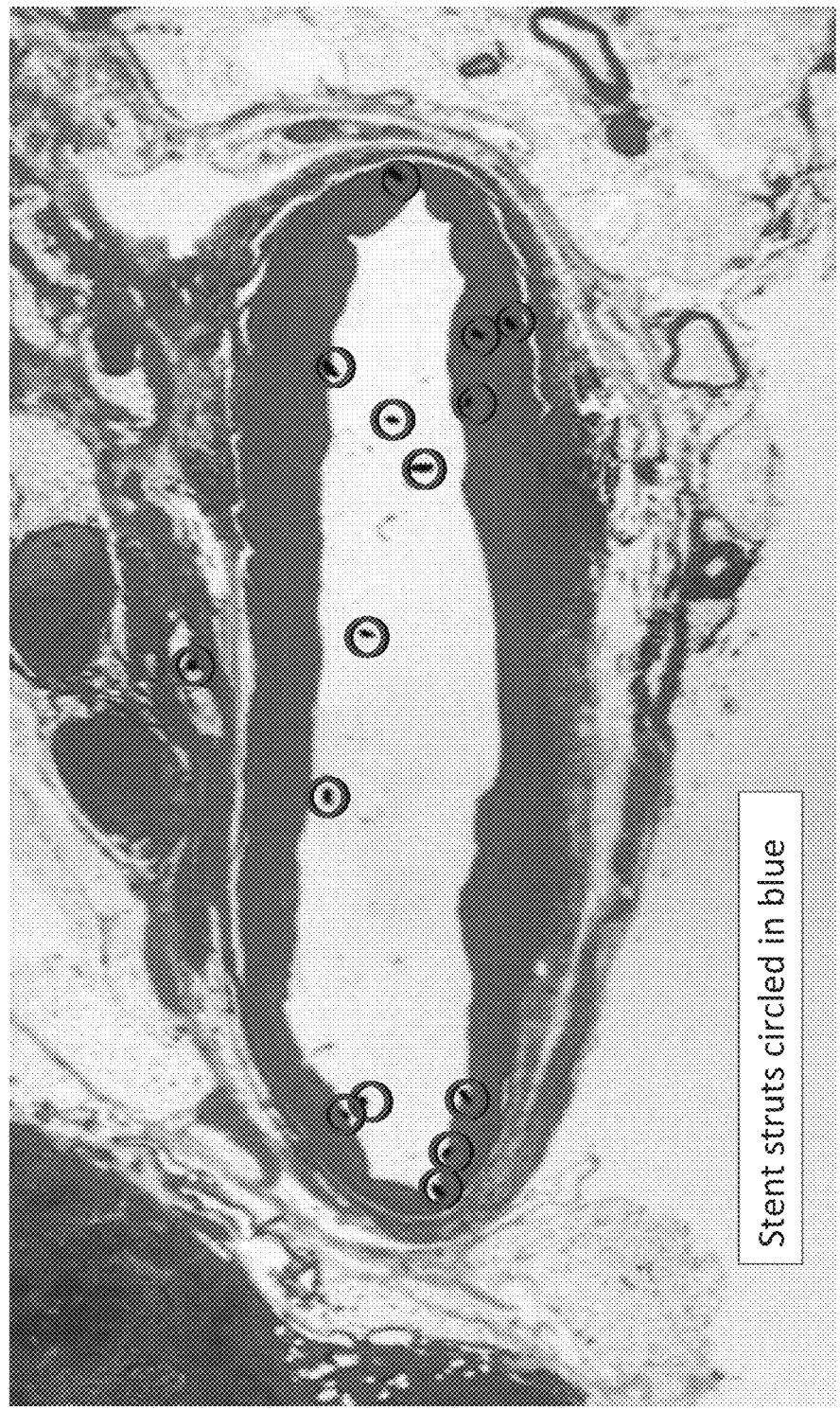

| Treatment frequency (MHz) | Treatment intensity (W/cm^2) | Catheter Type | Histopathology (figures) |
|---|---|---|---|
| 10 | 30 | Multidirectional TIVUS | FIG. 19A is a histological image (H&E) showing the damaged 1901 region in the renal artery wall and surrounding tissue. FIGS. 19C, D are an enlarged view of affected nerves 1903. Endothelial loss, which is typical to stents, was observed, but no media damage was observed. A mild to moderate nerve damage occured (vacuolization and mild nuclei pyknosis were observed), while the damage to the perivascular tissue was mainly insignificant, apart from an occasional moderate thermal effect on the soft tissue (shown in FIG. 19B). |
| 10 | 35 | Multidirectional TIVUS | Endothelial loss and minimal media damage were observed. Mild perineural inflammation, nuclei pyknosis, and vacuolation pointed to mild nerve damage. Damage to the perivascular tissue was insignificant. |
| 10 | 35 | Steerable TIVUS | Endothelial loss and minimal media damage were observed. vacuolization and mild nuclei pyknosis pointed to a minimal to mild nerve damage A mild damage to perivascular tissue was also observed. |
| 10 | 30 | TIVUS | FIG. 19E is histological image (H&E) showing damaged region 1905 in the renal artery wall and surrounding tissue. FIG. 19G is an enlarged view of the affected nerves and tissue 1907. Endothelial loss and minimal media damage were observed. Digestion chambers, vacuolization and mild nuclei pyknosis pointed to a minimal to moderate nerve damage. A mild damage to perivascular tissue was observed (FIG. 19F). |
| 20 | 30 | TIVUS | FIG. 13B is a histological image (H&E) showing the damaged region 1307 in the renal artery wall and surrounding tissue. FIG. 13C is an enlarged view of endoneural degenerated cells, some with vacuolated cytoplasm1309). effaced nerves were also observed along the artery. FIGS. 13D-E are images of adjacent cells with pyknotic nuclei1311. FIG. 13F is a close up image of the artery of FIG. 13B, showing the location of the stent struts (circled in blue). |

Conclusion: The results show that it is possible to apply ultrasound energy from within an artery, through a deployed stent, to damage tissue in the arterial perivascular tissue without creating a significant damage to the media or intima layers, which directly contact the stent. The results provide support that a predictable amount of US energy can be applied through the stent without heating the stent to a level that causes stent deformation and/or direct damage to the artery wall.

Experiment: Ultrasound Treatment of the Carotid Artery

Goal: Inventors performed a study to evaluate the ability to treat tissues by application of ultrasound energy in the carotid artery.

Experimental Materials:

Equipment: An ultrasound emission element, catheter and control system as described herein and/or in the references were used to perform the treatments. The catheter is currently being developed under the name TIVUS™.

Animals: 10 Swine.

Study End Points: inducing damage to the carotid artery wall (e.g. media, adventitia) and/or perivascular tissue and nerves adjacent to the carotid artery.

Experimental Protocol:

Ultrasonic Treatment: The TIVUS™ catheter was introduced via a femoral approach or carotid approach to the right or left carotid arteries. Ultrasound treatment, in accordance with some embodiments of the invention, was administered from the lumen of the carotid artery towards the circumferential tissue in several locations along the artery (for example, as shown in FIG. 10B). In each location, the ultrasound energy was directed in 4-8 longitudinal ablation points in a specific intensity. Then after, the catheter was pulled further to another 2 locations where energy was again applied in 4-8 longitudinal ablation points using higher intensity. Altogether the treatment lasted about 30 minutes. Additionally, in one of the location, the US energy was applied circumferentially as described in the renal artery experiment by rotating the ultrasonic transducer along the long axis of the catheter, each rotation about 45-90 degrees relative to the previous position. Ultrasound was applied for 5 up to 60 seconds at each treatment angle or location. Ultrasound was applied with a frequency of 10 MHz to 20 MHz, and an intensity of about 13-40 W/cm$^2$. About 10-20 ultrasonic treatments were performed in the right renal artery at 5-10 locations along the artery.

The catheter distance from the vein wall was measured using ultrasonic imaging of the system, prior to ultrasonic excitation, for example, as described in PCT/IB2011/054639 and/or PCT/IB2011/054638, incorporated herein by reference in their entirety.

Histology: Following treatment, the carotid arteries and adjacent tissue were perfused, dissected and immersed in 4% formalin prior to histological processing. Pathological examination included looking for any thermal or mechanical damage to the carotid artery or to adjacent soft tissue, including nerves.

Results: FIGS. 15A-B are histological images showing the location of the treatment regions in the carotid artery wall and surrounding tissue. As can be seen, there was damage to perivascular tissue (connective and adipose tissue, demarcated in blue line) as well as damaged nerves (marked as XN). In FIG. 15B there is also necrosis of smooth muscle cells in the media. Inventors hypothesize that the tissue damage was due to relatively higher energy intensities, for example, relative to intensities used to treat renal nerves.

Conclusion: The results provide support that ultrasound energy can be applied from the carotid artery and cause either remote and/or localized damage in the carotid artery wall and/or adjacent tissues, including nerves.

Experiment: Ultrasound Treatment of the Left Atrium

Goal: Inventors performed a study to evaluate the ability to treat tissues by application of ultrasound energy in the left atrium, to simulate treatment of atrial fibrillation.

Experimental Materials:

Equipment: An ultrasound emission element, catheter and control system as described herein and/or in the references were used to perform the treatments. The catheter is currently being developed under the name TIVUS™.

Animals: 1 Swine.

Study End Points: inducing damage to the full thickness of the myocardium without damage to the endocardium.

Experimental Protocol:

Ultrasonic Treatment: The TIVUS™ catheter was introduced through the chest and the apex of the heart to the left atrium, at the ostium of one of the pulmonary veins. Ultrasound treatment, in accordance with some embodiments of the invention, was applied to 4 different regions spaced apart by 90 degrees (by rotation of the catheter without axial displacement). Ultrasound was applied for about 30 seconds at each treatment location. Ultrasound was applied with a frequency of about 20 MHz, and at an intensity of about 30 W/cm$^2$. Then after, the TIVUS™ catheter was introduce to the ostia of other pulmonary veins for additional treatment.

The catheter distance from the heart wall was measured using ultrasonic imaging of the system, prior to ultrasonic excitation, for example, as described in PCT/IB2011/054639 and/or PCT/IB2011/054638, incorporated herein by reference in their entirety.

Histology: Following treatment, the left atrium and pulmonary veins were perfused, dissected and immersed in 4% formalin prior to histological processing. Pathological examination included looking for any thermal or mechanical damage to the heart wall.

Results: FIG. 17 is a histological image showing damage to the heart wall, as marked in black circles. Each of the circles represents a different treatment region caused by rotation of the catheter. The endocardium has not been damaged. Cells in the myocardium have been killed substantially along the full thickness of the myocardium (leaving a small undamaged gap between the damage area and the endocardium). For illustration purposes, a schematic shows a cross section of the catheter and US emission element, along with the direction of the US energy (arrow).

Conclusion: The results provide support that ultrasound energy can be applied from inside the heart to damage the thickness of the myocardium but not damage the endocardium, for example, to treat atrial fibrillation.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating tissue in a lumen wall and/or surrounding tissue comprising:

inserting a catheter including an energy emission element into a region of a lumen containing a deployed stent having a portion placed in direct contact with an intima of said lumen wall;

selectively applying energy from within said lumen, so that a beam from said energy emission element crosses said portion, to form one or more spaced apart regions of tissue damage in said lumen wall or surrounding tissue without damaging the intima in direct contact with said portion;

wherein said selectively applying energy comprises selecting treatment parameters as if said deployed stent was not present.

2. The method according to claim 1, wherein said lumen comprises a renal artery.

3. The method according to claim 1, wherein said energy emission element comprises an ultrasound emission element and wherein said beam is a beam of unfocused ultrasound.

4. The method according to claim 3, comprising one or more additional ultrasound emission elements, each producing a beam of unfocused ultrasound, the additional ultrasound emission elements directed at a plurality of different directions.

5. The method according to claim 1, wherein said deployed stent is deployed prior to said inserting of said catheter.

6. The method according to claim 1, wherein said selectively applying energy is performed without causing stent deformation.

7. The method according to claim 1, wherein blood flow through said lumen is selected to be high enough to cool said stent.

8. The method according to claim 1, further comprising detecting said stent using ultrasonic echo signals.

9. The method according to claim 1, wherein said portion said beam crosses, applies sufficient force on said intima to maintain a patent lumen.

10. The method according to claim 1, wherein said one or more spaced apart regions of tissue damage comprise nerves.

11. A method of treating tissue in a lumen wall and/or surrounding tissue comprising:

inserting a catheter including an energy emission element into a region of a lumen containing a deployed stent;

selectively applying energy from within said lumen, so that a beam from said energy emission element crosses struts of said deployed stent, to form one or more spaced apart regions of tissue damage in said lumen wall or surrounding tissue without damaging an intima in direct contact with said deployed stent, wherein said selectively applying energy comprises selecting treatment parameters as if said deployed stent was not present and wherein said deployed stent whose struts said beam crosses is in direct contact with said intima.

* * * * *